(12) United States Patent
Johnston et al.

(10) Patent No.: US 6,426,703 B1
(45) Date of Patent: Jul. 30, 2002

(54) CARBON MONOXIDE AND SMOKE DETECTION APPARATUS

(75) Inventors: Derek Scott Johnston, Batavia; Vincent J. Delia, Melrose Park, both of IL (US)

(73) Assignee: BRK Brands, Inc., Aurora, IL (US)

( * ) Notice: Subject to any disclaimer, the term of this patent is extended or adjusted under 35 U.S.C. 154(b) by 0 days.

(21) Appl. No.: 09/058,467

(22) Filed: Apr. 9, 1998

Related U.S. Application Data

(63) Continuation-in-part of application No. 60/055,009, filed on Aug. 7, 1997.

(51) Int. Cl.$^7$ ............................................. G08B 17/10
(52) U.S. Cl. ........................ 340/628; 340/629; 340/630; 340/632; 340/693.5; 340/691.5; 422/86; 422/94; 73/23.25; D10/106
(58) Field of Search .................................. 340/628, 629, 340/632, 630, 693.5, 691.5; 422/86, 94; 73/23.25; D10/106

(56) References Cited

U.S. PATENT DOCUMENTS

| | | |
|---|---|---|
| 1,154,128 A | 9/1915 | Rich |
| 2,153,568 A | 4/1939 | Johnson |
| 3,027,522 A | 3/1962 | Landis |
| 3,114,610 A | 12/1963 | Gafford et al. |
| 3,276,004 A | 9/1966 | Mayo, Jr. |
| 3,305,852 A | 2/1967 | Cates, Jr. |
| 3,445,669 A | 5/1969 | Jordan et al. |
| 3,577,222 A | 5/1971 | Ward |
| 3,790,348 A | 2/1974 | Bossart et al. |
| 3,922,656 A | 11/1975 | Horvath et al. |
| 3,970,431 A | 7/1976 | Wise |
| 4,030,887 A | 6/1977 | Poli et al. |
| 4,043,934 A | 8/1977 | Shuler et al. |
| 4,088,986 A | 5/1978 | Boucher |
| 4,225,860 A | 9/1980 | Conforti |
| 4,231,249 A | 11/1980 | Zuckerman |
| RE30,620 E | 5/1981 | Sweany et al. |
| 4,297,689 A | 10/1981 | Shaw et al. |
| 4,316,184 A | 2/1982 | Nagel |
| 4,327,575 A * | 5/1982 | Locker ........................... 73/23 |
| 4,384,283 A | 5/1983 | Drope et al. |
| 4,401,978 A | 8/1983 | Solomon |
| 4,405,919 A | 9/1983 | Scheidweiler |
| 4,421,720 A | 12/1983 | Kamiya et al. |
| 4,453,222 A * | 6/1984 | Goszyk .................... 364/513.5 |
| 4,595,914 A * | 6/1986 | Siegel ......................... 340/515 |
| 4,617,277 A | 10/1986 | Bohl |
| 4,647,914 A * | 3/1987 | Alexandria .................. 379/44 |
| 4,683,463 A | 7/1987 | Kimura |
| 4,688,021 A | 8/1987 | Buck et al. |
| 4,790,857 A | 12/1988 | Miksch |
| 4,803,052 A | 2/1989 | Abromaitis et al. |
| 4,860,223 A | 8/1989 | Grilk |

(List continued on next page.)

OTHER PUBLICATIONS

US Patent Application Ser. No. 08/845,614, Sealed Replaceable Sensor.

Primary Examiner—Julie Lieu
(74) Attorney, Agent, or Firm—Welsh & Katz, Ltd.

(57) ABSTRACT

A smoke sensor and a carbon monoxide sensor are integrated into a common detector housing. The smoke sensor is coupled to a smoke detector control integrated circuit which generates a binary output signal indicative of the presence of smoke. This signal is coupled to a programmed microprocessor in the detector housing. The carbon monoxide sensor is also coupled to the microprocessor. Outputs from the two sensors are processed substantially independently. In the presence of smoke, the smoke alarm is generated by the microprocessor. In the presence of sufficient levels of carbon monoxide, in the absence of smoke, a carbon monoxide alarm will be generated.

36 Claims, 38 Drawing Sheets

U.S. PATENT DOCUMENTS

| | | |
|---|---|---|
| 4,884,222 A | 11/1989 | Nagashima et al. |
| 4,904,878 A * | 2/1990 | Gipp et al. ................. 250/577 |
| 5,121,101 A | 6/1992 | Jakubowski et al. |
| 5,243,330 A | 9/1993 | Thuillard |
| 5,276,434 A | 1/1994 | Brooks et al. |
| 5,280,273 A | 1/1994 | Goldstein |
| 5,289,165 A * | 2/1994 | Belin ......................... 340/628 |
| 5,331,310 A | 7/1994 | Stetter et al. |
| 5,369,397 A | 11/1994 | Wong |
| 5,400,013 A | 3/1995 | Mochizuki |
| 5,471,194 A | 11/1995 | Guscott |
| 5,486,811 A | 1/1996 | Wehrle et al. |
| 5,573,953 A | 11/1996 | Marnie et al. |
| 5,594,422 A * | 1/1997 | Huey, Jr. et al. ............ 340/628 |
| 5,596,314 A * | 1/1997 | Goldstein ................... 340/632 |
| 5,598,147 A | 1/1997 | Mochizuki et al. |
| 5,621,394 A | 4/1997 | Garrick et al. |
| 5,633,501 A | 5/1997 | Amleshi et al. |
| 5,644,116 A | 7/1997 | Noda et al. |
| 5,751,219 A * | 5/1998 | Stegmueller ............. 340/815.4 |
| D396,820 S * | 8/1998 | Wallace ..................... D10/106 |
| 5,793,295 A * | 8/1998 | Goldstein ................... 340/632 |
| 5,939,981 A * | 8/1999 | Renney ..................... 340/539 |
| 6,060,991 A * | 5/2000 | Hsieh ........................ 340/632 |

* cited by examiner

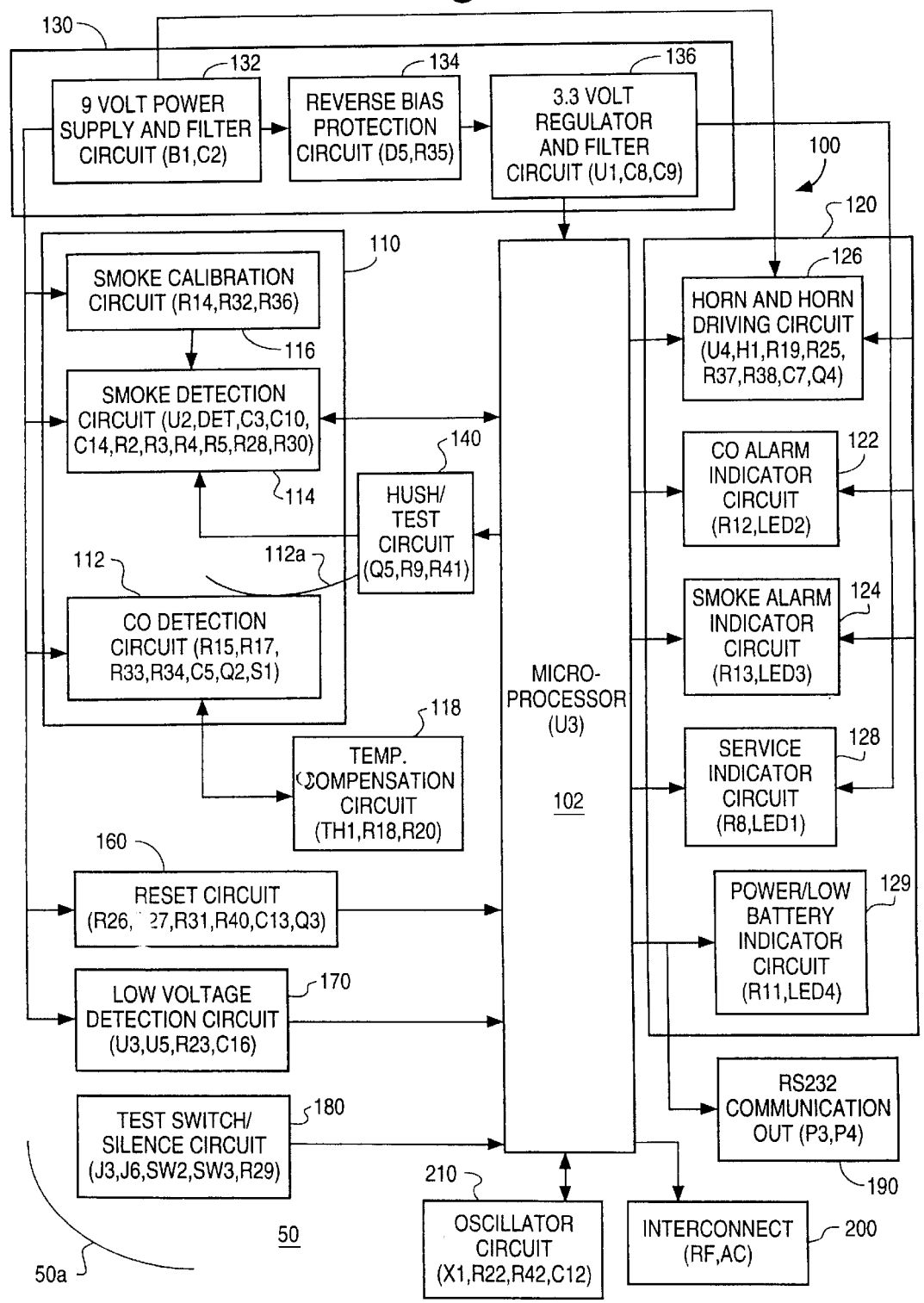

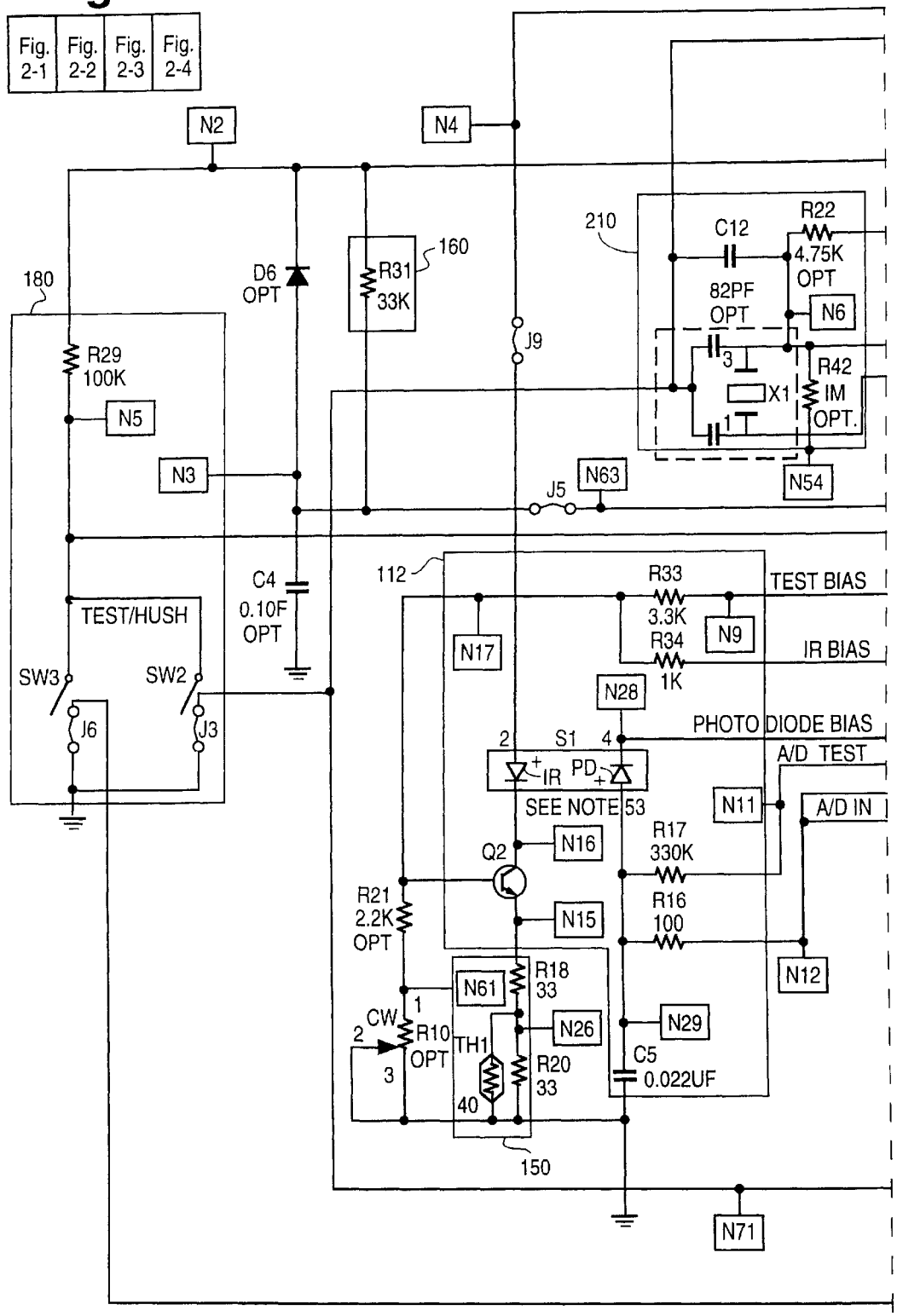

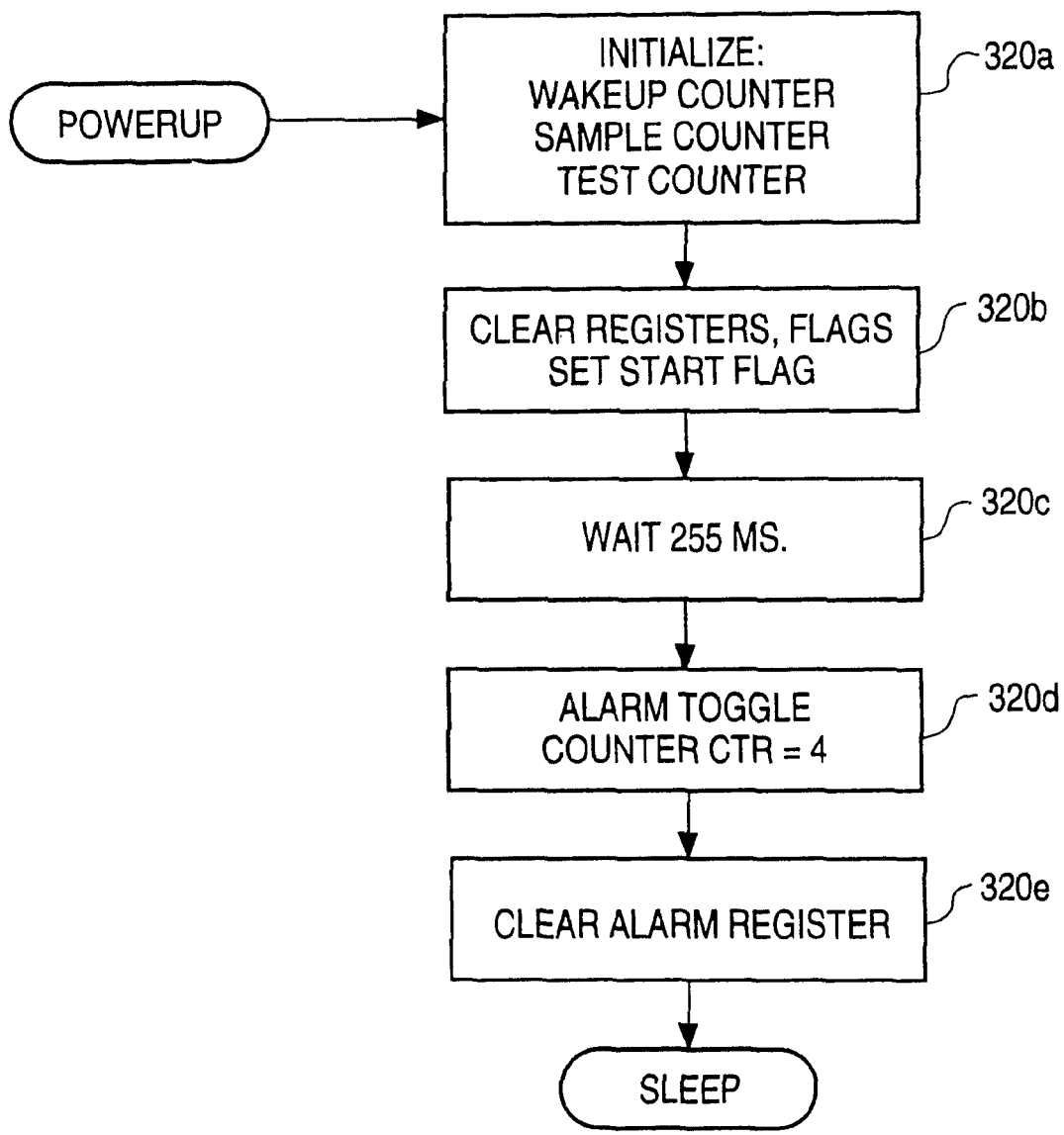

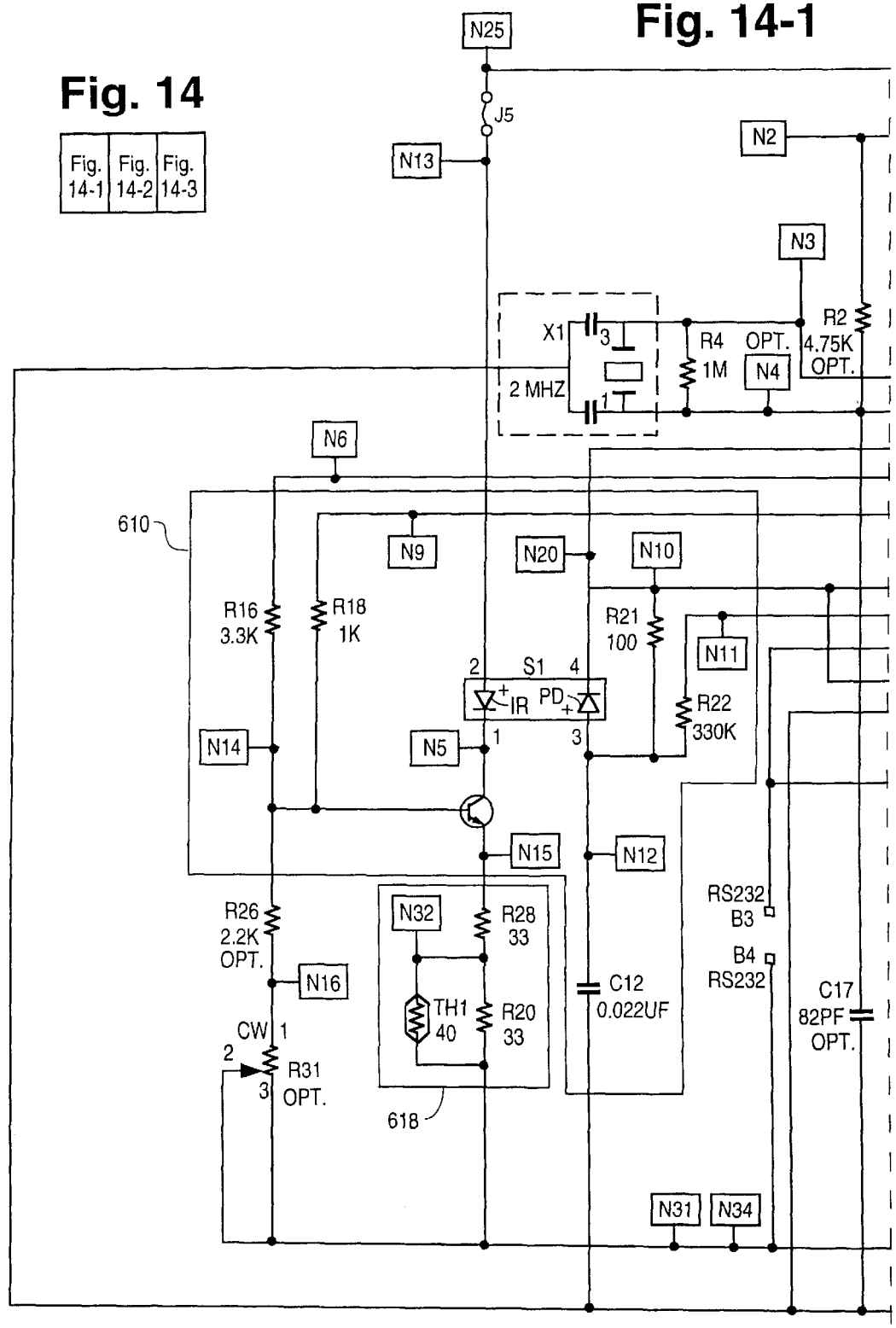

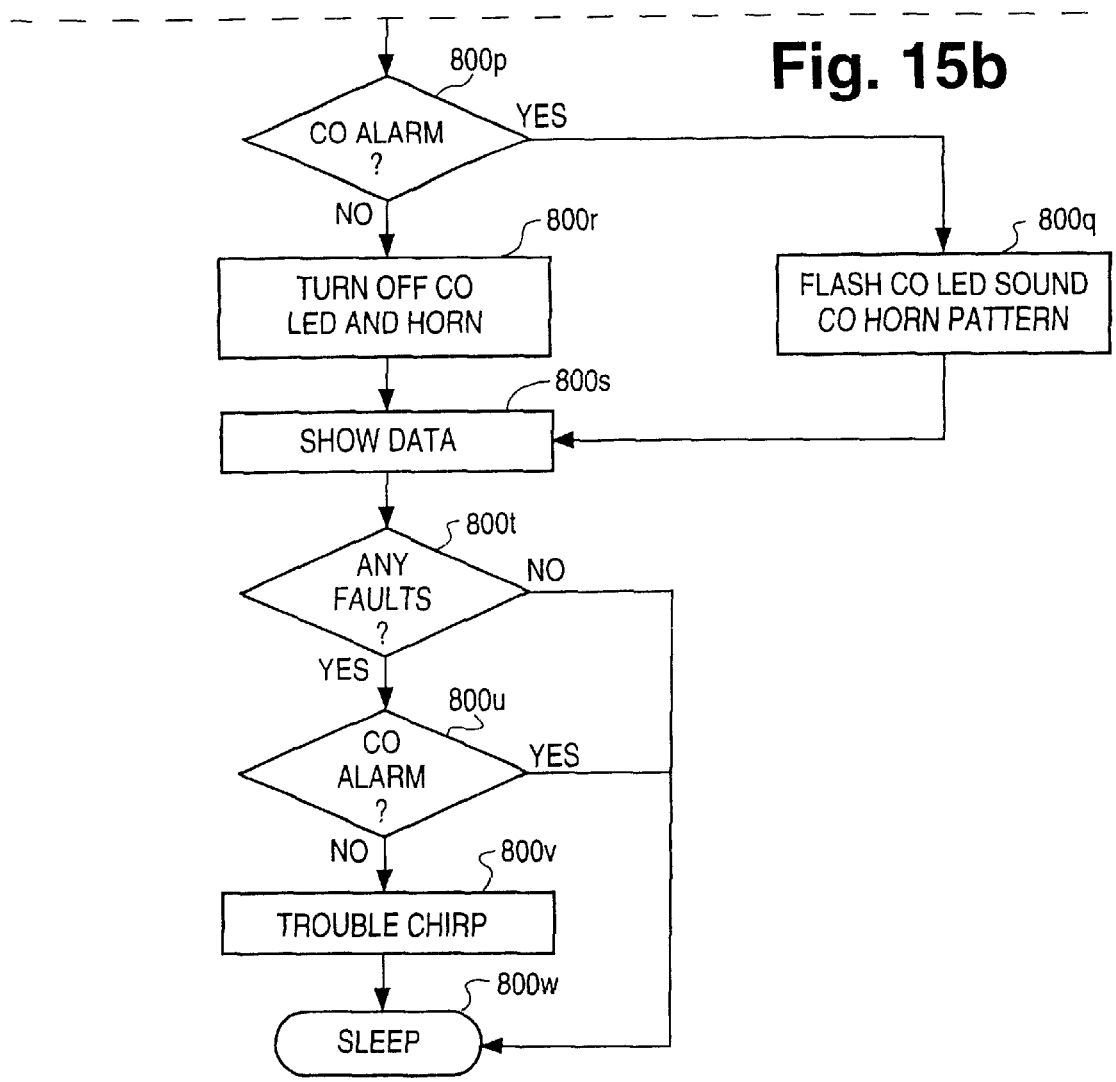

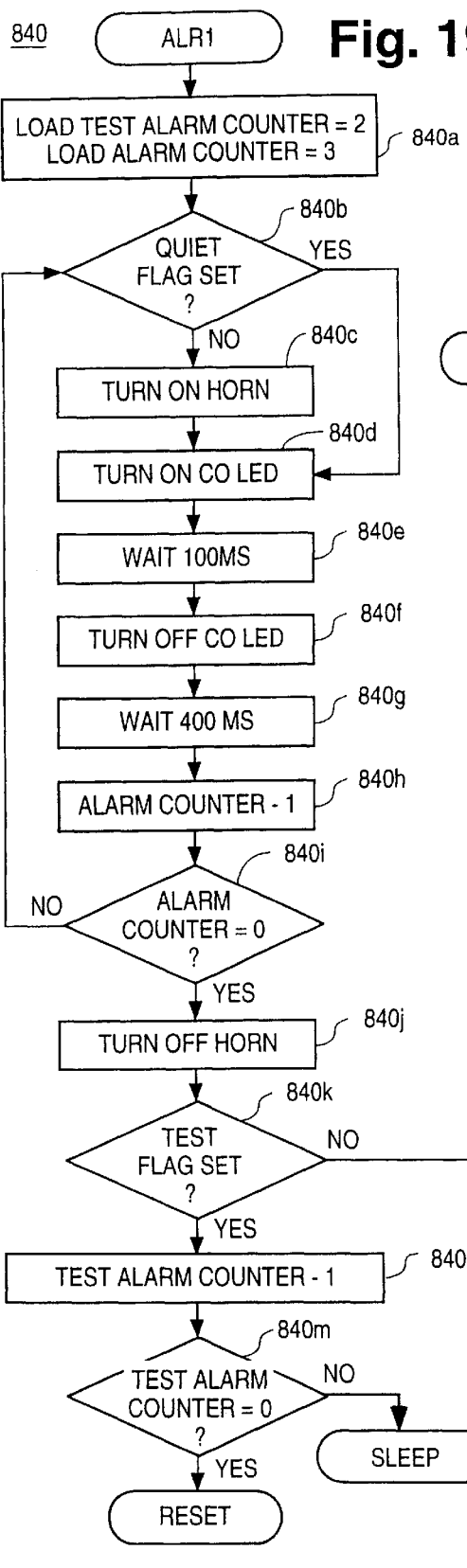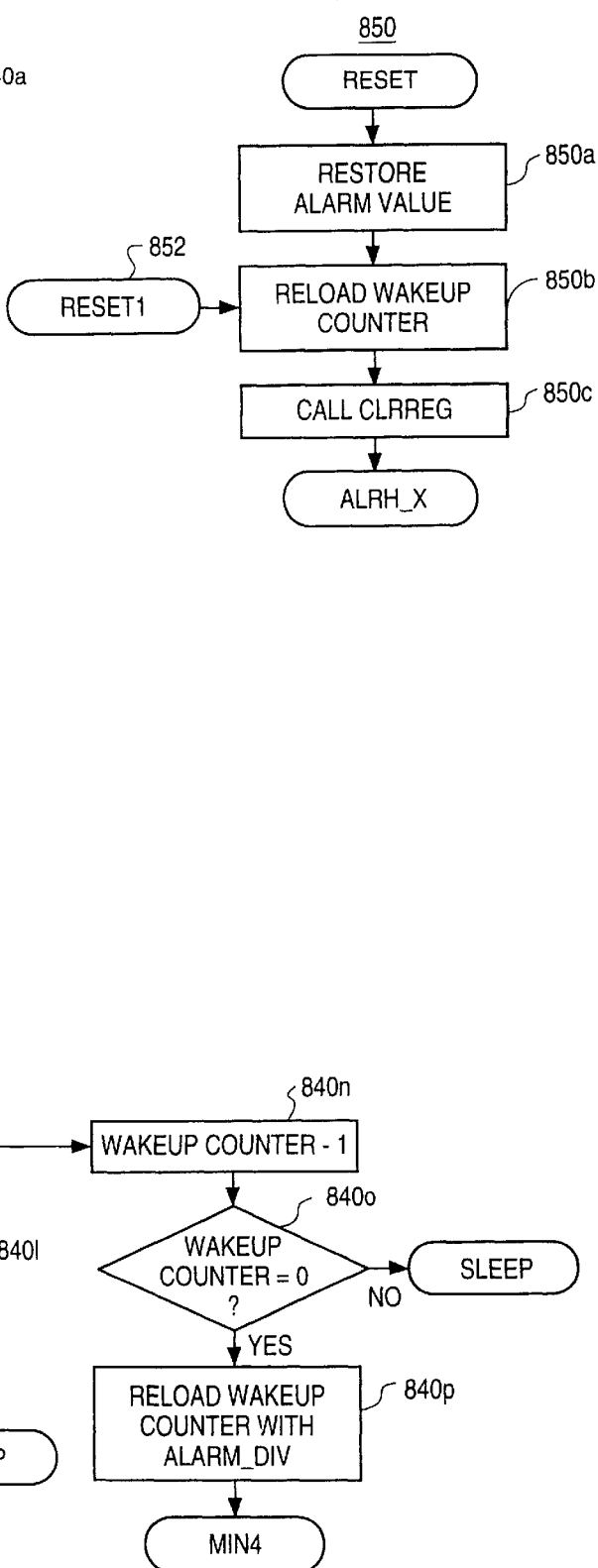
Fig. 19
Fig. 20

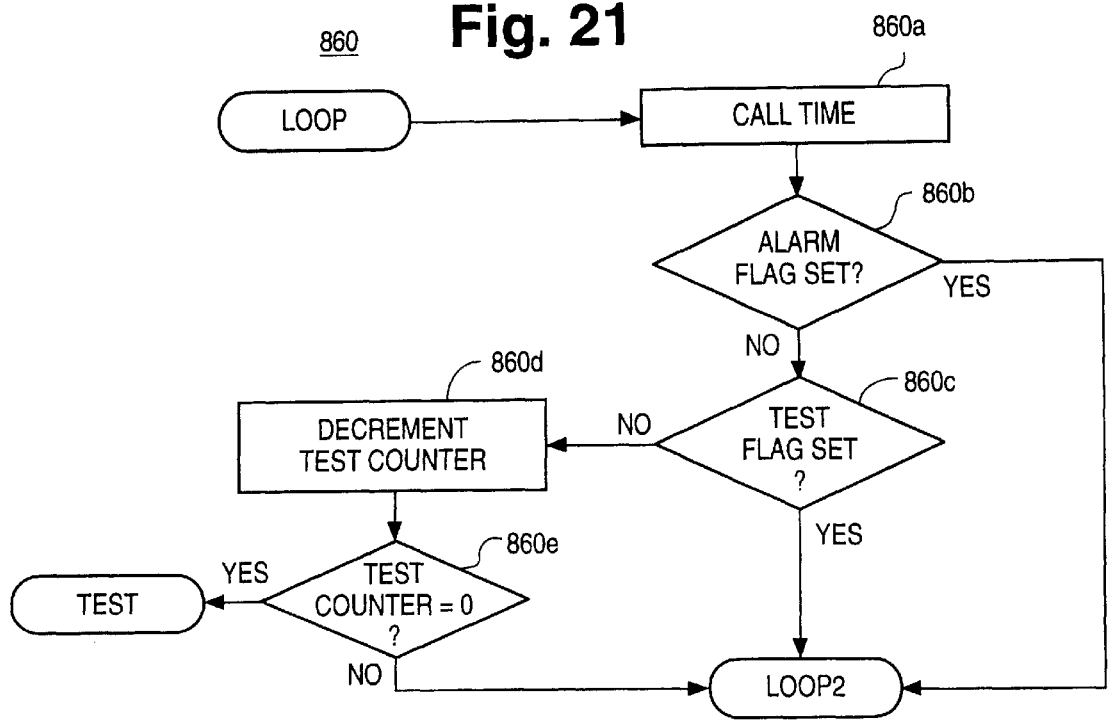
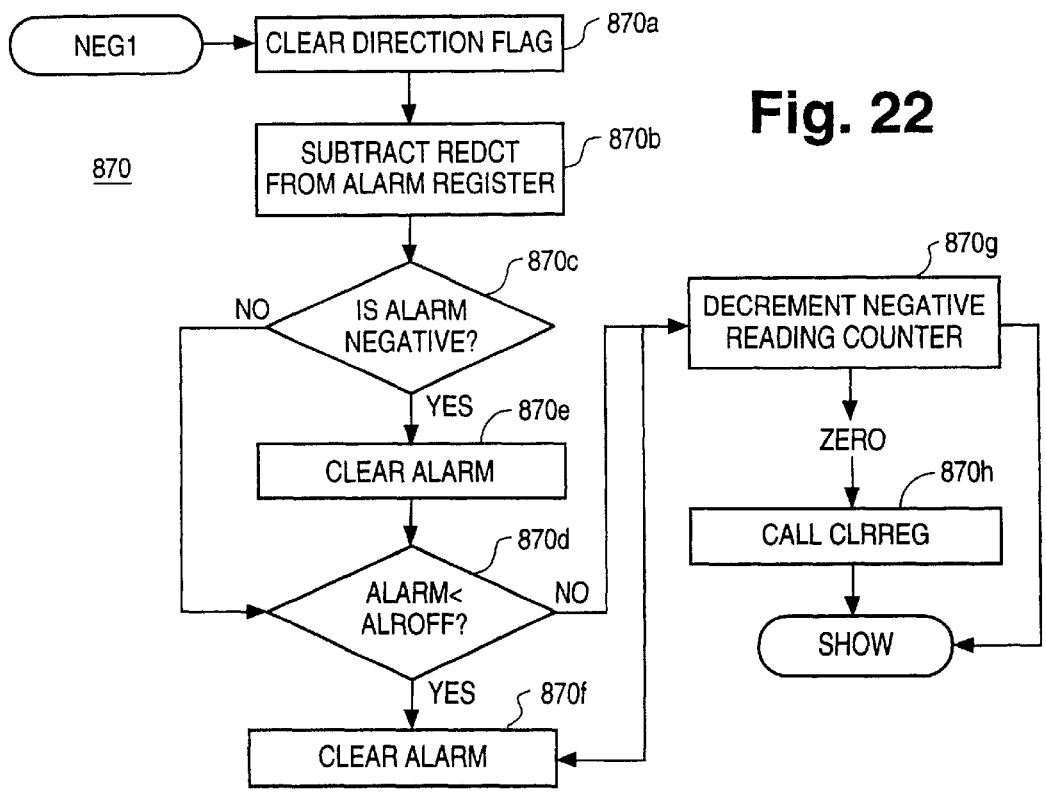

CARBON MONOXIDE AND SMOKE DETECTION APPARATUS

RELATED APPLICATION

This application is a continuation-in-part of provisional application Serial No. 60/055,009, filed on Aug. 7, 1997.

FIELD OF THE INVENTION

The present invention relates generally to detecting a condition in the environment. Particularly, the invention pertains to apparatus and methods to detect the presence of carbon monoxide and smoke in the atmosphere.

BACKGROUND

The threat of carbon monoxide poisoning has increased dramatically in the past decade. Carbon monoxide is a colorless, odorless, tasteless gas, making it virtually impossible to detect its presence. Carbon monoxide can be produced by various fuel burning appliances, such as, fuel fired furnaces, gas hot water heaters, gas stoves, gas dryers, space heaters, charcoal grills, fireplaces, vehicles, lawn mowers, or snow blowers. Once present, this gas circulates freely throughout a building, such as a home. If this gas is not ventilated properly, carbon monoxide poisoning may result.

Carbon monoxide inhibits the blood's ability to carry oxygen to body tissue, including vital organs such as the heart and brain. When carbon monoxide is inhaled, it combines with oxygen-carrying hemoglobin of the blood to form carboxyhemoglobin. Once combined with the hemoglobin, the hemoglobin is no longer available for transporting oxygen. The amount of carboxyhemoglobin that builds up is a factor of the concentration of the gas being inhaled and the duration of the exposure.

Carbon monoxide can act in the body in high concentrations, or slowly over a long period of time. Because it takes several hours to remove carbon monoxide from the body of a person, concentrations of carbon monoxide can gradually build up in the blood causing headaches, fatigue, dizziness, nausea, burning eyes, or unconsciousness.

Devices for sensing carbon monoxide and triggering an alarm in the presence of excess concentrations of carbon monoxide are presently available. These CO detectors typically employ a solid state sensor which purges itself and resamples for carbon monoxide on a periodic basis. However, conventional carbon monoxide detectors usually do not account for low levels of the carbon monoxide gas over long periods of time. Known detectors of this type are intended to be plunged into AC receptacles and are not battery powered.

Other types of known CO detectors utilize biomimetic sensors. Such devices are battery powered and detect changes in opacity of the biomimetic material.

In addition to being generated by operation of various products, carbon monoxide is produced along with smoke by fire. Fire detectors operate on different principles than do carbon monoxide detectors. Known fire detectors respond to heat, flame or smoke.

The range of presently available products includes separate carbon monoxide and fire detectors. It would be useful if the sensing characteristics of these separate units could be incorporated into a single, easy to use, easily installed, multi-mode product.

SUMMARY OF THE INVENTION

In view of the above, the present invention provides methods and apparatus for monitoring the presence and changes in the concentration of carbon monoxide. A detector that embodies the invention may also detect the presence of smoke.

In one aspect, a combined smoke and CO detector is battery operated. The detector carries a carbon monoxide sensor that is sealed until it is to be used by a consumer.

The CO sensor is carried within a housing and is not user replaceable. Removable tape seals the CO sensor until the detector is put into service. The sealing tape is applied when the carbon monoxide sensor is assembled. When a user places the detector into service the tape is removed thereby exposing the CO sensor to the ambient air.

An ionization-type smoke sensor is also carried within the housing. Both sensors are coupled to a programmed processor. The detector is energized by a single replaceable battery.

The process, in response to signals from the sensors, can produce an audible alarm indicative of the presence of carbon monoxide. A different audible alarm, for example in accordance with NFPA standard No. 72, can be produced to indicate the presence of smoke. In one aspect, if both carbon monoxide and smoke are present, the processor can go immediately unto a fire alarm indicating state.

In yet another aspect, a test circuit can be provided. For example, activating the test button can test each sensor sequentially. In this instance, appropriate audible alarms can be alternately produced.

In one aspect, a smoke determination can be made independently of a CO determination. The smoke determination can predominate and force the generation of visible and audible alarms.

Visual indicators of an alarm condition provide visual feedback to users. In one aspect, a symbol indicates if smoke is present and can be illuminated in the presence of detected levels thereof. Similarly, in the presence of pre-selected levels of carbon monoxide, a visual symbol indicative thereof can be illuminated. The visual indicators can be sequentially illuminated during a test sequence.

In yet another aspect, the detector and both of the sensors can be energized by a single battery. For example, a removable battery door can be provided. If the door is mounted in a user accessible side of the detector it will be possible to replace the battery with removing the detector from its mounted location.

The detector periodically measures the output of a CO sensor. The detector subtracts each sampled CO sensor output from the previous sampled sensor output. The difference of between the successive sampled sensor outputs are summed. The detector unit determines the rate of change of the sampled sensor outputs to determine the level of CO in the atmosphere. The detector can actuate an alarm when a predetermined CO condition is detected.

The methods and applications of the present invention provide a highly efficient and low cost detector that is capable of detecting the presence of carbon monoxide at an early stage to allow persons to evacuate the area. The detector can also detect low concentrations of carbon monoxide over long periods of time. The detector unit may also detect the presence of smoke.

The invention, together with further attendant advantages, will best be understood by reference to the following detailed description of the presently preferred embodiments of the invention, taken in conjunction with the accompanying drawings. It is to be understood that both the foregoing general description and the following detailed description are exemplary and explanatory and are intended to provide further explanation of the invention as claimed.

BRIEF DESCRIPTION OF THE DRAWINGS

FIG. 1 is a block diagram of a combined carbon monoxide and smoke detector;

FIG. 2a-1 and 2a-2 taken together are a flow diagram of a main routine of the detector of FIG. 1;

FIG. 19 is a flow diagram of an ACR1 sub-routine of the main routine of FIG. 16;

FIG. 20 is a flow diagram of a RESET sub-routine and a RESET1 sub-routine of the main routine of FIG. 16;

FIG. 21 is a flow diagram of a LOOP sub-routine of the main routine of FIG. 16;

FIG. 22 is a flow diagram of a NEG1 sub-routine of the main routine of FIG. 16;

Figure 16:
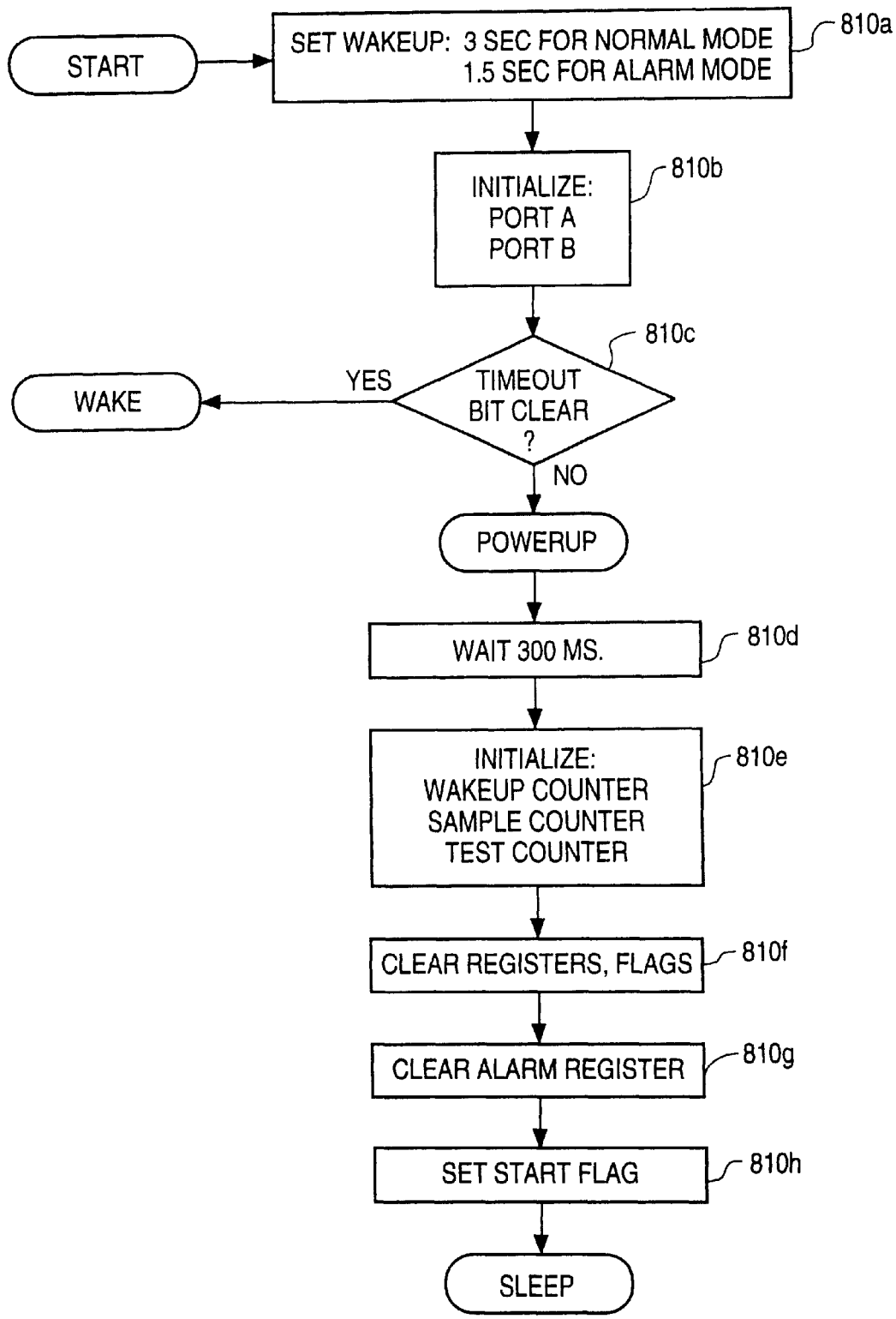
FIG. 16 is a flow diagram of a main routine of the detector of FIG. 13.
Figure 34:
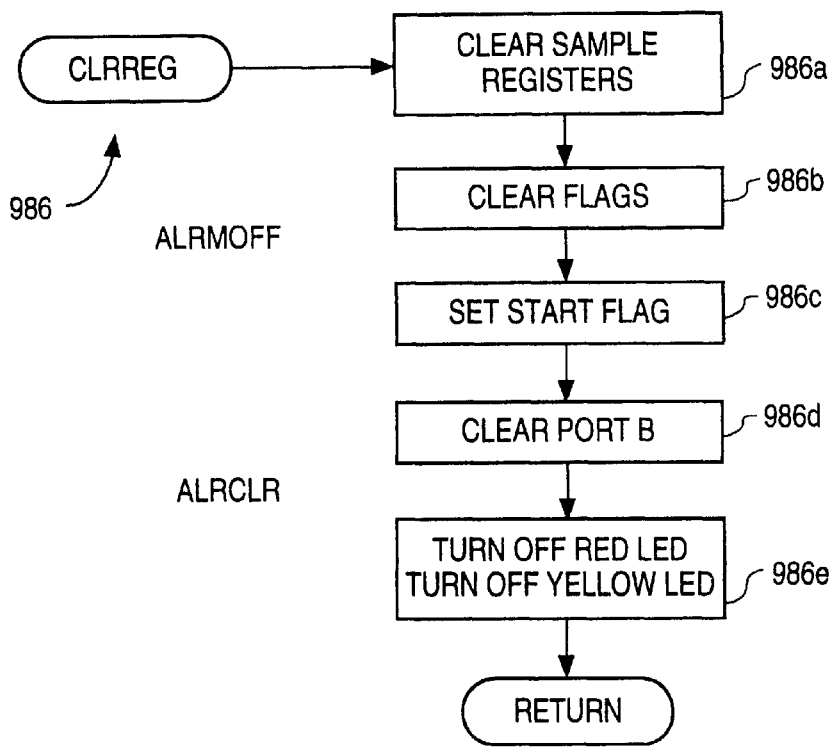
Figure 35:
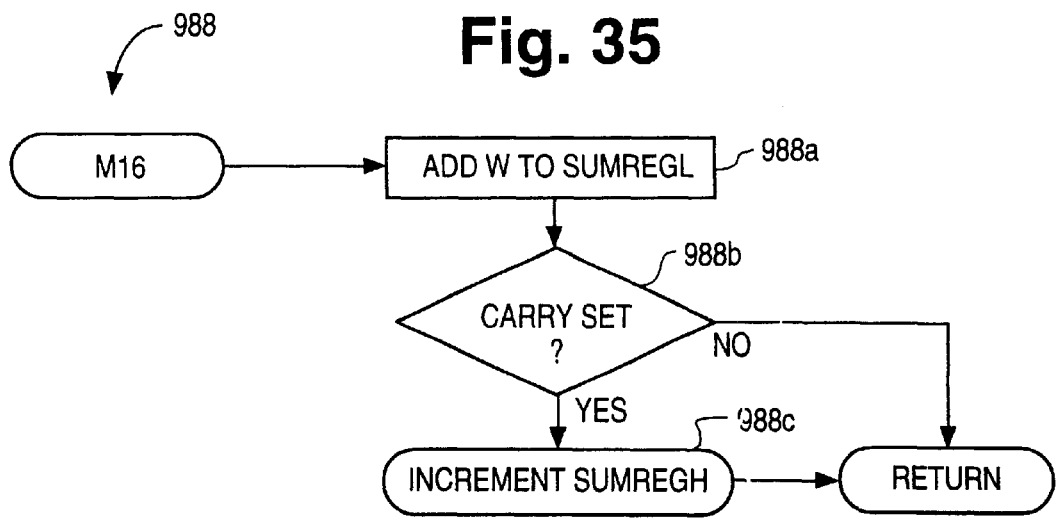

of the main routine of FIG. 16;

FIG. 34 is a flow diagram of a CLRREG sub-routine of the main routine of FIG. 16; and FIG. 35 is a flow diagram of a M16 sub-routine of the main routine of FIG. 16.

DETAILED DESCRIPTION OF THE PREFERRED EMBODIMENTS

Before explaining the present embodiments in detail, it should be noted that the invention is not limited in its application or use to the details of construction and arrangement of parts illustrated in the accompanying drawings and description, because the illustrative embodiments may be implemented or incorporated in other embodiments, variations and modifications, and may be practiced or carried out in various ways. Furthermore, unless otherwise indicated, the terms and expressions employed herein have been chosen for the purpose of describing the illustrative embodiments for the convenience of the reader and are not for the purpose of limitation.

Figures 1, 2A:
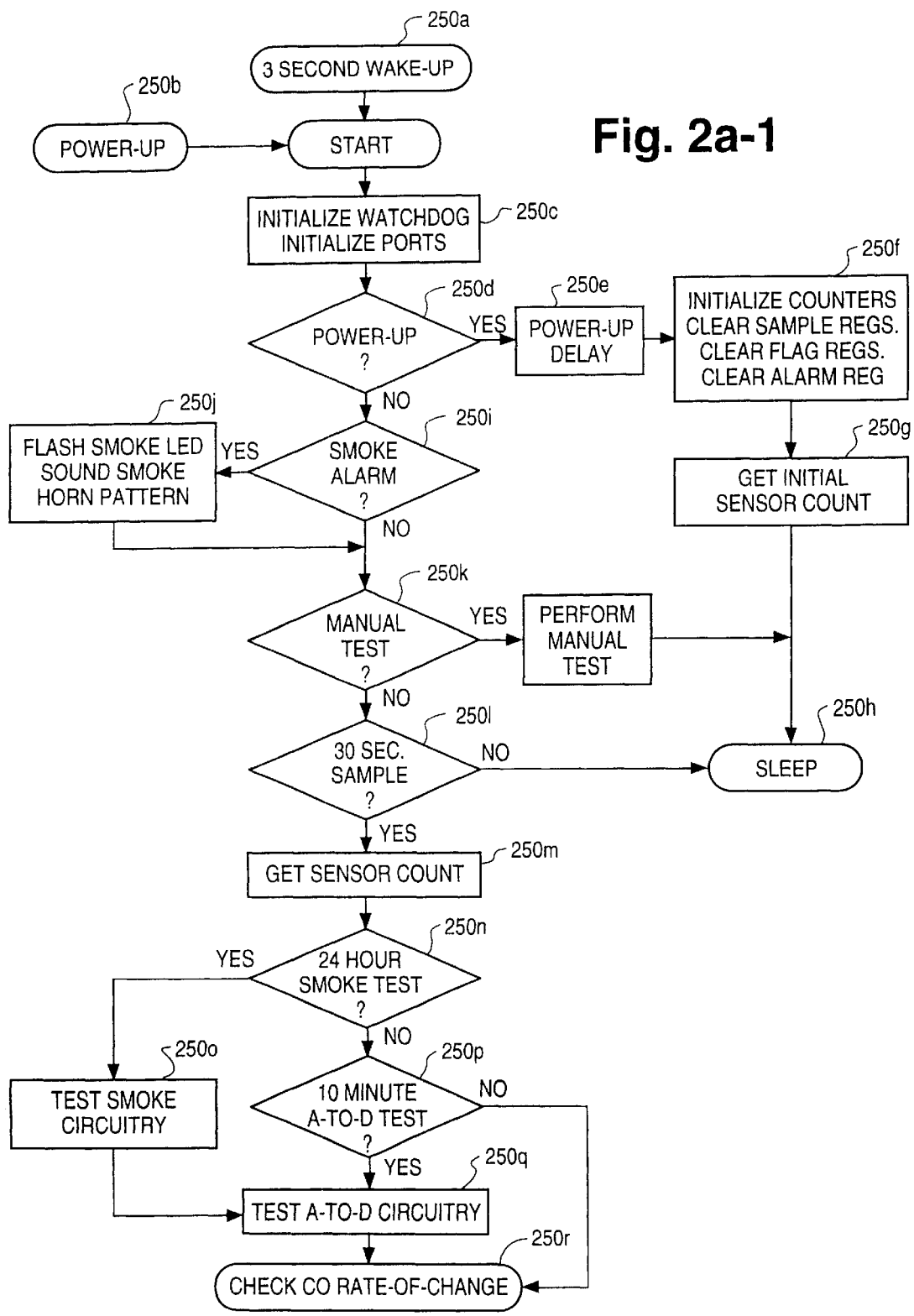

Referring now to the drawings and particularly to FIG. 1, a block diagram of a preferred embodiment of a detector 50 is illustrated. The detector 50 is a battery powered, single station, self-contained smoke and carbon monoxide alarm detector. The detector 50 detects the presence and concentration of carbon monoxide in the atmosphere and provides a warning to indicate a hazardous condition of carbon monoxide. The detector 50 also detects the presence of smoke in the air and provides a warning to indicate the presence of smoke.

As shown in FIG. 1, the detector unit 50 includes a housing 50a, control circuitry 100, an ionization sensing chamber, electronic measurement and control circuitry 110, audible and visual indicators, power circuitry, test/silence circuitry, temperature compensation circuitry, reset circuitry, low voltage detection circuitry, test switch/hush circuitry, output circuitry, interconnect circuitry and oscillator circuitry. Although it is shown as being constructed with various types of independent and separate units or devices, the detector 50 may be implemented utilizing one or more integrated or logic circuits, or a microprocessor which may be programmed to execute the operations or functions equivalent to those performed by the circuitry units shown. It is also contemplated that the detector can be carried out with any suitable hardware components and circuitry designs, computer programming, or a combination thereof.

Figure 1A:
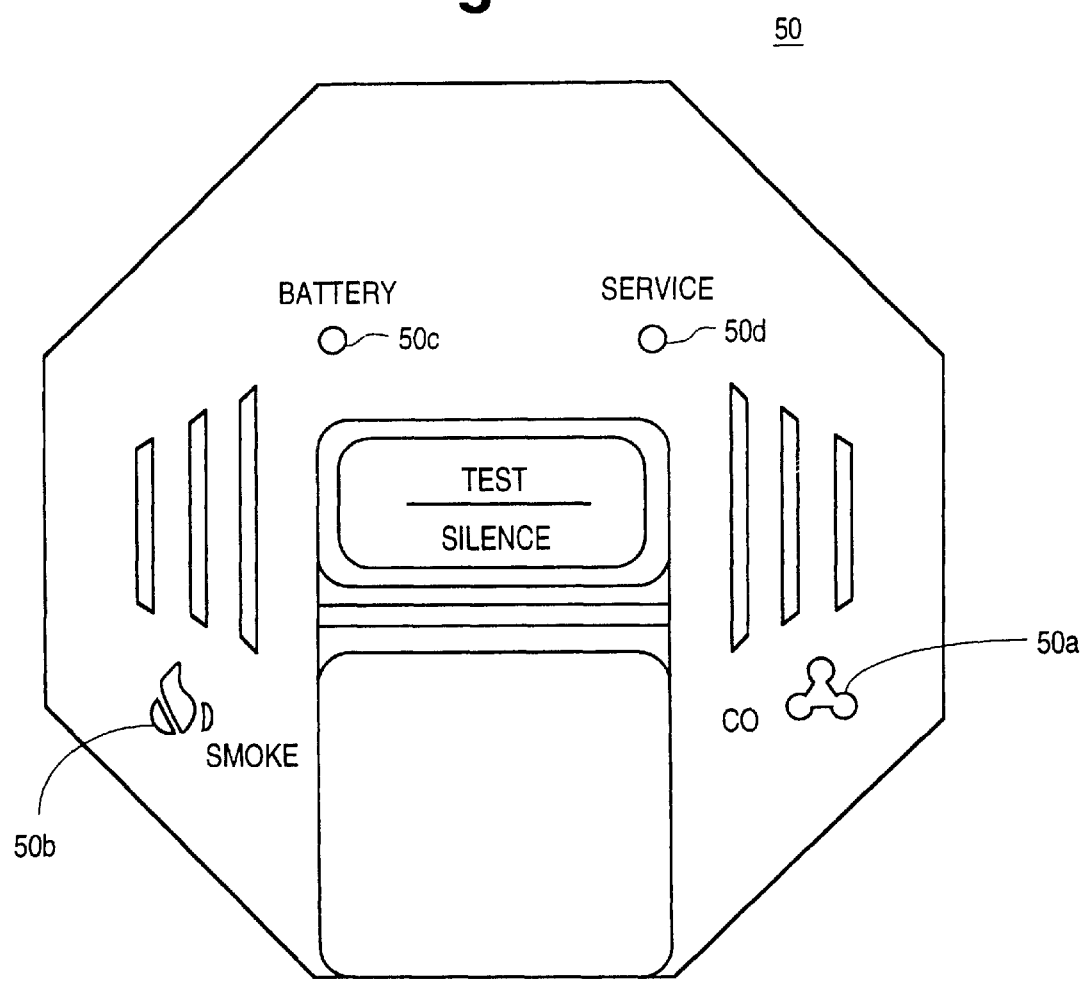
FIG. 1a is a plan view of the detector.

FIG. 1a shows a front plan view of the housing of the detector unit 50. The housing includes a CO alarm indicator 50a, a smoke alarm indicator 50b, a low battery indicator 50c, and a service status visual indicator 50d. The housing also preferably includes a single test/silence button as further illustrated below.

Figures 2, 2A:
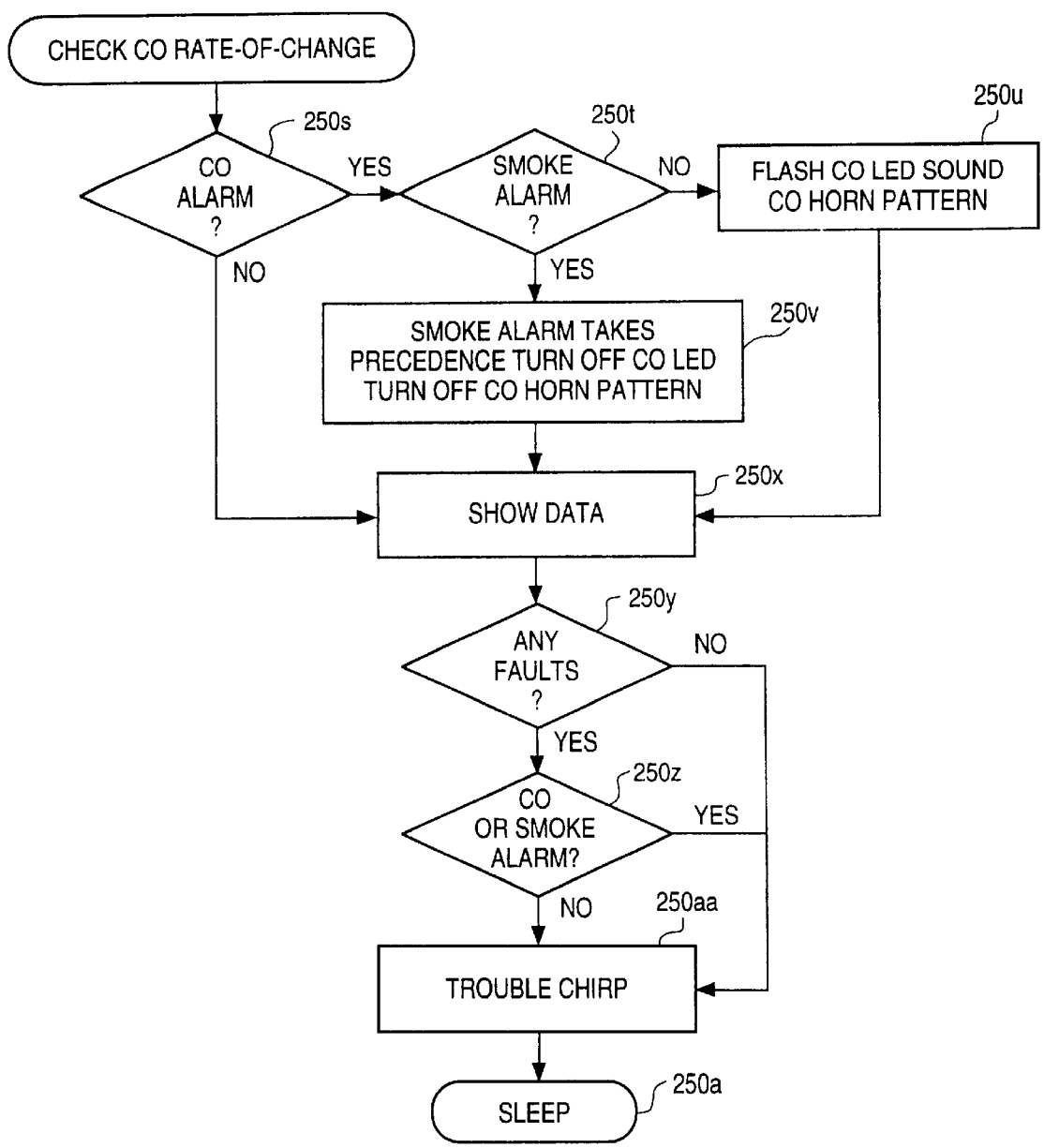
Figure 2:
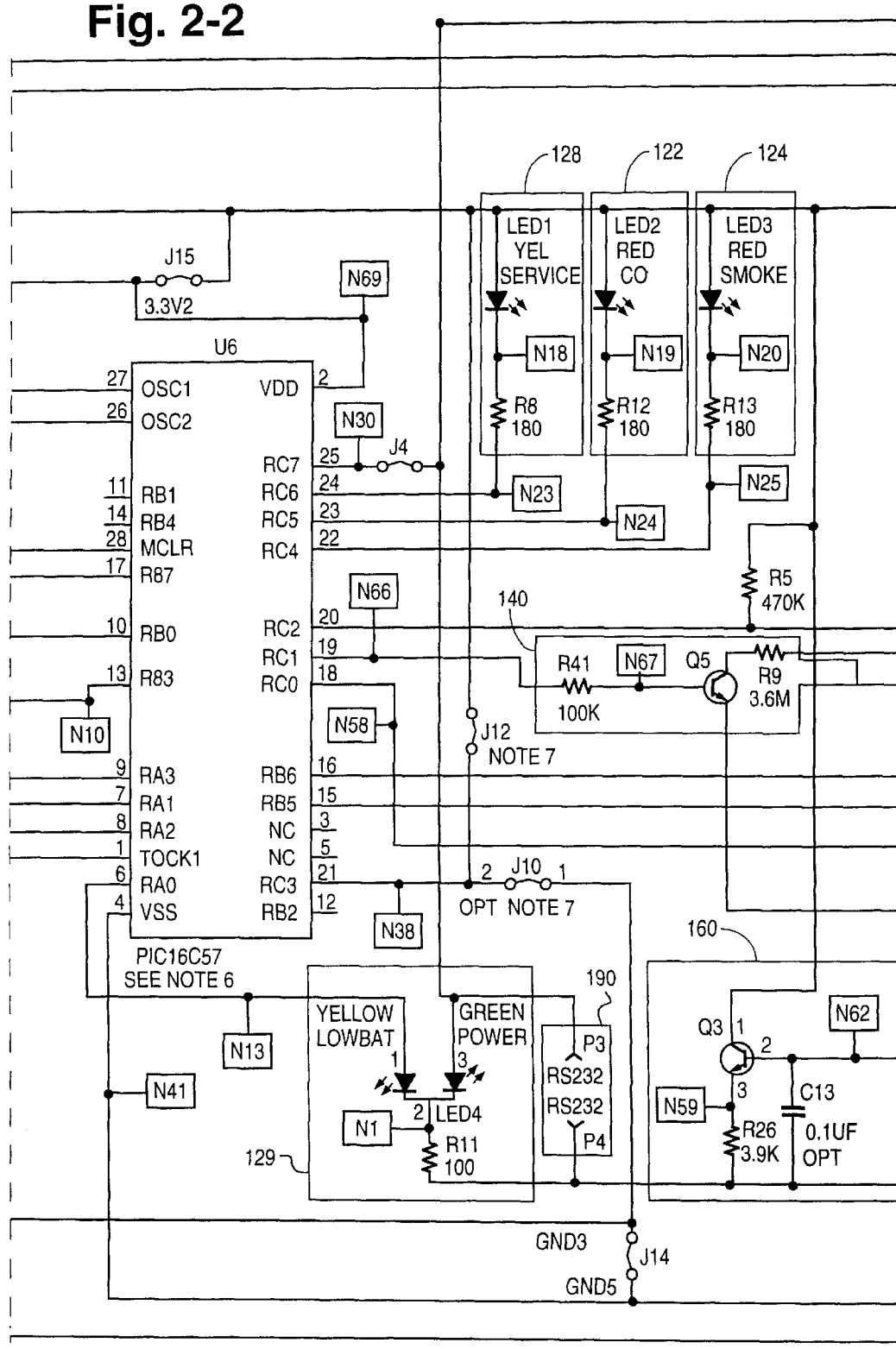
FIG. 2 is block diagram illustrating arrangement of FIGS. 2-1 . . . 2-4 which taken together are a schematic diagram of the detector of FIG. 1.

With respect to FIGS. 1 and 2, the control circuitry 100 of the detector 50 includes a processing unit 102. As shown in FIG. 2, the processing unit 102 includes a Microchip PIC16C57, available from microchip. The processing unit 102 preferably has a 2 MHz internal clock, Read Only Memory (ROM), Random Access Memory (RAM), and a plurality of input/output (I/O) pins. The processing unit 102 controls the overall operation of the detector unit 50 and processes information to determine a hazardous condition of carbon monoxide or smoke in the atmosphere. It will be understood that a variety of processing units or processors could be used without departing from the spirit and scope of the present invention.

The processing unit 102 preferably spends most of its time in a "sleep" mode in order to save power. While the processing unit 102 is in the "sleep" mode, the detector 50 typically consumes about 5 $\mu A$ of current. In the sleep mode, the internal clock of the processing unit 102 is disabled and the program counter is stopped.

The processing unit 102 can be "awakened" either by an external low level signal on pin 28 of the processing unit 102 or an internal reset initiated by an on-board watchdog timer. The watch dog timer is preferably used as an operational cycle clock to awaken the processing unit 102 about every 3 seconds to increment a time counter which requires about 2 $\mu A$.

The processing unit 102 takes sensor samples about every 30 seconds, battery and built-in tests occur about every 10 minutes. In order to limit the current drain of the detector unit 50 below 15 $\mu A$, the current used for sensor sampling cycle (which occurs once about every 30 seconds for approximately 25 ms) is usually kept to an average of about 5–6 $\mu A$. Unless the detector unit 50 is taking a sensor sample, checking the battery, performing a built-in test, or performing a user-initiated push-button test, the processing unit 102 will usually not be turned on for more than 25 ms before the processing unit 102 is put back to sleep.

The electronic measurement circuitry 110 preferably includes carbon monoxide detection circuitry 112, smoke detection circuitry 114, and smoke calibration circuitry 116. The carbon monoxide detection circuitry 112 monitors the presence or absence of carbon monoxide. When initially assembled a gas input port of the sensor 112 is covered by a removable protective tape 112a to prevent contamination. The tape 112a is removed by the user when the detector 50 is first activated.

As shown in FIG. 2, the carbon monoxide detection circuitry 112 includes resistors R16, R17, R33, and R34, a capacitor C5, a transistor Q2, and a biomimetic sensor S1. Preferably, the resistors R16, R17, R33 and R34, are about 100 $\Omega$, 330 $K\Omega$, 3.3 $K\Omega$ and 1 $K\Omega$, respectively, and the capacitor C5 is preferably about 0.022 $\mu F$.

The sensor S1 of the carbon monoxide detection circuitry 112 is utilized to detect the presence or absence of carbon monoxide in the surrounding atmosphere. The sensor S1 includes an infrared IR LED, a sensing device and a photo diode. The sensing device S1 is preferably a passive component that requires no additional power for its operation. The sensor S1 is preferably a S30 model, manufactured by Quantum Group.

Temperature compensation circuitry or resistor/thermistor network 150 drives the IR LED of the sensor S1 and acts as a constant current source, eliminating variations in the light output of the sensor S1 which might otherwise be imparted by changes in the battery voltage. The temperature compensation or circuitry 150 preferably includes resistors R18 and R20 and thermistor TH1. The resistors R18 and R20 are each preferably about 33 $\Omega$. When the ambient temperature varies, changes in the impedance of the thermistor TH1 adjusts the current supplied to the IR LED of the sensor S1, stabilizing the light out Pct, The light emitted (940 nm) by the IR LED is passed through the sensor and detected by the photo diode to provide a measure of the absorbency of the sensor. Because the sensor darkens when exposed to carbon monoxide, increased absorbency of the light energy of the LED can be utilized to detect the presence of carbon monoxide in localized atmospheric environments, such as, for example, inside homes, offices, etc. As carbon monoxide molecules are absorbed by the sensor, the sensor becomes more opaque. In the absence of the carbon monoxide in the atmosphere, the sensor releases previously absorbed molecules (if any present) becoming more transparent in the process.

The photo diode of the sensor S1, the capacitor C5, the resistor R16, and the processing unit 102 comprise a pseudo analog-to-digital (A/D) converter capable of measuring the absorbency of the sensor S1 with precision. The processing unit 102 receives and processes data on pin 9 supplied by the A/D conversion to determine the level of carbon monoxide present in the surrounding atmosphere. The pseudo A/D process measures the time needed to charge the capacitor C5 when the IR LED of the sensor S1 is enabled.

Initially, before the IR LED is enabled, any residual charge on the capacitor C5 is discharged to ground through the resistor R16 to pin 8 of the processing unit 102. Pin 8 of the processing unit 102 is then configured as a high impedance state input. The IR LED of the sensor device S1 is enabled through pin 13 of the processing unit 102 and a software timer in the processing unit 102 is started.

The processing unit 102 supplies a constant bias voltage level to the photo diode of the sensor S1. The voltage level is nearly the full value of the power supply voltage $V_{cc}$ since, even at the highest level of photo diode current, the voltage drop internal to the processing unit 102 (from supply pin 14 of the processing unit 102 to the output on pin 2) is minimal.

Because the charging current induced in the photo diode PD is nearly constant (over relatively short sampling intervals), the voltage on the capacitor C5 rises linearly over time. When the ramping voltage of the capacitor reaches about 0.85 Vcc, the software timer is terminated and a sampling time (ST) count is thereby obtained.

The absorbency of the sensor is sampled once about every 30 seconds. Each time the sensor absorbency is sampled, the sampling time value is compared with predetermined or programmable limits.

If the sensor is too light or too dark or sample time is too short or too long, a FAULT routine, as further described below, is initiated by the detector unit 50. Otherwise, the current value of the sample is compared with the value from the previous sample measurement, and the difference is stored in one of a plurality of storage registers. Subsequently, the storage registers are summed, and the value is placed in a sum register and also added to an alarm register.

The discrete sampling time values of the sensor S1 are measured over time by an the processor 102 as further described below. Since the light output for the LED of the sensor S1 is virtually constant over time, temperature, and voltage, the only mechanism by which the sampling time can change is relative absorbency of the sensor S1. When the concentration of carbon monoxide in the atmosphere surrounding the sensor increases, the sensor darkens and iterative sample times measured by the A/D converter lengthen or increase.

The sample time rate-of-change (dST/dt), is monitored by the processing unit 102, and its magnitude is used to trigger an "alarm" condition (i.e., a high level alarm) when the carbon monoxide levels present a hazardous condition. The sensor S1 also responds to various carbon monoxide concentrations in the manner consistent with the ULTO34 standard.

A status flag (i.e., ALARM FLAG) is set when the value in the alarm register reaches full scale (i.e., 255 decibel). At this time a high level alarm is issued. When the carbon monoxide drops below about 50 ppm, the sensor begins to lighten and the values in the sum register become negative, causing a reduction in the value stored in the alarm register. If the value in the alarm register falls to about 48 or below, the sample, flag, and alarm registers in the high level alarm will be cleared, and the detector unit 50 will resume normal operation.

The A/D converter operation of the carbon monoxide detection circuitry 112 is verified by the processing unit 102 on power-up and about every 10 minutes thereafter (i.e., about every 20 sensor sampling cycles). The integrating capacitor C5 of the carbon monoxide detection circuitry 112 is discharged, and then allowed to charge by current supplied by pin 6 of the processing unit 102 through the A/D test resistor R17.

The software timer of the processing unit 102 executes a sample time measurements and the resultant value has to lie within program limits. This test checks for excessive leakage, shorting, or improper operation of the A/D measurement components. Any failure sets a fault flag and a fault condition is annunciated to notify the user.

The smoke detection circuitry 114 of the electronic measurement circuitry 110 detects the presence of smoke in the atmosphere. The smoke detection circuitry provides a signal to the processing unit 50 that generates a warning signal.

As shown in FIG. 2, the smoke detection circuitry 114 preferably includes a smoke detector D1, a smoke comparator unit U2, capacitors C3, C10, and C14, and resistors R2, R3, R4, R5, R28, and R30. The smoke comparator unit U2 is preferably a comparator such as Model No. SC41411PK available from Motorola (comparable to MC14467). The capacitors C3, C10, and C14 are each preferably about 0.1 $\mu$F, and the resistors R2, R3, R4, R5, R28, and R30 are preferably about 1.5 M$\Omega$, 8.2 K$\Omega$, 1.5 K$\Omega$, 470 K$\Omega$, 1 M$\Omega$, and 33 $\Omega$, respectively.

The smoke detector D1 preferably includes a single source dual ionization chamber C1 having an active chamber C1, a sensing electrode E1, and an ion chamber I1. A 1.0 $\mu$Ci maximum source of American 241 is employed in the ionization chamber.

The active chamber C1 is connected to ground by the parallel combination of the resistor R28 and the capacitor C10. The capacitor C10 provides transient protection for the active chamber C1, and the resistor R28 allows the active chamber C1 of the smoke detector D1 to be raised above ground by pin 18 of the processing unit 1d SW3 are closed, 3.3 volts is applied by pin 18 of the processing unit 102 to the resistor R28 to simulate about 40–50 pA MIC.

The sensing electrode E1 of the smoke detector D1 is connected to the non-inverting input (pin 15) of the smoke comparator unit U2. The connection of the sensing electrode, a very high impedance point, to the non-inventing input is preferably a flying connection to minimize leakage effects due to the presence of a printed circuit board.

Pins 14 and 16 of the smoke comparator unit U2 are connected together internally to a voltage follower of a non-inventing input of the smoke comparator unit U2 to provide an active guard output. This active guard reduces the effect of leakage between non-inventing input of the smoke comparator unit U2 and adjacent pins.

An alarm feedback pin (pin 1) of the smoke comparator unit U2 is monitored by the processing unit 102 to determine if a smoke condition exists. The feedback pin is preferably pulled to about 3.3 volts by a pull-up resistor R5 in a clean air condition. When smoke is present, the voltage. across the dual chamber decreases and the voltage at the sensing electrode E1 increases.

The alarm feedback pin of the smoke comparator unit U2 will change to a low level state which is then read by the processing unit 102. The processing unit 102 will then go into a smoke alarm mode and turn on a smoke horn. The horn pattern consists of an active phase lasting about 0.5 seconds +/− 10% followed by an off-phase lasting about 0.5 seconds +/− 10%, for three successive active periods, which are then followed by an off-phase lasting about 1.5 seconds +/−10%. This pattern is comparable to that specified by NFPA 72 . Other patterns can be stored in the processor to use as needed.

The circuitry 114 establishes, using an alarm threshold established thereby, if enough smoke is present to warrant generating a smoke alarm. If so, the two state smoke alarm output signal goes from a high to a low which is indicative of a smoke alarm state. The processor 102 will in turn activate the visible and audible smoke alarms. This is completely independent of processing for the presence of CO.

The smoke calibration circuit 116 of the electronic measurement circuitry 110 preferably includes resistors R14, R32, and R36. The resistors R14, R32, and R36 are preferably 1 M$\Omega$, 1 M$\Omega$, and 1.5 M$\Omega$. The resistors R14, R32, and R36 preferably form a resistive divider to provide a reference voltage for the inverting input (pin 13) of the smoke comparator unit U2. The voltage division at the inverting input is designed so that under clean air conditions the two inputs are different to provide a nominal sensitivity of 67 pA MIC and that no alarm results.

On power-up of the detector 50, and about every 24 hours thereafter, proper smoke detector operation is verified by the processing unit 102. Initially, the resistor R28 of the smoke calibration circuitry 116 is raised above circuit ground by pin 18 of the processing unit 102. As a result, the voltage across the dual chamber of the detector D1 is lowered and the voltage at the sensing electrode E1 is raised.

The processing unit 102 applies about 3.3 volts to the resistor R28 to simulate about 40–50 pA MIC. The processing unit 102 then monitors the output of the smoke comparator U2 about every 10 seconds or less. Any failure of the smoke comparator U2 sets the fault flag and a fault condition is annunciated to notify the user.

A manual test mode is also provided for by the detector unit 50. This test mode is activated by the user, who simply pushes a test/silence button on the face of the detector unit until a horn chirp is issued and a yellow service LED flashes. Once the test mode is entered, the processing unit 102 applies 3.3 volts to the resistor R28 of the smoke detection circuitry 114 to simulate about a 40–50 pA MIC. The processing unit 102 then monitors the output of the smoke comparator unit U2 Every 10 seconds or less until it is pulled low, which signifies a smoke condition. Any failure sets a fault flag and a fault condition is annunciated to notify the user, and the carbon monoxide test is terminated.

If the output of the smoke comparator unit U2 is at a low level state before timing out, the processing unit 102 will emit one cycle of the smoke alarm pattern. If the detector unit 50 passes, the processing unit 102 pauses for about one second to separate smoke and carbon monoxide tests. Then each green or yellow flash of a power LED depending on the battery status is preceded by a sensor sample cycle. Each of these samples is taken with pin 6 of the processing unit 102 configured as an input pulled to ground, stealing current through the resistor R33 of the carbon monoxide detection circuitry 112 which is normally supplied by pin 13 of the processing unit 102 to the base of transistor Q2. This activity "starves" the respective LED, reducing the light admitted through the sensor, and effectively simulates a carbon monoxide exposure, filling the alarm register with about 3 to 5 sample cycles. A successful manual test results in a self-induced high level alarm state which is enabled for two cycles of the alarm pattern (i.e., on for 1.5 seconds and off for 1.5 seconds) indicating that the detector unit 50 is operating properly.

The audio and visual indicators 120 of the detector 50 are used in conjunction with various self-tests and user-initiated tests to indicate when the detector unit 50 is operating normally or has a problem which requires service. The audio and visual indicators 120 also alert persons nearby when smoke and carbon monoxide concentrations are unhealthy or dangerous. The audio and visual indicators 120 include carbon monoxide alarm indicator circuitry 122, smoke alarm indicator circuitry 124, horn driving circuitry 126, service indicator circuitry 128, and power/low battery indicator circuitry 129.

The carbon monoxide alarm indicator circuitry 122 of the audio and visual indicators 120 preferably includes an indicator light LED2 and resistor R12. The light emitting diode LED2 is preferably a red light emitting diode (LED), and the resistor R12 is about 180 Ω. The carbon monoxide alarm indicator circuitry 112 is electrically coupled to pin 23 of the processing unit 102. The processing unit 102 activates the indicator light LED2 by pulling pin 23 to a low level state to provide a current path (typically, about 8 pA) from the power source through the indicator light LED2 and the current limiting resistor R12 to ground.

The smoke alarm indicator circuitry 124 of the audio and visual indicators 120 preferably includes an indicator. light LED3 and a resistor R13. The indicator light LED3 is preferably a red light emitting diode (LED), and the resistor R13 is about 180 Ω. The smoke alarm indicator circuitry 124 is electrically coupled to pin 22 of the processing unit 102. The processing unit 102 activates the indicator light LED3 by pulling pin 22 to a low level state to provide a current path (typically, about 8 pA) from the power source through the indicator light LED3 and current limiting resistor R13 to ground.

The horn driving circuitry 126 of the audio and visual indicators 120 preferably includes a power oscillator U4, a piezoelectric alarm H1, resistors R19, R25, R37 and R38, and transistor Q4. The power oscillator U4 is preferably a MC14049VBCP available from Motorola is a known type used with smoke detectors. The resistors R19, R25, R37, and R38 are preferably about 1.5 MΩ, 1.5 MΩ, 1 KΩ, and 1 KΩ, respectively, the capacitor C7 is preferably about 0.0022 $\mu$F.

The piezoelectric alarm H1 is driven by the power oscillator U4. Pin 2 of the piezoelectric alarm allows the power oscillator to resonate at a particular frequency, preferably within a range of about 3.5 kHz. In order to turn the piezoelectric alarm H1 on, the processing unit 102 sets output pin 11 to a high level state, putting the transistor Q4 into saturation, effectively connecting pin 8 of the power oscillator U4 directly to ground.

In operation, the detector unit 50 has a special alarm silencing function that can be initiated by the user to silence the alarm. This function is activated by pressing a test/silence button on the detector unit 50. When the detector is in a smoke alarm state, pressing the button will put the detector unit into a silence mode. This mode will silence the horn for about 8 minutes. During this time, the light indicator LED3 of the smoke alarm indicator circuitry 124 will remain on. Pressing the test/reset button again while in silence mode, will reset a silence interval timer.

When in silence mode, the processing unit 102 desensitizes the ion chamber I1 by turning on the transistor Q5 of the hush/test circuitry 130, pulling the ion chamber to ground. Increasing levels of smoke will kick the processing unit 102 out of hush mode and continue with a smoke alarm condition.

When the detector is in a high level carbon monoxide alarm state, pressing the test/reset button will silence the horn for about 4 minutes. However, the light indicator LED2 of the carbon monoxide indicator circuitry 122 will remain on. The high level carbon monoxide alarm can be silenced only one time.

The power circuitry 130 of the detector unit 50 provides power to the various components of the detector unit 50. The power circuitry 130 includes a power supply and filter circuitry 132, reverse bias protection circuitry 134, and voltage regulator and filter circuitry 136. The power supply and filter circuitry 132 preferably includes a 9 volt battery B1 and a capacitor C2. Preferably, the battery B1 supplies power (i.e., about 8.4 volts) to the smoke comparator unit U2 and other associated circuitry. The battery is preferably a 9 volt alkaline type and the capacitor C2 is about 0.1 $\mu$F.

The voltage regulator and filter circuitry 136 of the power circuitry 130 preferably includes a voltage regulator U1, and capacitors C8 and C9. The voltage regulator U1 supplies a regulated 3.3 VDC to the processing unit 102 and its associated circuitry. The 3.3 volt level minimizes overall current drain in the detector unit, which is typically about 5–7 $\mu$A. The voltage regulator U1 is preferably a Seiko S81233SG and the capacitors C8 and C9 are about 2.2 $\mu$F and 0.1 $\mu$F, respectively.

The reset circuitry 160 of the detector 50 insures proper reset of the processing unit 102 when the battery B1 is removed by discharging any capacitance on the output of voltage regulator U1. The reset circuit 160 of the detector unit 50 preferably includes resistors R26, R27, R31, and R40, a capacitor C13 and a transistor Q3. The resistors R26, R27, R31, and R40 are preferably about 3.9 KΩ, 10 MΩ, 33 KΩ, and 10 MΩ, respectively, the capacitor C13 is about 0.1 $\mu$F.

The reverse bias protection circuitry 134 of the power circuitry 130 provides protection for the circuitry of the detector unit 50 when the battery is installed improperly. The reverse bias protection circuitry 134 preferably includes a diode D5 and a resistor R35. The diode D5 of the reverse bias protection circuitry 134 prevents any damaging current flow through the voltage regulator U1 and the capacities C2, C8, and C9 if the battery is installed backwards. The resistor R35 is about 1 KΩ.

The resistor R35 of the reverse bias protection circuitry 134 limits current through a voltage detector U3 to a non-damaging level when the battery B1 is installed backwards, but is not large enough to substantially. effect the level of the battery voltage at the input (pin 2) of the voltage detector U3. The quiescent current drain through the voltage detector U3 is typically about 1 $\mu$A, creating a voltage drop across the resistor R32 of only about 0.001 $V_{dc}$.

About once every 10 minutes or every 20 operation cycles, the battery B1 is tested to insure it retains sufficient capacity to sustain operation after a low battery condition is detected as specified by UL2034 standards. During this test, the processing unit 102 enables the IR LED of the sensor S1 for 10 mS (which consumes about 20 mA) to load the battery for an accurate measurement.

Before turning the IR LED off, the processing unit 102 samples the state of pin 1 of the voltage detector U3. When the battery level under load exceeds 7.5 $V_{dc}$ (the trip point of the voltage detector U3), the resistor R23 pulls up the open collector output (pin 1) of the voltage detector U3 to 3.3 volts. As a result, a high logic level is detected by pin 16 of the processing unit 102, which indicates the presence of a sufficient battery level. On the other hand, if the battery level under load is less than 7.5 $V_{dc}$, the open collector output of the voltage detector U3 will be pulled to ground, causing pin 16 of the processing unit 102 to detect a low logic level. In this case, the processing unit 102 sets a LOW BATTERY flag and indicates this condition to the user.

FIGS. 2*a*-1, 2*a*-2 taken together illustrate as, a flow diagram a general overview of the operations carried out by the detector 50. As shown in FIG. 2*a*-1, after the detector 50 is awakened at block 250*a* or the detector 50 is powered up at block 250*b*, the detector 50 initializes a watchdog timer and initializes one or more ports at block 250*c*. At block 250*d*, the detector 50 determines whether it was just powered up.

If the detector 50 was just powered up, it sets a power-up delay at block 250*e*. At block 240*f*, the detector 50 initializes one or more counters, clears one or more sample registers, clears one or more flag registers, and clears the alarm register. The detector 50 then obtains an initial sensor count at block 250*g* and then goes into the sleep mode at block 250*h*.

If the detector 50 was not just powered up at block 250*d*, it will determine whether there is a smoke alarm condition a block 250*i* (based on a binary, low, output signal for comparator U2). If there is a smoke alarm condition, the detector 50 will flash the LED3 of the smoke indicator circuitry 124 and sound the smoke horn pattern at 250*j*. The process then proceeds to block 250*k* as further described below.

If a smoke alarm condition is not detected at block 250*i*, the detector 50 will determine whether a manual test has been initiated at block 250*k*. If a manual test has been initiated, the detector 50 will perform the manual test and then go into the sleep mode at block 250*h*.

If a manual test has not been initiated at block 250*k*, the detector 50 determines whether to perform a 30 second CO sample at block 250*l*. If the detector 50 does not have to obtain a 30 second sample, it will go into the sleep mode at block 250*h*.

If the detector 50 has to obtain a 30 second sample at block 250*l*, that sensor count is attained at block 250*m* and then the detector 50 determines whether to perform a 24 hour smoke test at block 250*n*. If a 24 hour smoke test is to be performed, the detector 50 tests the smoke alarm indicator circuitry 124. The process then proceeds to block 250*q* as further described below.

If a 24 hour smoke test is not to be performed at block 250*n*, the detector determines whether to perform a 10 minute A-to-D test at block 250*p*. If the detector 50 does not have to perform the 10 minute A-to-D test, the process proceeds to block 250*r* as further described below.

If the A-to-D test is to be performed at block 250*p*, the detector 50 tests the A-to-D circuitry at block 250*q*. The detector 50 then checks the carbon monoxide rate of change at block 250*r* and determines whether to activate the carbon monoxide alarm at block 250*s*. This determination is independent of the output of the smoke detector circuit U2.

If the carbon monoxide alarm detector is to be activated, the detector 50 will determine whether to also activate a smoke alarm at block 250*t*. If the smoke alarm is not to be activated, the detector 50 will flash the light indicator LED2 of the carbon monoxide alarm indicator circuitry 122 and sound th[0085] carbo[008e] monoxide horn pattern at block 250*u*.

If the smoke alarm is to be activated at block 250*t*, the detector 50 will turn off the light indicator LED2 and turn off the carbon monoxide horn pattern. The process will then proceed to block 250*x* as further described below.

If the carbon monoxide alarm is not to be activated at 250*s*, the detector 50 will turn off the light indicator LED3 of the carbon monoxide alarm indicator circuitry 122 and the carbon monoxide horn pattern at block 250*w*. At block 250*x*, the data will be examined and the detector 50 will determine whether there are any faults at block 250*y*.

If there are no faults, the detector unit 50 will go into the sleep mode at block 250*h*. If faults are detected at block 250*y*, the detector 50 will determine whether the carbon monoxide or smoke alarm has been activated at block 250*z*. If the carbon monoxide or smoke alarm is activated, the processing unit 102 will go into the sleep mode at block 250*h*. If the carbon monoxide or smoke alarm is not activated, the detector unit 50 will initiate a trouble chirp at block 250*aa* and then go into the sleep mode at block 250*h*.

Figures 2, 3:
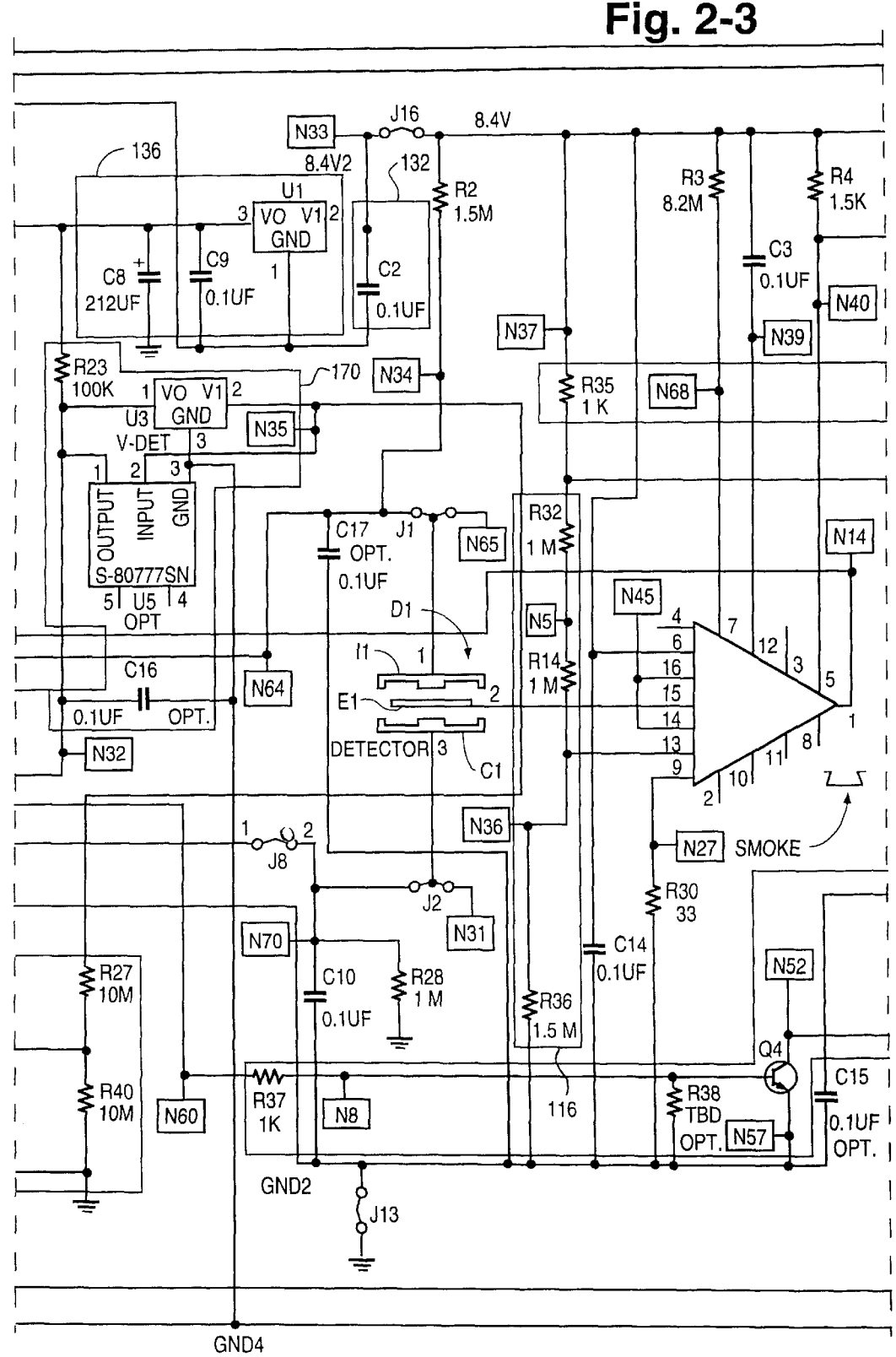
FIG. 3 is a flow diagram of a SUB-ROUTINE OF THE MAIN ROUTINE of FIGS. 2-a-1, -2.

FIGS. 3 through 12 illustrate detailed flow diagrams of the operations carried out by the detector 50. FIG. 3 illustrates a main routine 300 of the process carried out by the detector 50 to implement various tests, alarm conditions, and smoke and carbon monoxide checks. Initially, the detector unit 50 sets a wake-up tim[0085] at block 302. The detector. unit 50 sets the wake-up time at about 3 seconds for normal mode, about 1.5 seconds for alarm mode, and about 0.75 seconds for test mode. The detector unit 50 then initializes ports A–C at block 304 and then determines whether a TIME OUT bit has been cleared at block 306. If the TIME OUT bit has been cleared, the process proceeds to the WAKE sub-routine as further described below.

If the TIME OUT bit has not been cleared at block 306, the detector 50 determines whether a POWER DOWN bit has been set at block 312. If the POWER DOWN bit has not been set, the process proceeds to a POWER UP routine as further described below. If the POWER DOWN bit is set at block 312, the detector unit 50 increments a SPECIAL TEST counter at block 314, and then determines whether the SPECIAL TEST counter is greater than 2 at block 316. If the SPECIAL TEST counter is greater than 2, the process proceeds to the WAKE sub-routine. If the SPECIAL TEST counter is not greater than 2 at block 324, the detector unit 50 initializes a TEST counter, sets a START flag at block 318, and then proceeds to a LOOP sub-routine as further described below.

Figures 2, 3, 4:
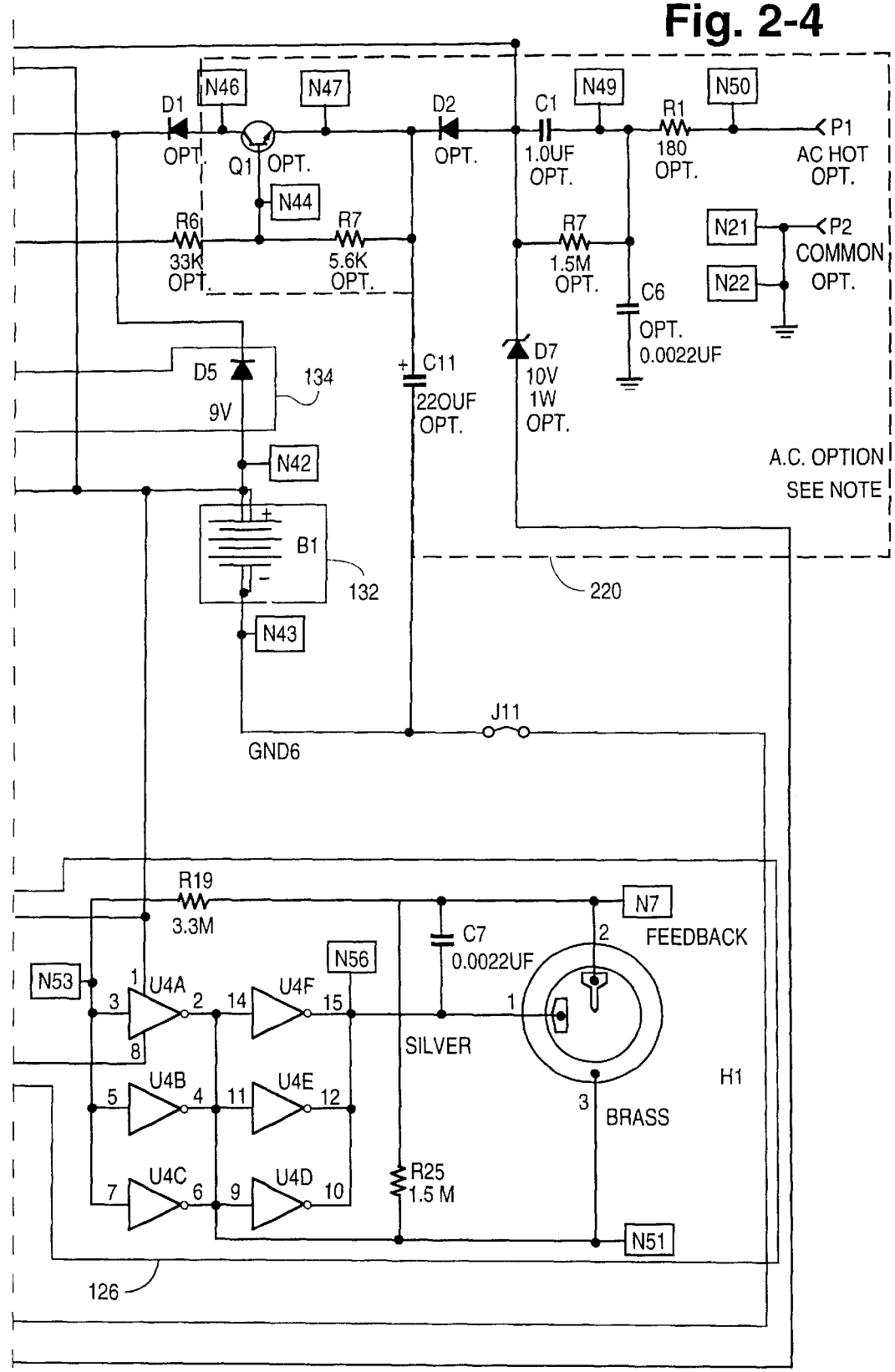
FIG. 4 is a flow diagram of a POWER-UP sub-routine of the main routine of FIG. 2a-1, -2.
Figure 3:
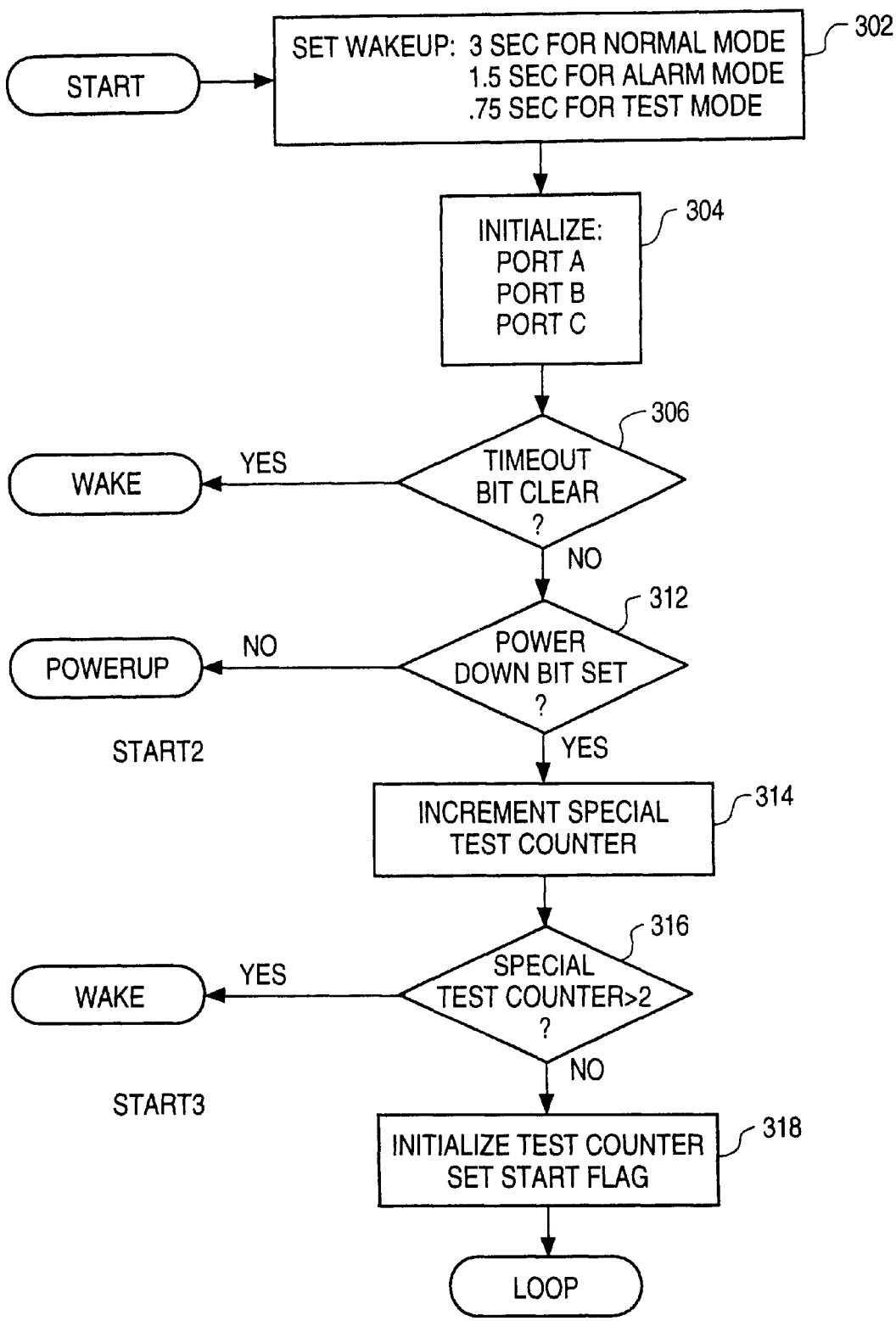

FIG. 4 illustrates a POWERUP sub-routine 320. When the detector 50 is initially turned on, the POWERUP sub-routine initializes various counters, registers, and flags. At block 320*a* the detector 50 initializes a WAKE UP counter, a SAMPLE counter, and a TEST counter. The detector 50 then clears the registers and flags and sets a START flag a block 320*b*. The detector 50 then waits about 255 ms at block 320*c* and sets the ALARM TOGGLE counter CTR equal to 4 at block 320*d*. The detector 50 clears the ALARM register at block 320*e* and then it goes into the sleep mode.

Figure 5:
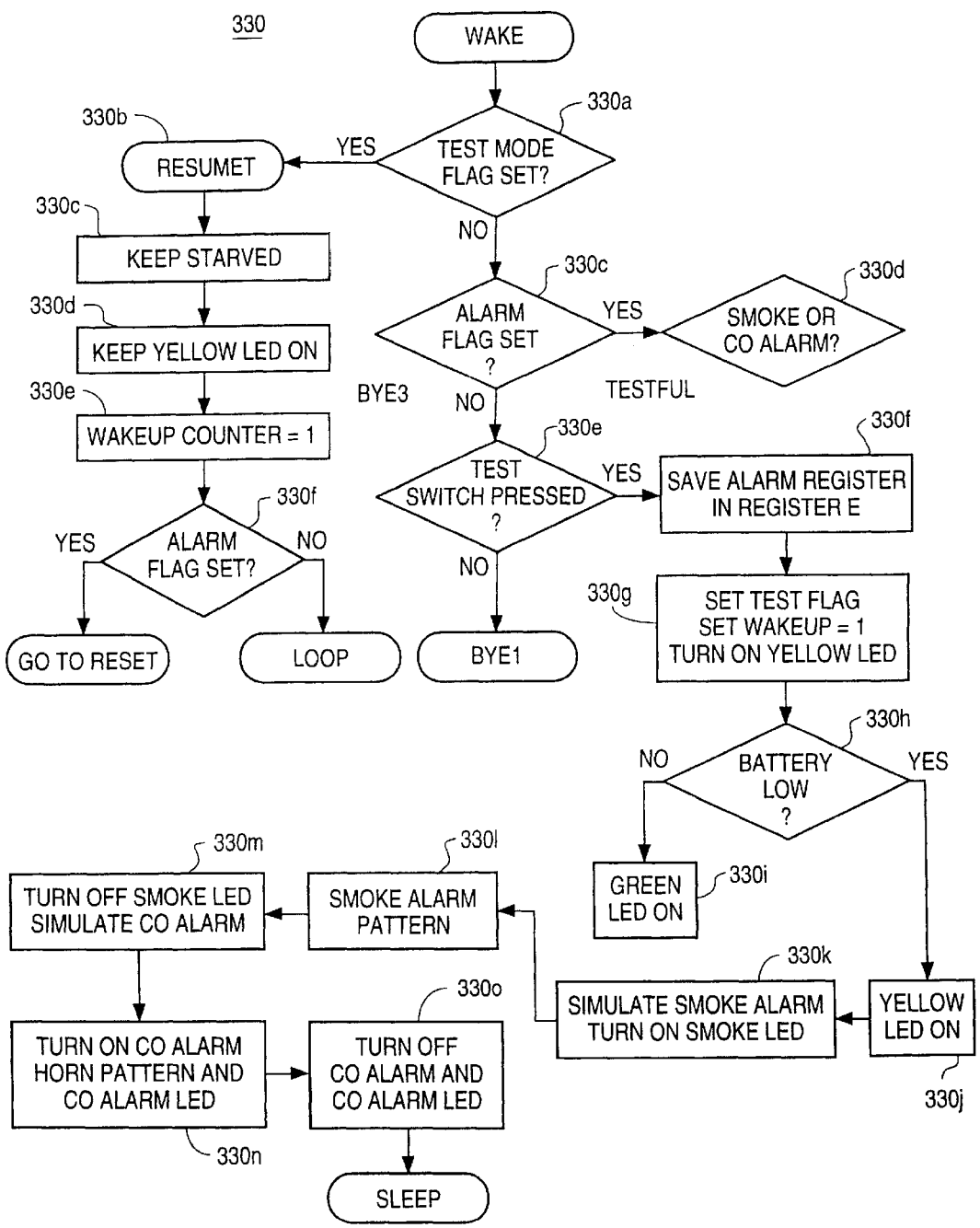
FIG. 5 is a flow diagram of a WAKE sub-routine of the main routine of FIG. 2a-1, -2.

FIG. 5 illustrates a WAKE sub-routine 330 that is carried out when the detector 50 is awakened from the sleep mode. At block 330a, the detector 50 determines whether the TEST mode flag is set. If a TEST mode flag is set, the process proceeds to a RESUMET sub-routine 330b. During the RESUMET sub-routine 3306, the detector 50 is kept STARVED (as described above) at block 330c, the yellow light is kept on at block 330d, and the WAKE UP counter is set equal to 1 at block 330e. The detector unit 50 then determines whether the ALARM flag is set at block 330f. If an ALARM flag is set, the process proceeds to a RESET sub-routine as further described below. If the ALARM flag is not set, the process proceeds to a LOOP sub-routine as further described below.

If the TEST mode flag is not set at block 330a, the detector 50 determines whether the ALARM flag is set at block 330c. If the ALARM flag is set, the detector 50 determines whether there is a smoke or carbon monoxide condition at block 330d. If the ALARM flag is not set at block 330c, the detector 50 determines whether the TEST switch is pressed at block 330e. If the TEST switch is not pressed, the process proceeds to a BYE1 sub-routine as further described below.

If the TEST switch is pressed at block 330e, the detector 50 saves the ALARM register at block 330f, sets a TEST flag, sets a WAKEUP counter equal to 1, and turns on the yellow LED4 of the power/low battery indicator circuitry 129 at block 330g. The detector 50 then determines whether the battery level is low at block 330h. If the battery level is not low, the green LED4 of the power/low battery indicator circuitry 129 is turned on at block 330l.

If the battery level of the detector 50 is low at block 330h, the detector turns on the yellow LED at block 330j. The detector then simulates a smoke alarm and turns on the smoke LED3 of the smoke alarm indicator circuitry 124 at block 330k and sound a smoke alarm pattern at block 330l.

The detector unit then turns off the smoke LED and simulates the carbon monoxide alarm at block 330m. The detector 50 now turns on the carbon monoxide alarm horn pattern and the LED2 of the carbon monoxide alarm indicator circuitry 122 at block 330n. Thereafter, the detector 50 turns off the carbon monoxide alarm and the carbon monoxide alarm LED3 at block 330o. The detector will then enter the sleep mode.

Figure 6:
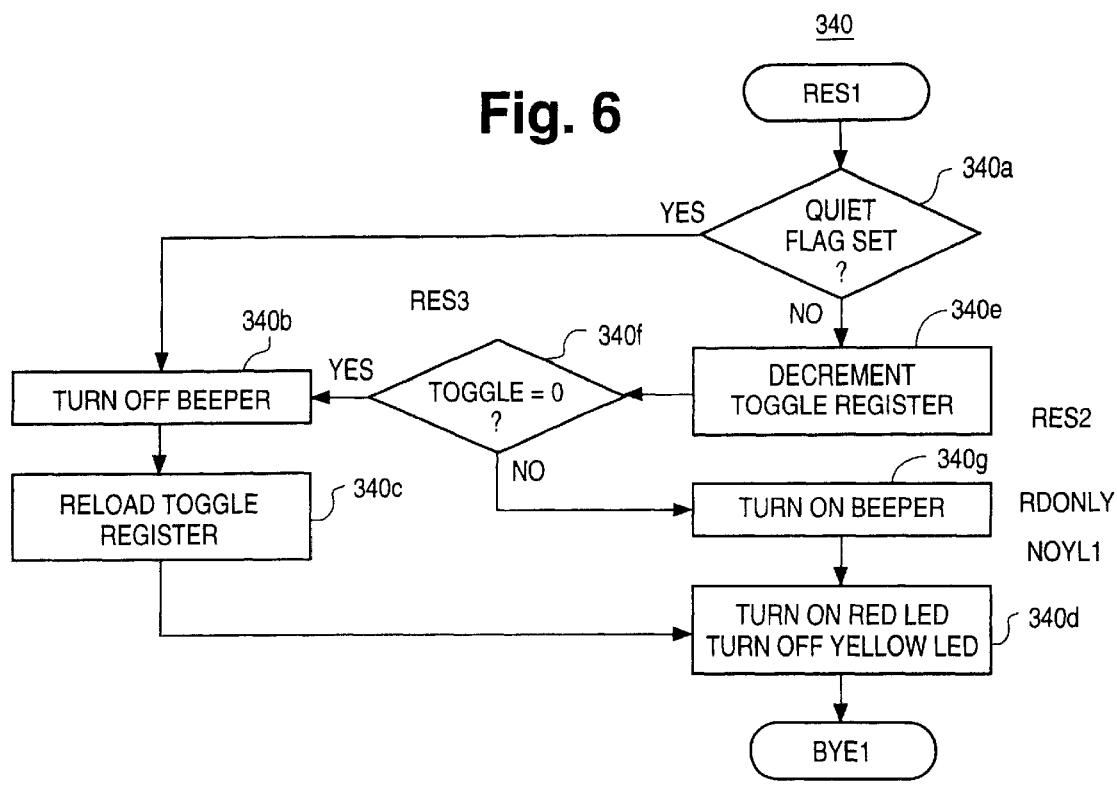
FIG. 6 is a flow diagram o[0086] a RES1 sub-routine of the main routine of FIG. 2a-1, -2.

FIG. 6 illustrates, a RS1 sub-routine 340. The reset subroutine 340 is utilized to flash the red and yellow LEDS as CO samples are taken during the test function and sound the alarm when the circuitry has passed the self test. At block 340a, the detector 50 determines whether a QUIET flag is set. If the QUIET flag is set, the detector 50 turns off a BEEPER at block 340b, reloads a TOGGLE register at block 340c, and turns off the red LED2 and yellow LED3 at block 340d.

If the QUIET flag is not set at block 340a, the detector 50 decrements the TOGGLE register at block 340e and then determines whether the TOGGLE register is equal to zero at block 340f. If the TOGGLE register is equal to zero, the process proceeds to block 340b as described above.

If the TOGGLE register is not equal to zero at block 340f, the detector 50 turns on the BEEPER at block 340g and turns on the red LED2 and yellow LED3 at block 340d. Subsequently, the process proceeds to the BYE1 sub-routine as further described below.

Figure 7:
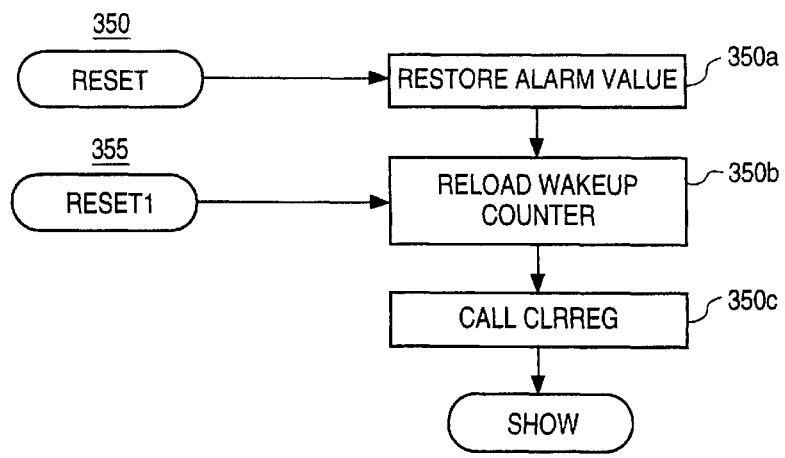
FIG. 7 is a flow diagram of a RESET, sub-routine and a RESET1 sub-routine of the main routine of FIG 2a-1, -2.

FIG. 7 illustrates a RESET sub-routine 350 and a RESET1 sub-routine 355. The RESET sub-routine and RESET1 sub-routine are utilized to restore registers after a manual test.

When the detector 50 carries out the RESET sub-routine 350, it restores the ALARM value at block 350a, reloads the WAKEUP counter at block 350b, and calls CLRREG at block 350c. The process then proceeds to a SHOW sub-routine as further described below.

When the detector 50 carries out the RESET1 sub-routine 355, it reloads the wake-up counter at block 350b and calls CLRREG at block 250c. The process then proceeds to the SHOW sub-routine.

Figure 8:
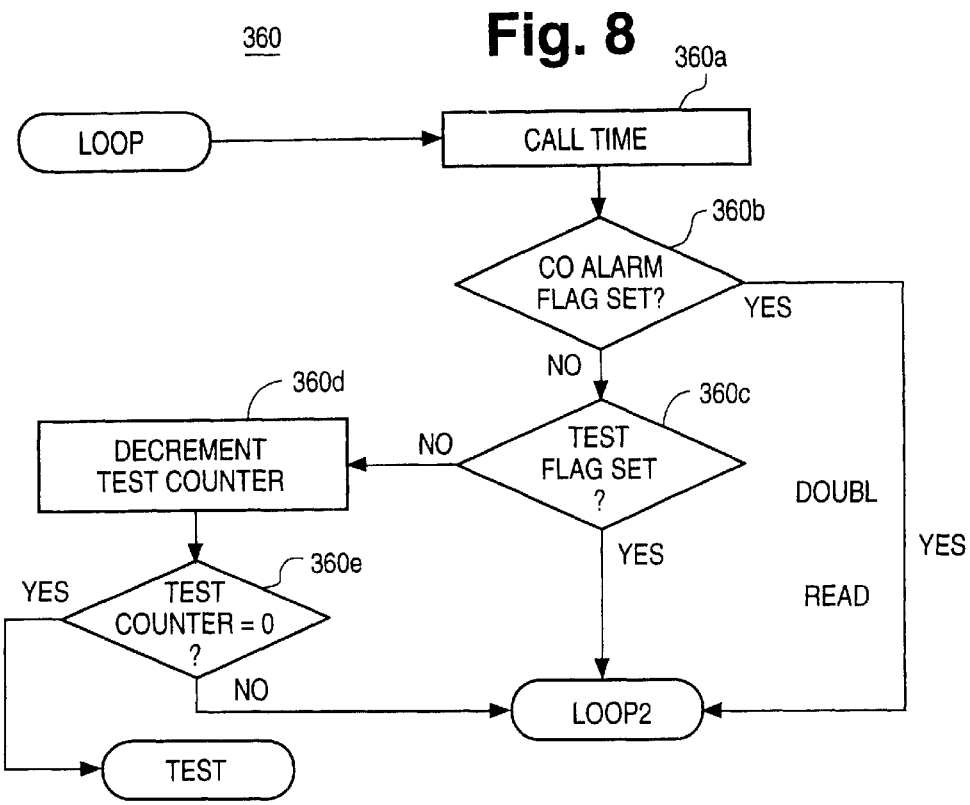
FIG. 8 is a flow diagram oμ a LOOP sub-routine of the main routine of FIG. 2a-1, -2.

Referring now to FIG. 8 illustrates a LOOP sub-routine 360. The LOOP sub-routine is utilized to determine if the CO alarm flag is set during a test, or if more samples must be taken.

At block 360a, the detector unit 50 retrieves the TIME and then determines whether the carbon monoxide ALARM flag is set at block 360b. If the carbon monoxide ALARM flag is set, the process proceeds to a LOOP2 sub-routine as further described below.

If the carbon monoxide ALARM flag is not set at block 360b, the detector determines whether the TEST flag is set at block 360c. If the TEST flag is set, the process proceeds to the LOOP2 sub-routine.

If the TEST flag is not set at block 360c, the detector decrements the TEST counter at block 360d and then determines whether the TEST counter is equal to zero at block 360e. If the TEST counter is not equal to zero, the process proceeds to the LOOP2 sub-routine. If the TEST counter is equal to zero, the process proceeds to the TEST sub-routine as further described below.

Figure 9:
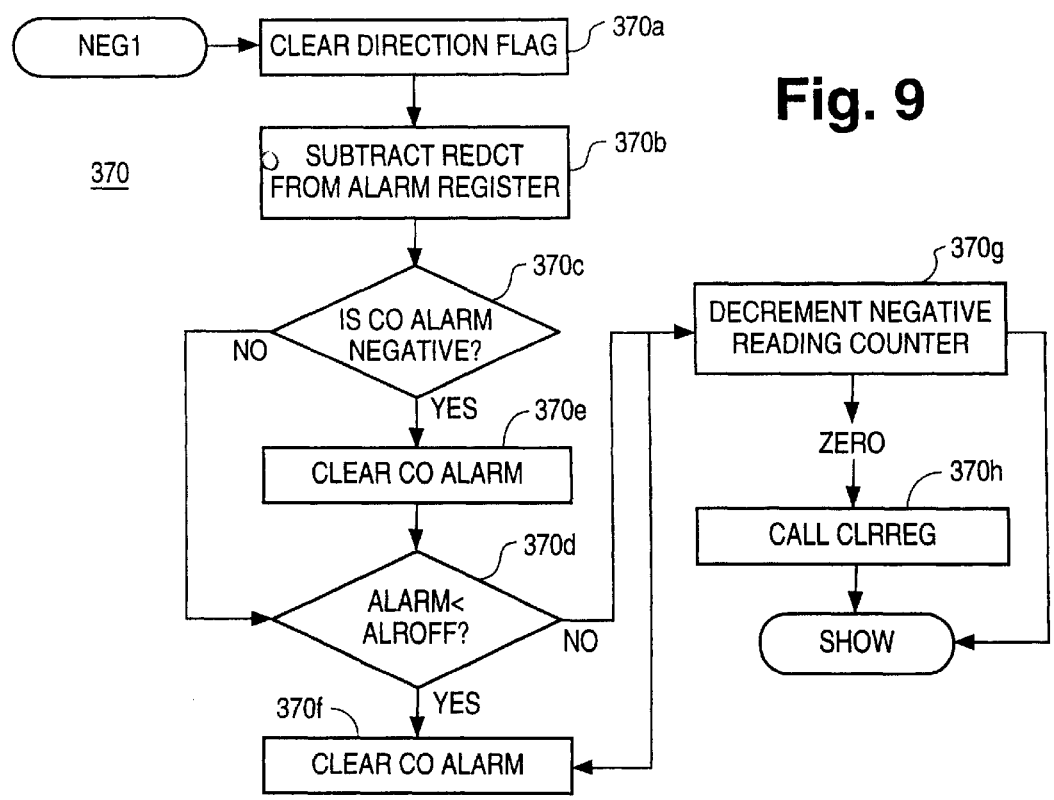
FIG. 9 is a flow diagram of a NEG1 sub-routine of the main routine of FIG. 2a-1, -2.

FIG. 9 illustrates a NEG1 sub-routine 370 to carry out a reduction in the counts value to clear an alarm condition if the CO level is decreasing. At block 370a, the detector 50 clears the DIRECTION flag and the subtracts a REDCT value from an ALARM register at block 370b. At block 370c, the detector 50 determines whether the carbon monoxide ALARM is negative.

If the carbon monoxide ALARM is not negative, the process proceeds to block 370d as further described below. If the carbon monoxide ALARM is negative at block 370c, the detector clears the carbon monoxide ALARM at block 370e and then determines whether an ALARM value is less than an ALROFF value at block 370d. If the ALARM is less than ALROFF, then the detector 50 clears the carbon monoxide ALARM at block 370f.

If the ALARM value is not greater than the ALROFF value at block 370d, the detector 50 decrements a NEGATIVE READING counter at block 370g. If the NEGATIVE READING counter is equal to zero, the detector unit calls CLRREG and the process proceed to the SHOW sub-routine. If the NEGATIVE READING counter is not equal to zero, the process proceeds correctly to the SHOW sub-routine.

Figure 10:
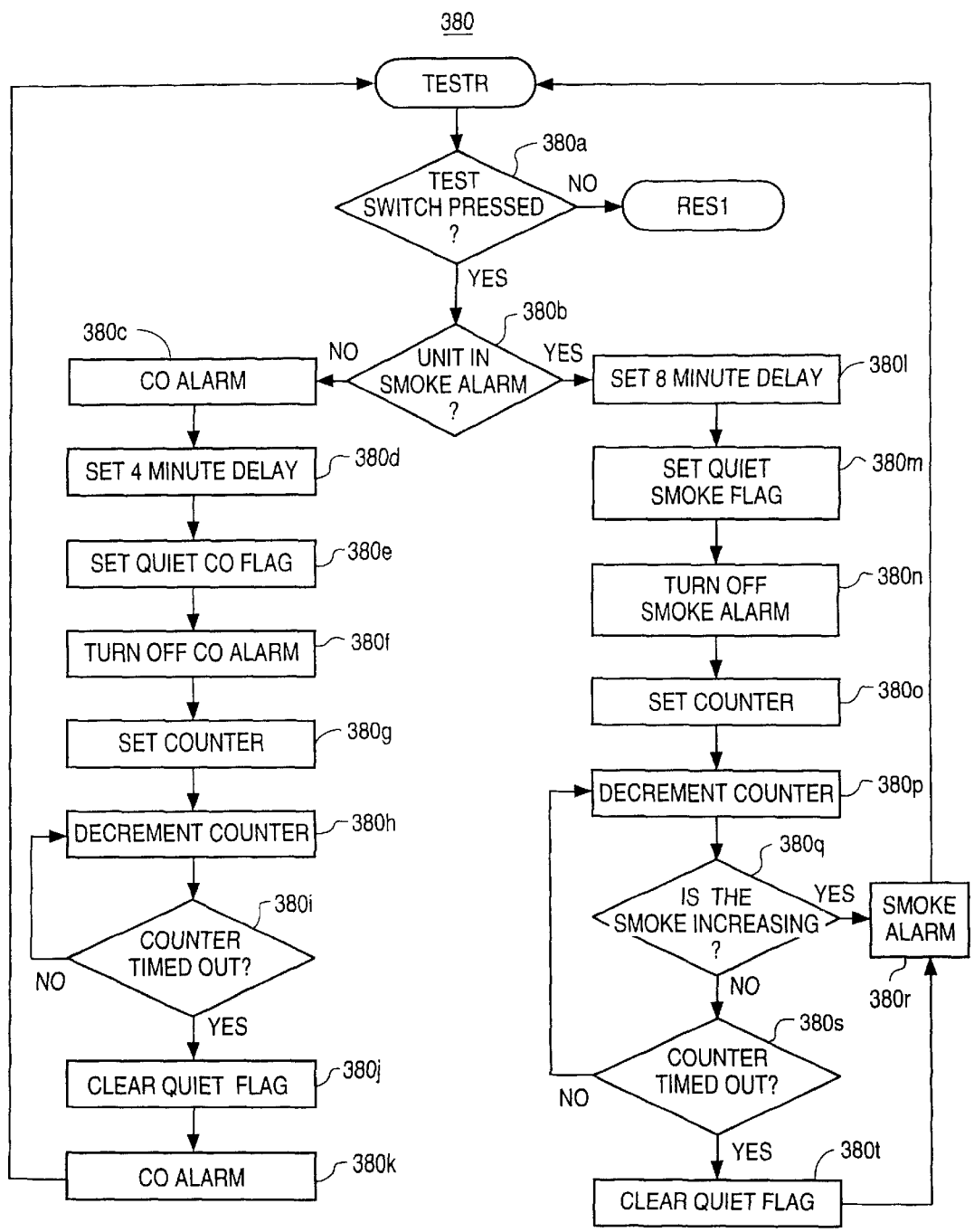
FIG. 10 is a flow diagram of a TESTR sub-routine of the main routine of FIG. 2a-1, -2.

FIG. 10 illustrates a TESTR sub-routine 380. The TESTR sub-routine 380 is utilized when the test switch is pressed by a user.

At block 380a, the detector unit 50 determines whether the test switch is pressed. If the test switch is not pressed, the process proceeds to the RES1 sub-routine 340 as described above. If the TEST SWITCH is pressed at 380a, the detector 50 determines whether the unit is in a smoke alarm condition at block 380b.

If the detector 50 is not in a smoke alarm condition at block 380b, it activates the carbon monoxide ALARM at block 380c, sets a four minute delay at block 380d, sets a QUIET carbon monoxide flag at block 380e, turns off the carbon monoxide ALARM at block 380*f*, sets a counter at block 380*g*, and decrements the counter at block 380*h*. At block 380*i*, the detector 50 determines whether the counter has timed out. If the counter has not timed out, the process proceeds to block 380*h*. If the counter has time out at block 380*i*, the detector 50 clears the QUIET flag at block 380*j* and turns on the carbon monoxide ALARM at block 380*k*. The process then returns to the beginning of the TESTR subroutine 380.

If the detector 50 is in a smoke alarm condition at block 380*b*, it sets. an eight minute delay at block 380*l*, sets a QUIET, smoke flag at block 380*m*, turns off the smoke alarm at block 380*n*, sets a counter at block 380*o*, and decrements the counter at block 380*p*. The detector 50 determines whether the smoke is increasing at block 380*g*.

If the smoke is increasing, the detector activates the smoke alarm at block 380*r* and the process proceeds to the beginning of the TESTR sub-routine 380. If the smoke is not increasing at block 380*g*, the detector 50 determines whether the counter has timed out at block 380*s*.

If the counter has not timed out, the process proceeds to block 380*p*. If the counter has timed out at block 380*s*, the detector 50 clears the QUIET flag at block 380*f* and activates the smoke alarm at block 380*r*. The process then proceeds to the beginning of the TESTR sub-routine 380.

Figure 11:
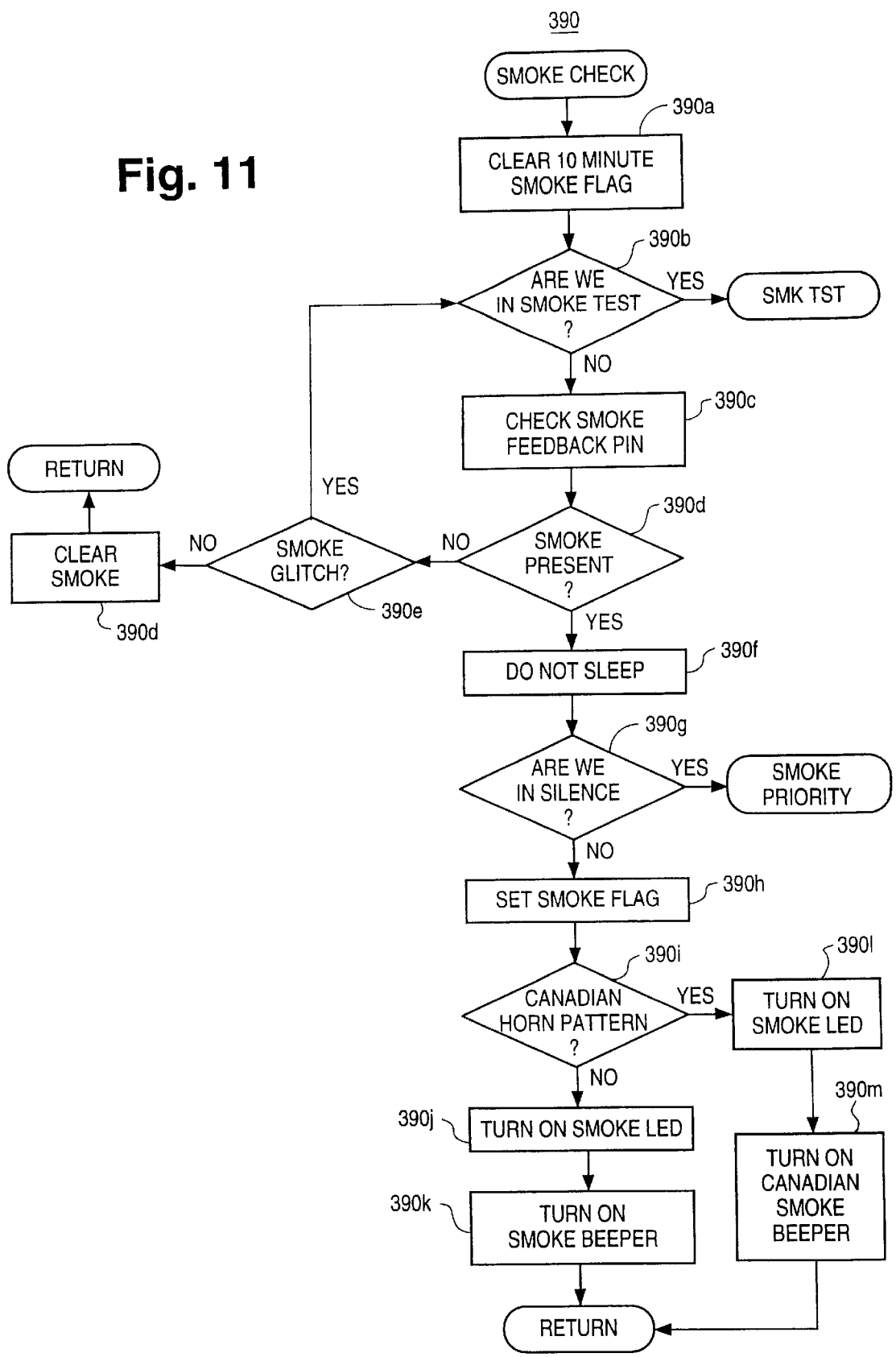
FIG. 11 is a flow diagram of a SMOKE CHECK sub-routine of the main routine of FIG. 2a-1, -2.

FIG. 11 illustrates a SMOKE CHECK sub-routine 390. The SMOKE CHECK sub-routine determines whether the smoke sensor has detected the presence of smoke in the atmosphere and initiates a smoke alarm.

At block 390*a*, the detector 50 clears a ten minute SMOKE flag. The detector 50 then determines whether a smoke test is in progress at block 390*b*.

If the smoke test is in progress, the process proceeds to a SMK-TEST sub-routine&as ,further described below. If the detector 50 is not to carry out a smoke test, it checks a smoke feedback pin of the sensor at block 390*c*. The detector unit then determines whether smoke is present in the atmosphere at block 390*d*.

If smoke is not present, the detector 50 determines whether there has been a smoke glitch at block 390*e*. If there has been a smoke glitch, the process proceeds to block 390*b*. If there is not smoke glitch at block 390*e*, the detector 50 clears the smoke at block 390*d* and returns to the beginning of the SMOKE CHECK sub-routine 390.

If the detector unit 50 determines that smoke is present at block 390*d*, it continues processing at block 390*f*. The detector 50 then determines whether it is in a silence mode at block 390*g*. If the detector unit 50 is in the hush mode,, the process proceeds to a SMOKE PRIORITY subroutine as further described below.

If the detector 50 is not in the silence mode at block 390*g*, it the detector unit 500 sets a SMOKE flag at block 390*h* and then determines whether to execute a Canadian horn pattern at block 390*i*. One of the advantages of the detector 50 is its ability to store a plurality of horn patterns and use one or more selected patterns.

If the Canadian horn pattern is implemented by the detector 50 at block 390*i*, it turns on the smoke LED3 at block 390*j* and turns on the SMOKE BEEPER at block 390*k*. The process then returns to the beginning of the SMOKE CHECK sub-routine.

If the Canadian horn pattern is to be executed at block 390*i*, the detector 50 will turn on the smoke LED3 at block 390*l* and will turn on the Canadian smoke beeper at block 390*m*. The process then returns to the beginning of the SMOKE CHECK sub-routine 390.

Figure 12:
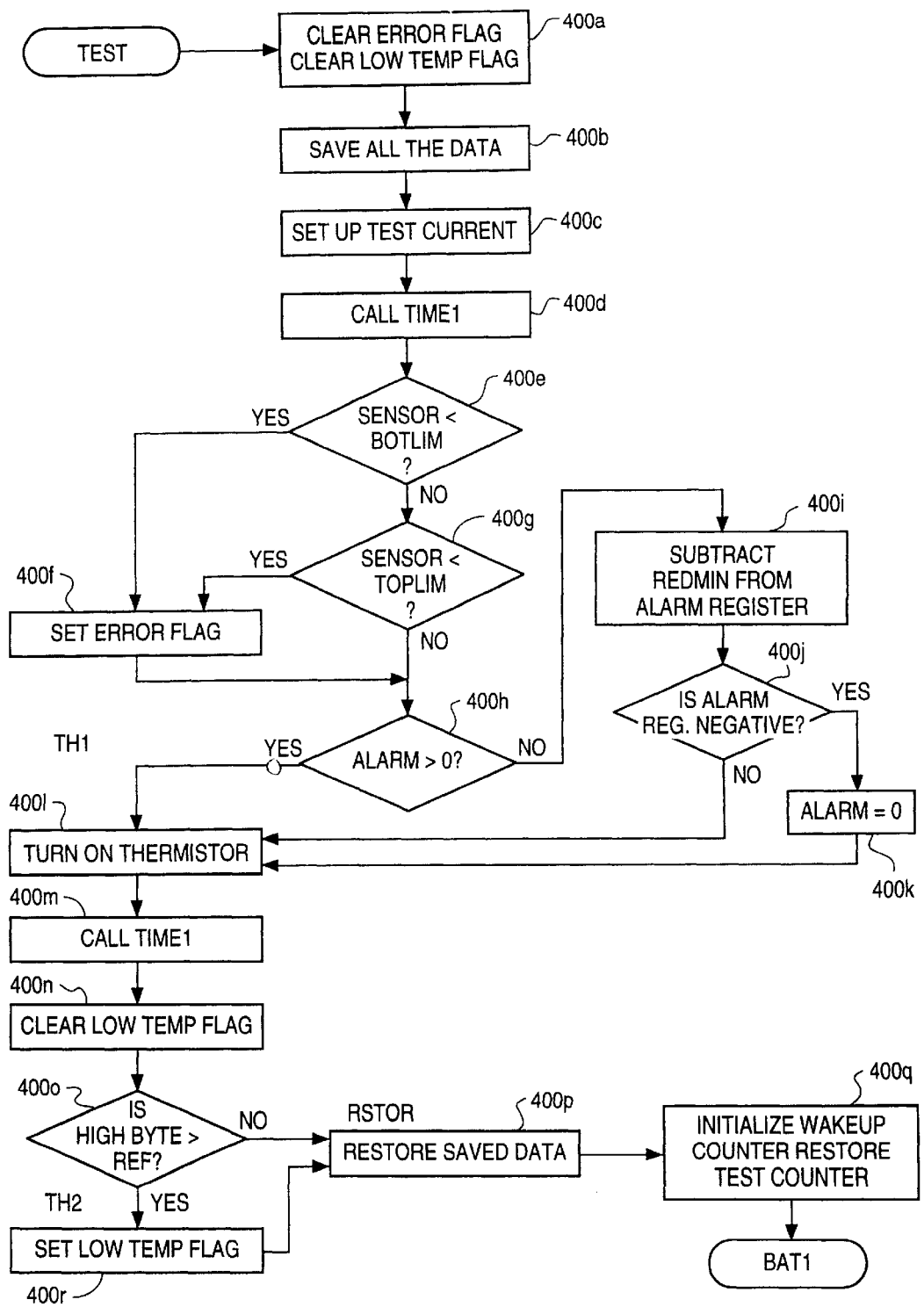
FIG. 12 is a flow diagram of a TEST sub-routine of the main routine of FIG. 2a-1, -2.

FIG. 12 illustrates a TEST sub-routine 400 to test smoke sensor functioning. Initially, the detector 50 clears an ERROR flag and LOW TEMP flag at block 400*a*, saves all the data at block 400*b*, sets up a test current at block 400*c*, and calls an TIME1 at block 400*d*. The detector 50 then determines whether the sensor output is less than a BOTLIM value at block 400*e*. If the sensor output is less than the BOTLIM value, the detector 50 sets an ERROR flag at block 400*f* and the process proceeds to block 400*h* as further described below.

If the sensor output is not less than the BOTLIM value at block 400*e*, the detector 50 determines whether the sensor output is greater than a TOPLIM value at block 400*g*. If the sensor output is less than the TOPLIM value, the detector 50 sets the ERROR flag at block 400*f* and the process proceeds to block 400*h*. If the sensor output is not less than the TOPLIM value at block 400*g*, the detector 50 determines whether an ALARM is greater than zero at block 400*h*.

If the ALARM is not greater than zero at block 400*h*, the detector 50 subtracts a REDMIN value from the ALARM register at block 400*i* and then determines whether the ALARM register is negative at block 400*j*. If the ALARM register is negative, the detector 50 sets the ALARM register equal to zero at block 400*k* and the process proceeds to block 400*l* as further described below. If the ALARM register is not negative at block 400*j*, the process proceeds to block 400*l*.

If the ALARM is greater than zero at block 400*h*, the detector 50 turns on the thermistor at block 400*l*, calls TIME1 at block 400*m*, and clears a LOW TEMP flag at block 400*n*. The detector 50 then determines whether a HIGH BYTE value is greater than REF value at block 400*o*.

If the HIGH BYTE value is not greater than REF value, the detector restores the saved data at block 400*p*, and initializes the WAKEUP counter and restores the TEST counter at block 400*q*. The process then proceeds to the BAT1 sub-routine as further described below.

If the HIGH BYTE value is greater than the REF value at block 400*o*,. the detector 500 sets the LOW TEMP flag at 400*r*, restores the saved data at block 400*p*, initializes the WAKEUP counter, and restores the TEST counter at block 400*q*. The process then proceeds to the BAT1 sub-routine.

Figure 13:
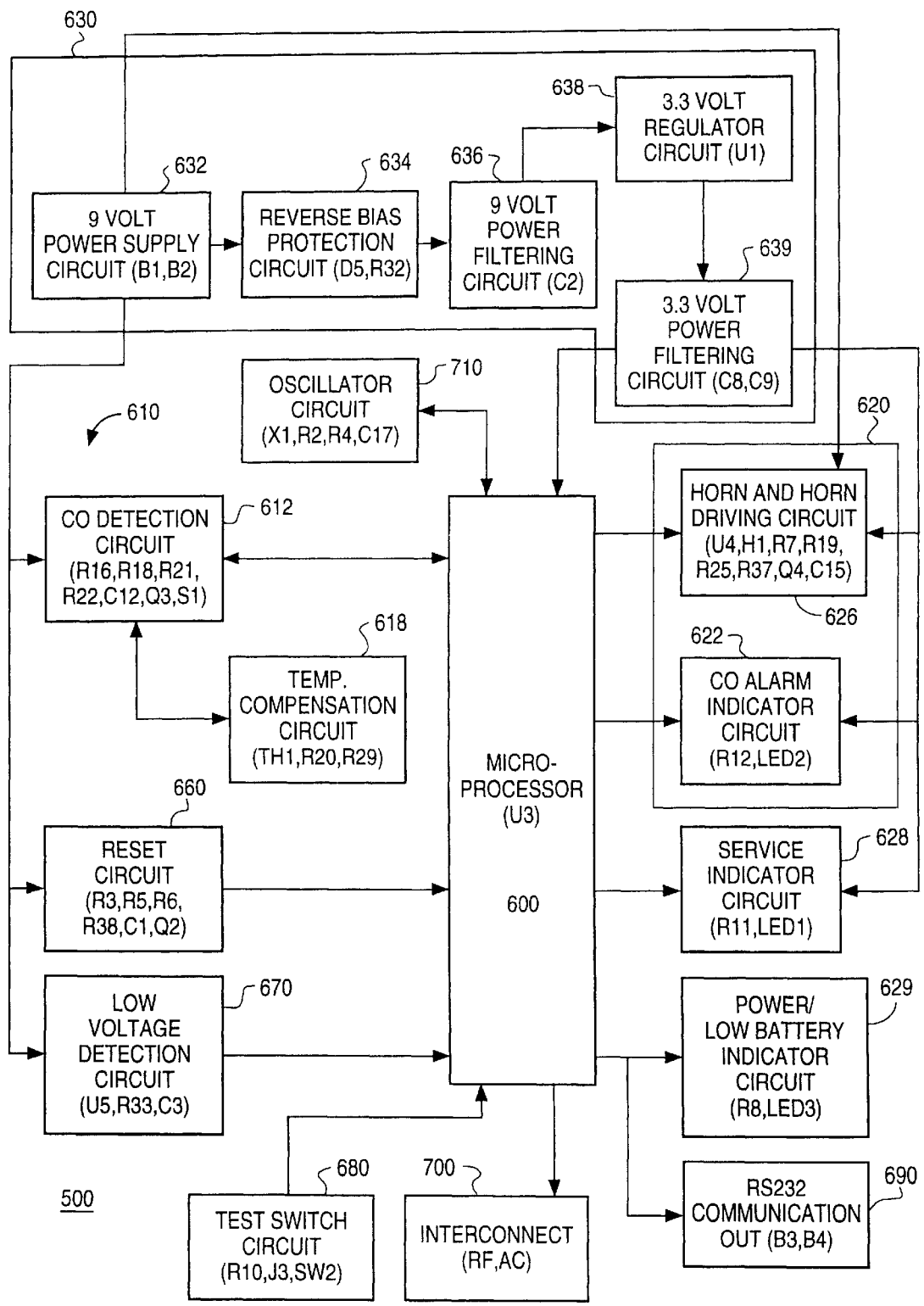
FIG. 13 is a block diagram of an alternate detector, carbon monoxide.
Figures 2, 14:
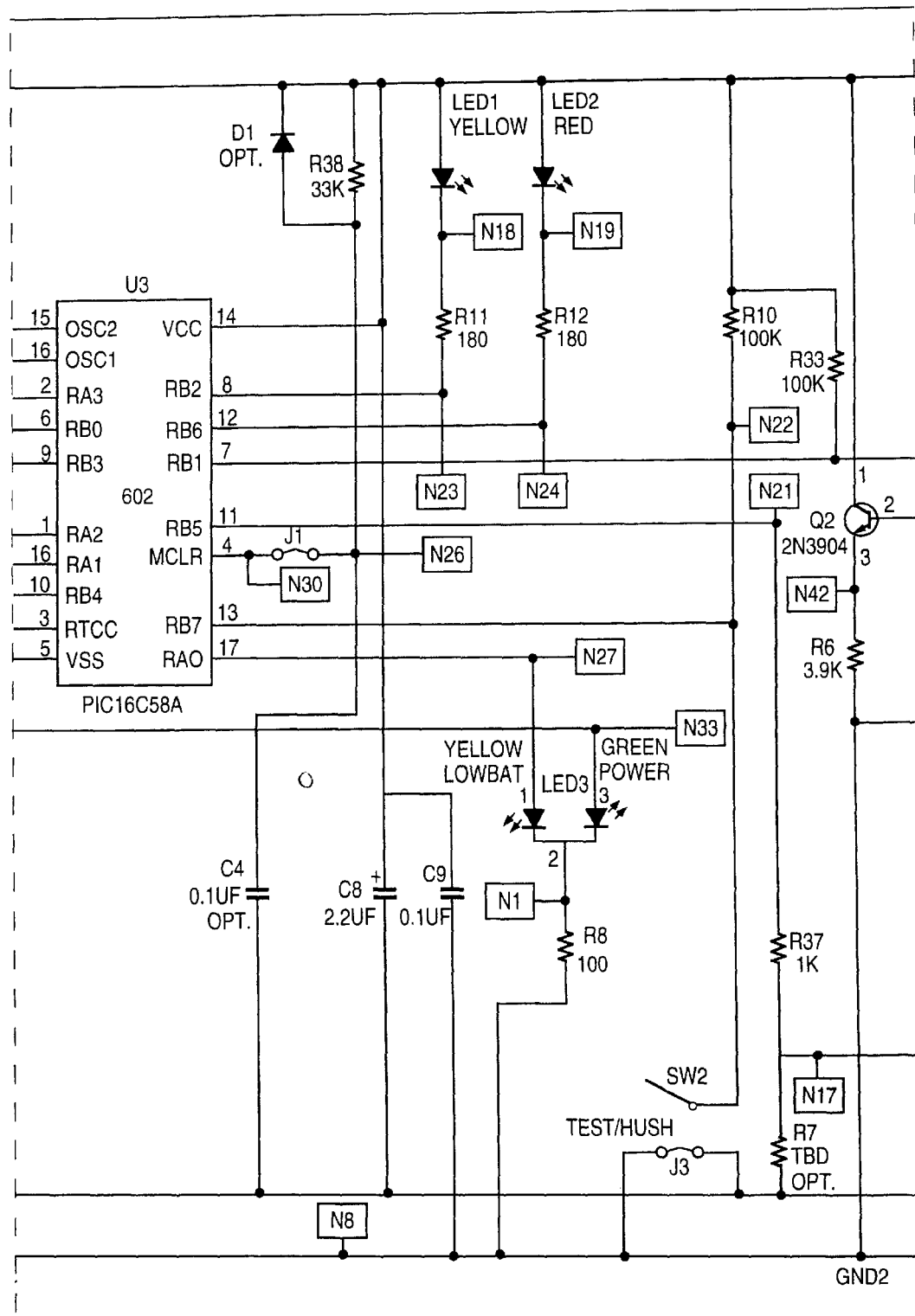
FIG. 14 is a schematic diagram of the detector of FIG. 13.
Figures 3, 14:
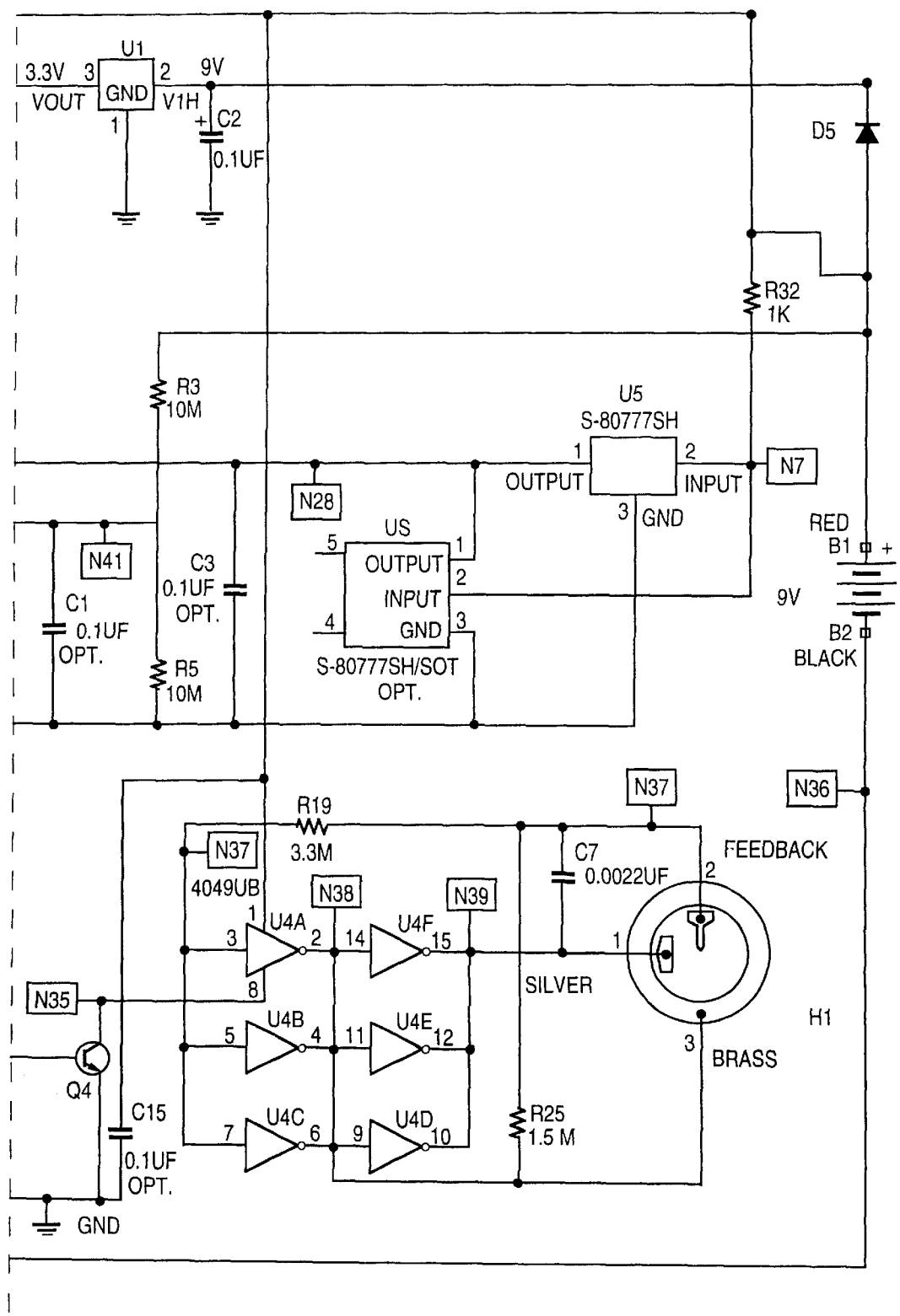

Referring now to FIG. 13, a block diagram of another embodiment of a detector 500 is illustrated. The detector 500 is a battery powered, single station, self-contained carbon monoxide alarm. The detector 500 detects the presence and concentration of carbon monoxide in the atmosphere and provides a warning of potential hazardous carbon monoxide conditions. The detector 500 corresponds in many respects in construction and function to the previously described detector 50 except that the detector 500 does not detected the presence of smoke. The component of the detector 500 generally corresponding to those components of the detector unit 50 are designated by like-reference numerals in the six-hundred series. As shown in FIG. 14, the central processing unit 602 includes a microchip PIC16C58A, available from microchip.

Figure 15A:
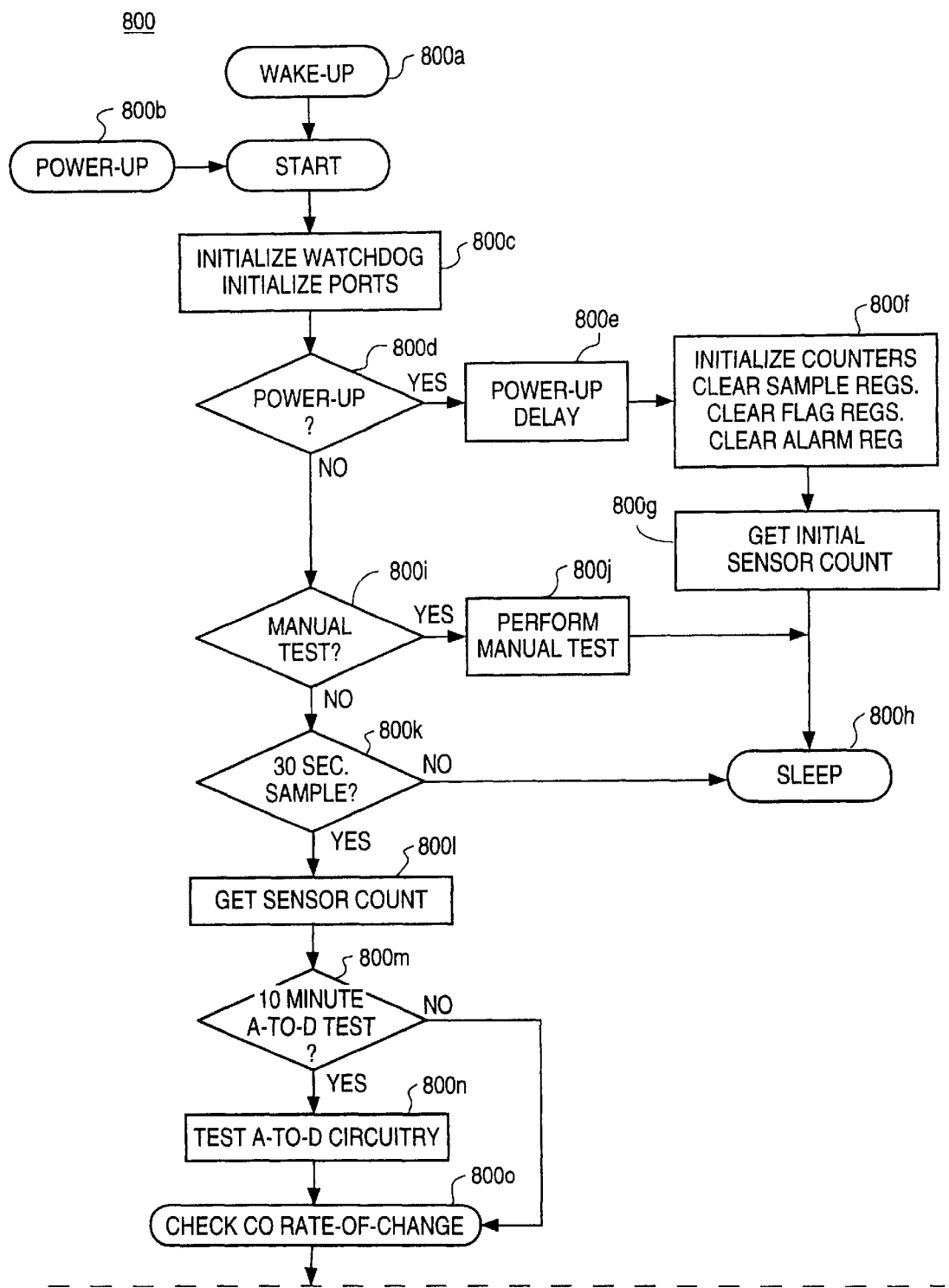
FIG. 15 is a flow diagram illustrating the general operation of the detector of FIG. 13.

FIG. 15 illustrates a flow diagram of the general operations carried out by the detector 500. The detector monitors the carbon monoxide in the atmosphere and sounds an alarm if a hazard condition is present.

After the detector 500 is awakened at block 800*a* or powered up at block 800*b*, the detector initializes a watchdog timer and initializes one or more ports at block 800*c*. At block 800*d*, the detector 500 determines whether the unit was just powered up. If the detector 500 was just powered up, the detector implements a power-up delay at block 800*e*, and then initializes one or more counters, clears one or more sample registers, clears one or more flag registers, and clears an alarm register at block 800*f*. The detector 500 then obtains an initial sensor count at block 800*g* and then the detector 500 is put in the sleep mode at block 800*h*.

If the detector 500 was not recently powered up at block 800*d*, the detector 500 determines whether to implement a manual test at block 800*i*. If the manual test is to be implemented, the detector 500 performs the manual test at block 800*j* and then the detector 500 is put in the sleep mode at block 800*h*.

If a manual test is not to be performed at block 800*i*, the detector 500 determines whether to obtain a 30 second sample at block 800*k*. If the detector 500 is not to obtain a sample, the detector 500 will be put in the sleep mode at block 800*h*.

If the detector 500 is to obtain a 30 second sample at block 800*k*, the detector 500 obtains a sensor count at block 800*l* and then determines whether to perform a 10 minute A-to-D test at block 800*m*. If the detector 500 is not to perform the A-to-D test, the process proceeds to block 800*o*.

If the detector 500 is to perform the 10 minute A-to-D test at block 800*m*, the detector 500 tests the A-to-D circuitry at block 800*n* and then checks the carbon monoxide rate of change at block 800*o*.

At block 800*p*, the detector 500 determines whether to activate the carbon monoxide alarm. If the carbon monoxide alarm is to be activated, the detector 50 flashes the light indicator LED2 of the carbon monoxide indicator circuitry 622 (see FIG. 15) and sounds the carbon monoxide horn pattern at 800*q*. The process then proceeds to block 800*s* as further described below.

If the carbon monoxide alarm is not to be activated at block 800*p*, the detector 50 turns off the carbon monoxide LED2 and horn at block 800*r*, and shows data at block 800*s*.

At block 800*t*, the detect or 500 determines whether there are any faults at block 800*t*. If there are not any faults at block 800*t*, the detector 500 is put in the sleep mode at block 800*w*.

If there are faults, the detector 500 determines whether to check the carbon monoxide alarm at block 800*u*. If the carbon monoxide is to be checked, the detector 500 is put in the sleep mode at block 800*w*. If there is no problem with the carbon monoxide alarm is not to be checked, the detector 500 generates a trouble chirp at block 800*v* and then the detector is put into the sleep mode at block 800*w*.

FIG. 16 shows a flow diagram of a main program carried out by the detector 500. At block 810*a*, the detector 500 sets a wake-up time i.e., about 3 seconds for normal mode and about 1.5 seconds for alarm mode). The detector 500 then initializes ports A and B at block 810*b* and determines whether a TIME OUT bit is cleared at block 810*c*. If the TIME OUT bit is cleared, the detector 500 proceeds to a WAKE sub-routine as further described below.

If the TIME OUT bit is not cleared at block 810*c*, the process proceeds to a POWER UP sub-routine as further described below. The detector 500 then waits about 300 ms at block 810*d*. At block 810*e*, the detector 500 initializes a WAKE UP counter, a SAMPLE counter, and a TEST counter at block 810*e*. The detector 500 then clears one or more registers and flags at block 810*f*, clears an ALARM REGISTER at block 810*g*, sets a START flag at block 810*h*, and then goes into the sleep mode.

Figure 17:
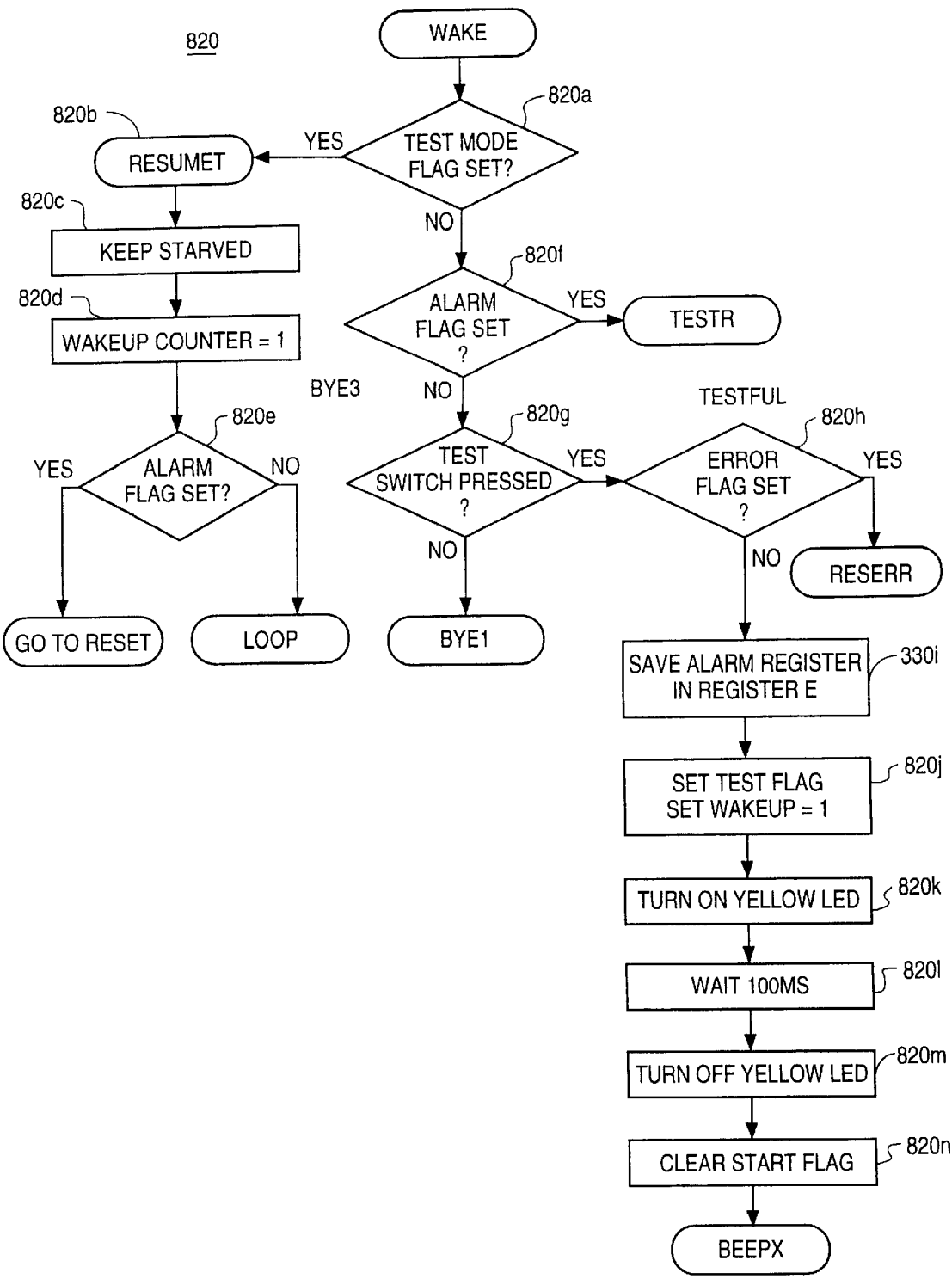
FIG. 17 is a flow diagram of a WAKE sub-routine of the main routine of FIG. 16.

Referring now to FIG. 17, a WAKE sub-routine 820 is illustrated. The WAKE sub-routine is performed when the processor is awakened from the sleep mode.

At block 820*a*, the detector 500 determines whether a TEST MODE flag is set. If the TEST MODE. flag is set, the process will proceed to a RESUMET sub-routine 820*b*. While carryingout the steps of the RESUMET sub-routine 820*b*, the detector 500 is kept STARVED at block 820*c* and a WAKEUP counter is set equal to 1 at block 820*d*. The detector 500 then determines whether the ALARM flag is set at block 820*e*. If the ALARM flag is set, the process proceeds to a RESET sub-routine as further described below. If the ALARM flag is not set at block 820*e*, the process proceeds to a LOOP sub-routine as further described below.

If the TEST MODE flag is not set at block 820*a*, the detector 500 determines whether an ALARM flag is set at block 820*f*. If the ALARM flag is set, the process proceeds to a TESTR sub-routine as further described below.

If the ALARM flag is set at block 820*f*, the detector 500 determines whether a test switch is pressed at block 820*g*. If the test switch is not pressed, the process proceeds to a BYE1 sub-routine as further described below.

If the test switch is pressed at block 820*g*, the detector 500 determines whether an error flag is set at block 820*h*. If the error flag is set, the process proceeds to a RESERR sub-routine as further described below.

If the error flag is not set at block 820*h*, the detector saves the data in an ALARM register at block 820*i*, sets a TEST flag and setsthe WAKEUP counter equal to 1 at block 820*j*. Thereafter, the detector 500 turns on the yellow LED 1 at block 820*k*, waits 100 ms at block 820*l*, turns off the yellow LED1 at block 820*m*, and clears a START flag at 820*n*. The process will then proceed to a BEEPX sub-routine as further described below.

Figure 18:
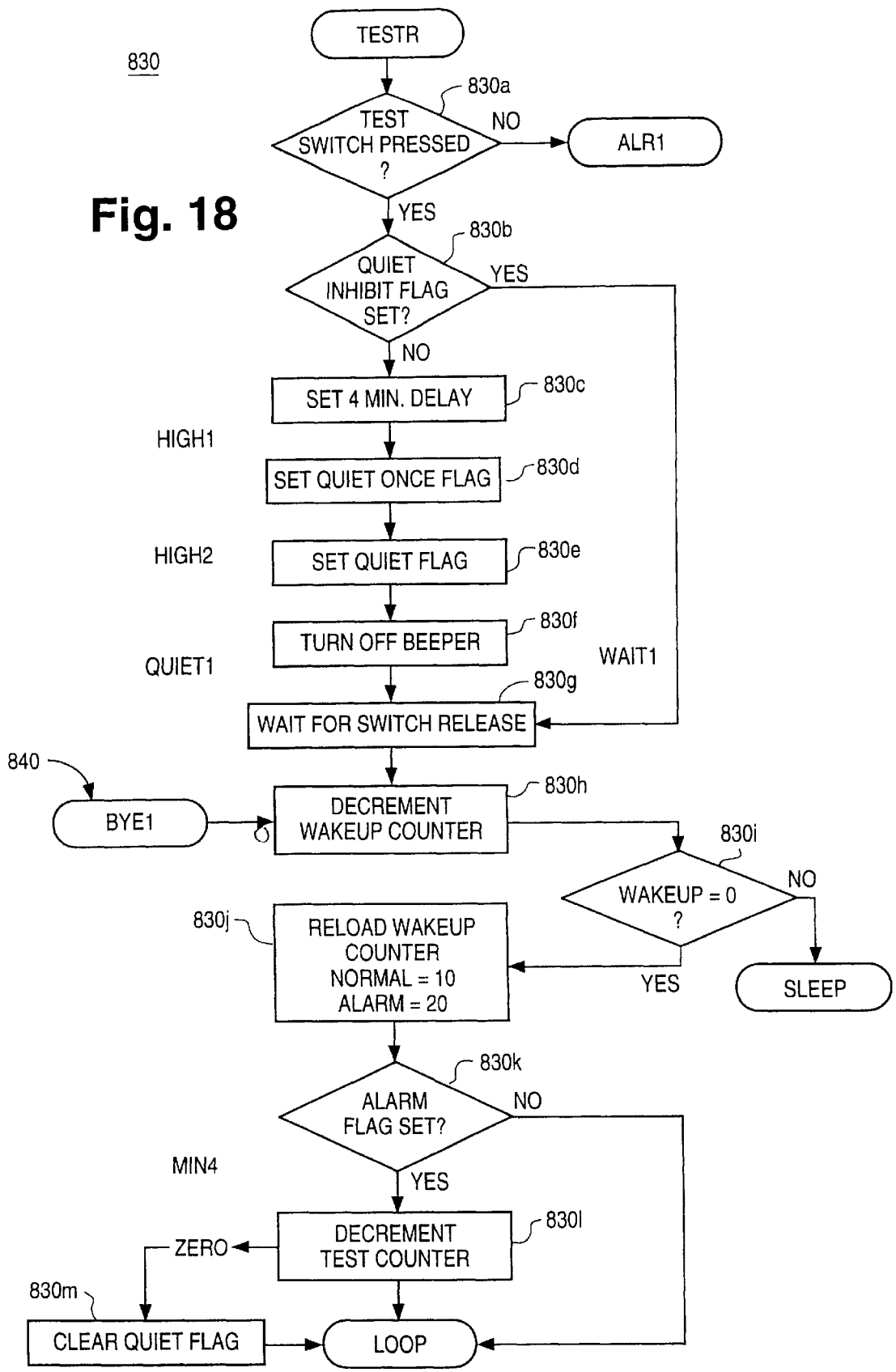
FIG. 18 is a flow diagram of a TESTER sub-routine and a BYE1 sub-routine of the main routine of FIG. 16.

FIG. 18 illustrates a BY1 sub-routine 840 and the TESTR sub-routine 830. The TESTR sub-routine 830 is utilized to determine if the test switch is being pressed during an alarm to silence the unit and the BYE1 sub-routine is utilized to decrement the WAKEUP counter to determine what WAKEUP routine to accomplish.

At block 830*a*, the detector 500 determines whether the test switch is pressed. If the test switch is not pressed, the process proceeds to an ALR1 sub-routine as further described below. If the test switch is pressed at block 830*a*, the detector 500 determines whether a QUIET INHIBIT flag is set at block 830*b*. If the QUIET INHIBIT flag is set, the process proceeds to block 830*g* as further described below.

If the QUIET INHIBIT flag is not set at block 830*b*, the detector 500 sets a 4 minute delay at block 830*c*, sets a QUIET ONCE flag at block 830*d*, sets a QUIET flag at block 830*e*, turns off the beeper at block 830*f*, waits for a switch release at block 830*g*, and then decrements the WAKEUP counter at block 830*h*. The detector 500 then determines whether the WAKEUP counter is equal to zero at block 830*i*. If the WAKEUP counter is not equal to zero, the detector 500 is put into the sleep mode.

If the WAKEUP counter is equal to zero at block 830*i*, the WAKEUP counter is reloaded (i.e., the WAKEUP counter is set to 10 for normal mode and equal to 20 for alarm mode) at block 830*j*. At block 830*h*, the detector 500 determines whether the ALARM flag is set. If the ALARM flag is not set, the process proceeds to a LOOP sub-routine as further described below.

If the ALARM flag is set at block 830*h*, the detector 500 decrements the TEST counter at block 830*l*, and the process proceeds to a LOOP sub-routine. If the TEST counter is equal to zero at block 830*l*, the detector 500 clears the QUIET flag at block 830*m* and the process proceeds to the LOOP sub-routine.

Referring now to FIG. 19, a flow diagram of the ALR1 sub-routine 840 is illustrated. The ALR1 sub-routine 840 is utilized to activate the carbon monoxide LED2 and horn.

At block 840a, a TEST ALARM counter is set equal to 2 and an ALARM COUNTER is set equal to 3. At block 840b, the detector determines whether the QUIET flag is set. If the QUIET flag is set, the process proceeds to block 840d as further described below.

If the QUIET flag is not set at block 840b, the detector 500 turns on the horn at block 840e, turns on the carbon monoxide LED2 at block 840d, waits 100 ms at block 840e, turns off the carbon monoxide LED2 at block 840f, waits about 400 ms at block 840g, decrements the ALARM counter at block 840h, and then determines whether the ALARM counter is equal to zero at block 840i. If the alarm counter is not equal to zero, the process proceeds to block 840b.

If the alarm counter is equal to zero at block 840i, the detector 500 turns off the horn at block 840j and then determines whether a TEST flag is set at block 840k. If the TEST flag is set, the detector 500 decrements the test alarm counter by 1 at block 840l and then determines whether the test alarm counter is equal to zero at block 840m.

If the test alarm counter is equal to zero, the process proceeds to a RESET sub-routine as further described below. If the test alarm counter is not equal to zero at block 840m, the detector will be put into the sleep mode.

If the TEST flag is set not at block 840k, the detector 500 will decrement the WAKEUP counter by 1 at block 840n and then the detector 500 determines whether the WAKEUP counter is equal to zero at block 840o. If the WAKEUP counter is not equal to zero, the detector 500 is put into the sleep mode.

If the WAKEUP counter is equal to zero at block 840o, the detector 500 reloads the WAKEUP counter with a ALARM DIV value at block 840p. The process then proceeds to a sub-routine MIN4 as further described below.

FIG. 20 illustrates the RESET sub-routine 850 and a RESET1 sub-routine 852 of the main routine. At block 850a, the detector 500 restores the ALARM value. The detector 500 then reloads the WAKEUP counter at block 850b and then calls CLRREG at block 850c. The process then proceeds to ALRH_X sub-routine as further described below.

Referring now to FIG. 21, the LOOP sub-routine 860 is illustrated. The LOOP sub-routine 860 is implemented to determine if a manual self test needs to be performed. At block 860a, the detector 500 calls TIME and then determines whether an ALARM flag is set at block 860b. If the ALARM flag is set, the process proceeds to a LOOP2 sub-routin[0085] as further described below.

If the ALARM flag is not set at block 860b, the detector 500 determines whether the TEST flag is set at block 860c. If the TEST flag is set, the process proceeds to the LOOP2 sub-routine. If the TEST flag is not set at block 860c, the detector 500 decrements the TEST counter at block 860d and then determines whether the TEST counter is equal to zero at block 860e. If the TEST counter is not equal to zero, the process proceeds to the LOOP2 sub-routine. If the TEST counter is equal to zero at block 860e, the process proceeds to a TEST sub-routine as further described below.

FIG. 22 illustrates a NEG1 sub-routine to a reduction in the counts value to clear an alarm condition if the CO level is decreasing. At block 870a, the detector 500 clears a DIRECTION flag and subtracts a REDCT value from the ALARM register at block 870b. The detector 500 then determines whether the ALARM register is negative at block 870c. If the ALARM is not negative, the process proceeds to block 870d as further described below. If the ALARM is negative at block 870c, the detector 500 clears the ALARM register at block 870e and then determines whether the ALARM is less than an ALROFF value at block 870d. If the ALARM register is less than the ALROFF value, the detector clears the ALARM register at block 870f.

If the ALARM register is not less than the ALROFF value at block 870d, the detector 500 decrements a NEGATIVE READING counter at block 870g. If the NEGATIVE READING counter is not equal to zero, the process proceeds to the SHOW sub-routine as further described below. If the NEGATIVE READING counter is equal to zero, the detector 500 calls CLRREG at block 870h. The process then proceeds to the SHOW sub-routine.

Figure 23:
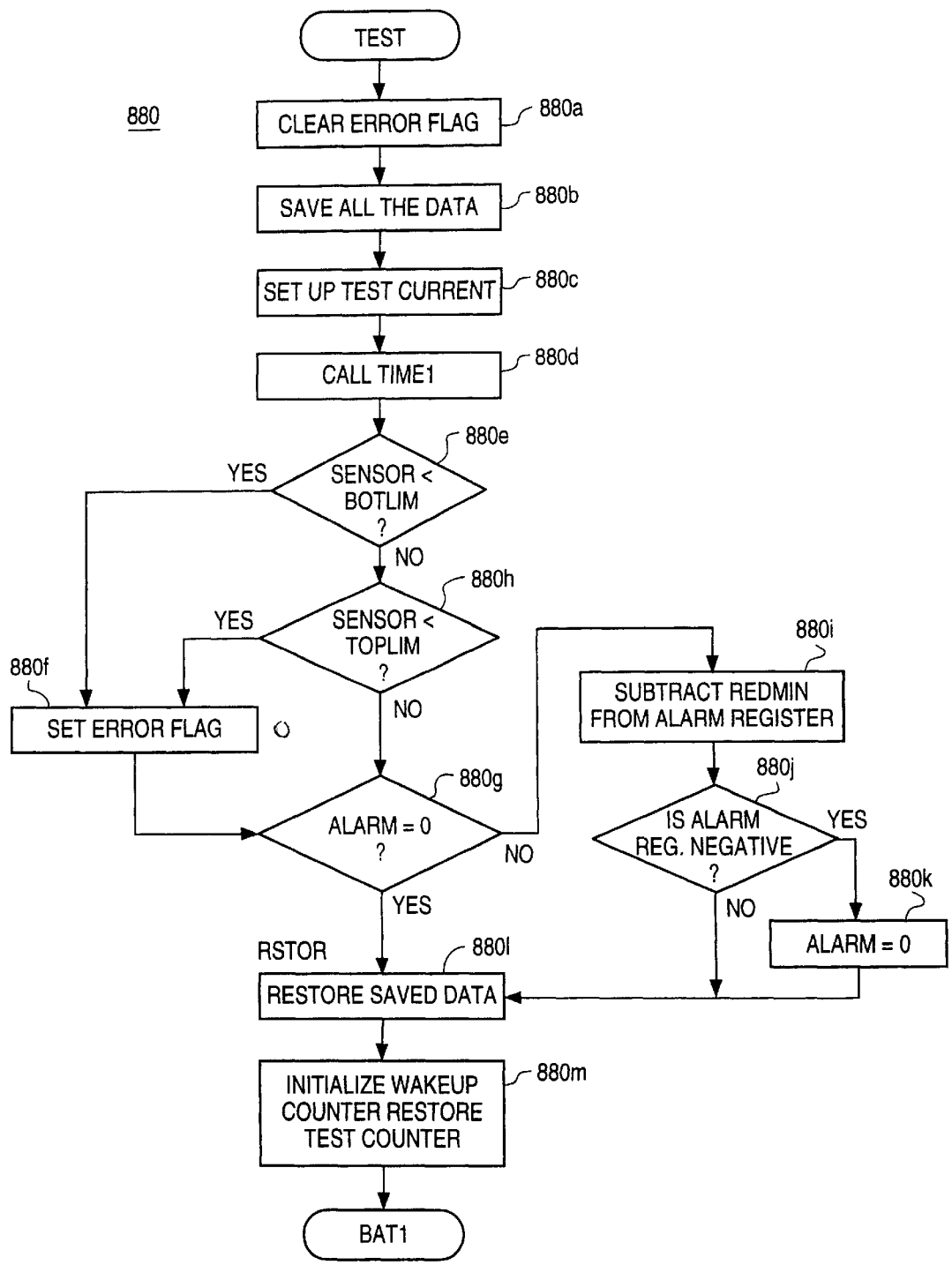
FIG. 23 is a flow diagram of a TEST sub-routine of the main routine of FIG. 16.

Referring now to FIG. 23, the TEST sub-routine 880 is illustrated. The TEST sub-routine 880 is utilized to test and exercise the carbon monoxide sensing electronics, while maintaining the previous samples and data acquired.

Initially, the detector 500 clears an ERROR flag at block 880a, saves all the data at block 880b, sets up a test current at block 880c, calls TIME1 at block 880d, and determines whether the sensor output is less than a BOTLIM value at block 880e.

If the sensor output is less than the BOTLIM value, the detector 500 sets an ERROR flag at block 880f, and then the process proceeds to block 880g as further described below. If the sensor output is not less than the BOTLIM value at block 880e, the detector 500 determines whether the sensor output is less than a TOPLIM value at block 880h.

If the sensor output is less than the TOPLIM value, the detector 500 sets an ERROR flag at block 880f, and the process proceeds to block 880g. If the sensor output is not less than the TOPLIM value at block 880h, the detector 500 determines whether the ALARM register is equal to zero at block 880g.

If the ALARM register is not equal to zero at block 880g, the detector 500 subtracts a REDMIN register from the ALARM register at block 880i, and then determines whether the ALARM register is negative at block 880j. If the ALARM register is not negative, the process proceed to block 880l as further described below. If the ALARM register is negative at block 880j, the detector 500 sets the ALARM register equal to zero at block 880k and then the process proceeds to block 880l as further described below.

If the ALARM register is equal to zero at block 880g, the detector 500 will restore the save data at block 880l. The detector 500 will then initialize the WAKEUP counter and restore the TEST counter at block 880m. The process then proceeds to the BAT1 sub-routine as further described below.

Figure 24:
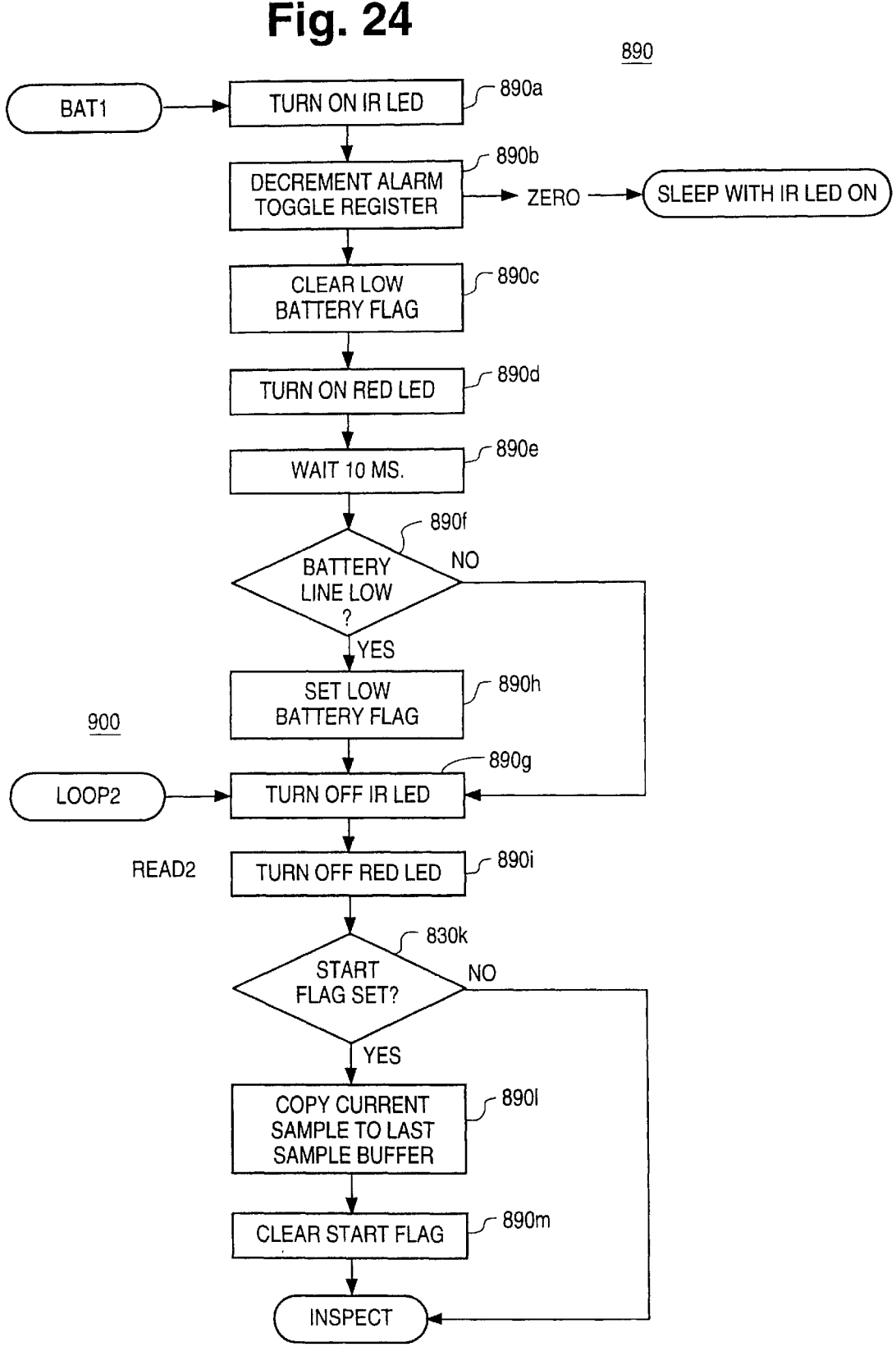
FIG. 24 is a flow diagram of a BAT1 sub-routine of the main routine of FIG. 16.

FIG. 24 illustrates the BAT1 sub-routine 890 and a Loop2 sub-routine 900. The BAT1 sub-routine 890 determines whether the battery of the detector 500 is at a sufficient voltage level and the LOOP2 sub-routine turns off the IR LED and power LED after a sample has been taken and stores the current sample value.

The detector 500 turns on the IR LED of the carbon monoxide sensor at block 890a and decrements a ALARM TOGGLE register at block 890b. If the ALARM TOGGLE is equal to zero at block 890b, the detector is put into the sleep mode with their LED on. If the ALARM TOGGLE is not equal to zero at block 890b, the detector 500 clears a LOW BATTERY flag at block 890c, turns on the red LED2 at block 890d, waits about 10 ms at block 890e, and then determines whether the battery line is at a low level at block 890f.

If the battery line is not at a low voltage level, the process proceeds to block 890g as further described below. If the battery line is at a low level at block 890f, the detector 500 sets a LOW BATTERY flag at block 890h, turns off their LED at block 890g, turns off the red LED at block 890i, and then determines whether a START flag has been set at block 890k.

If the START flag is not set, the process proceeds to a INSPECT sub-routine as further described below. If the START flag is set at block 890k, the detector unit 500 copies a current sample to a last sample buffer at block 890l, clears the START flag at block 890m, and then the process proceeds to the INSPECT sub-routine.

Figure 25:
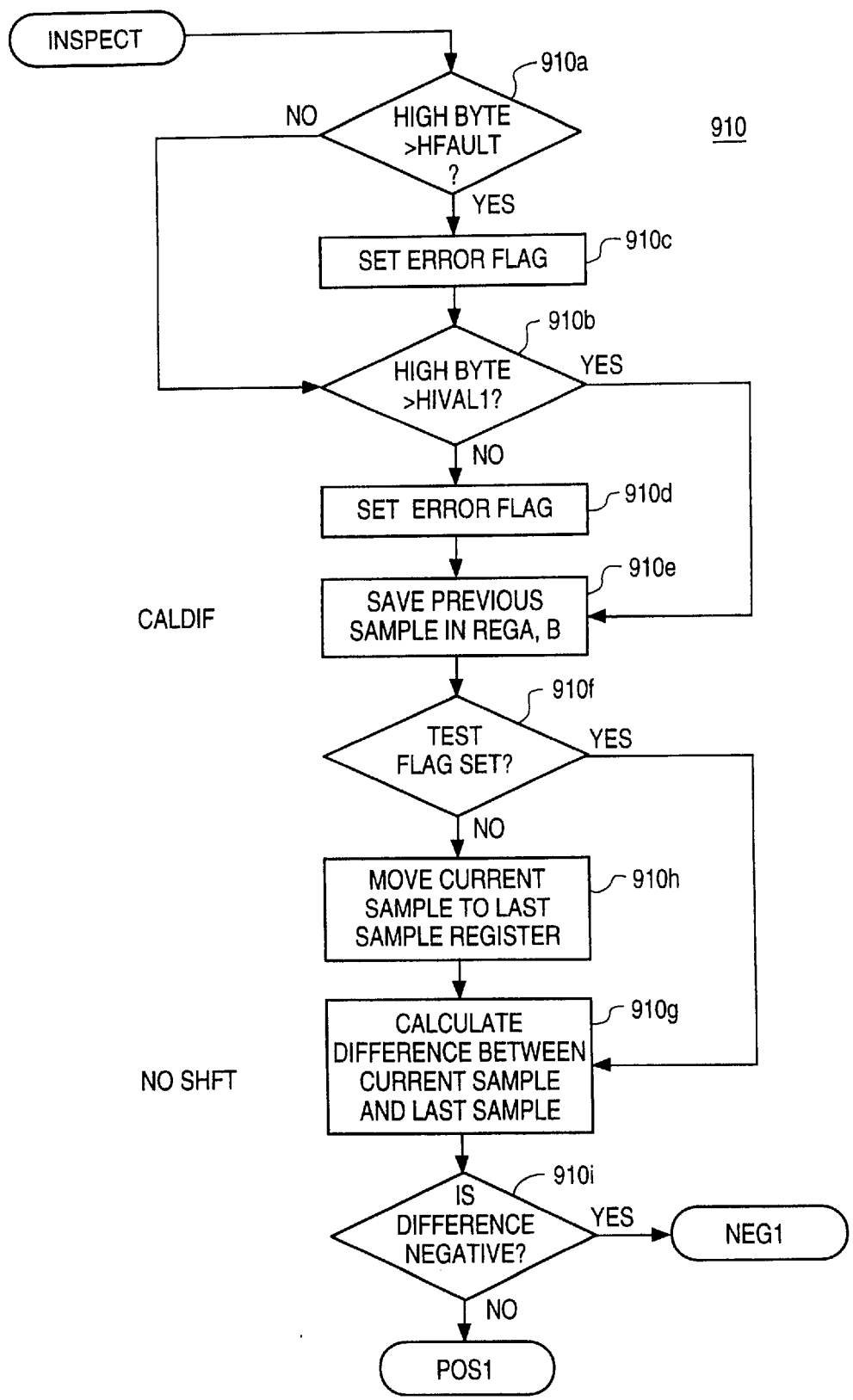
FIG. 25 is a flow diagram of an INSPECT sub-routine of the main routine of FIG. 16.

FIG. 25 illustrates the INSPECT sub-routine 910. The INSPECT sub-routine 910 is utilized to evaluate the difference between the previous sample and the present sample.

At block 910a, the detector 500 determines whether a HIGH BYTE is greater than an HFAULT value. If the HIGH BYTE is not greater than the HFAULT value, the process proceeds to block 910b as further described below. If the HIGH BYTE is greater than the HFAULT value at block 910a, the detector 500 sets an ERROR flag at block 910c and then determines whether the HIGH BYTE is greater than a HIVAL1 value at block 910b.

If the HIGH BYTE is greater than the HIVAL1 value, the process proceeds to block 910e as further described below. If the HIGH BYTE is not greater than the HIVLA1 value at block 910b, the detector 500 sets the ERROR flag at block 910d, saves a previous sample sin registers A and B at block 910e, and then determines whether the TEST flag is set at block 910f.

If the TEST flag is set, the process proceeds to block 910g as further described below. If the TEST flag is not set at block 910f, the detector 500 moves the current sample to the last sample register at block 910h, calculates the difference between the current sample and the last sample at block 910g, and then determines whether the difference is negative at block 910i.

If the difference is negative, the process proceeds to the NEG1 sub-routine as described above. If the difference is not negative at block 910i, the process proceeds to a POS1 sub-routine as further described below.

Figure 26:
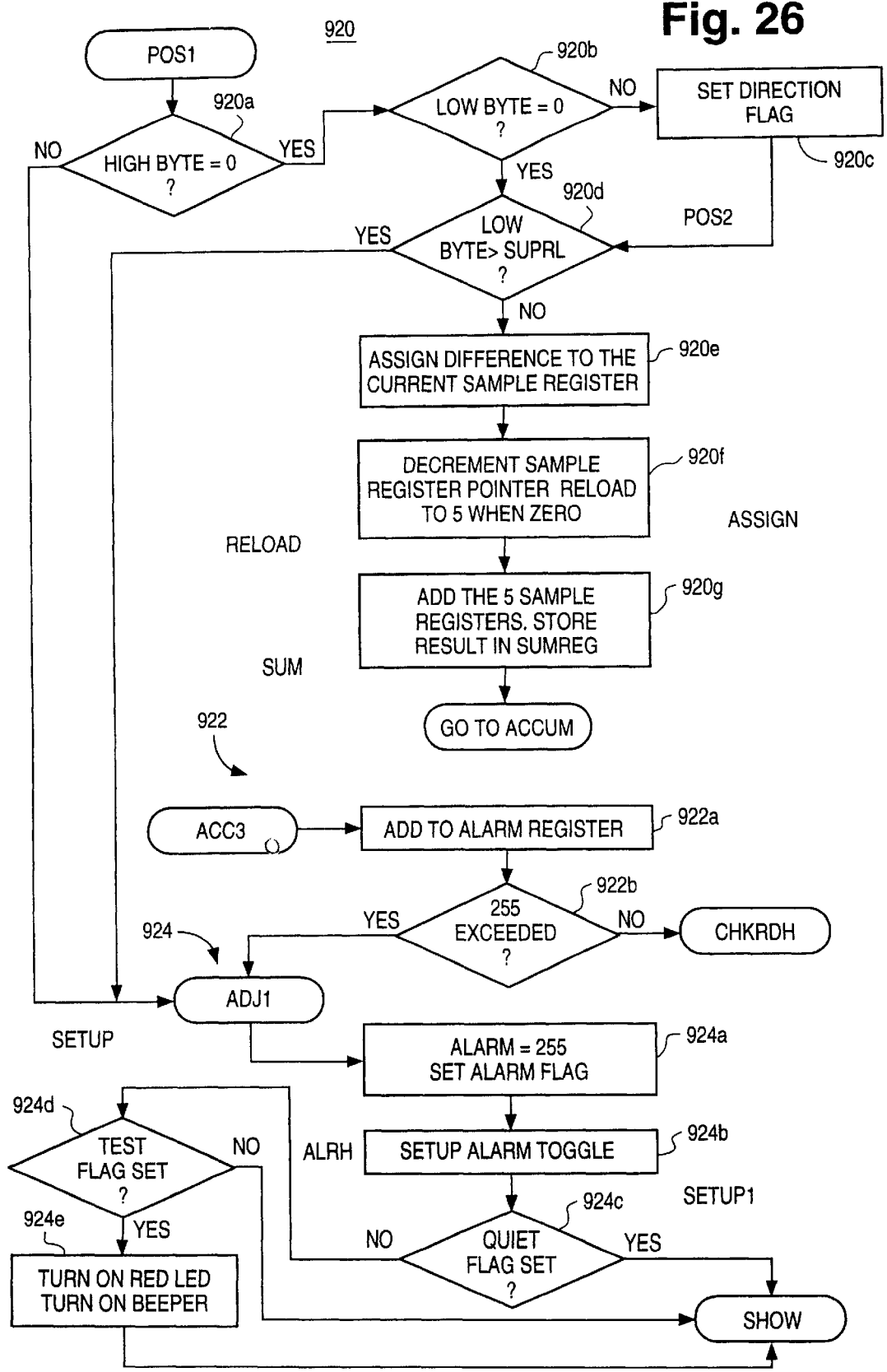
FIG. 26 is a flow diagram of a POS1 sub-routine, a ACC3 sub-routine, and ADJ1 sub-routine of the main routine of FIG. 16.

FIG. 26 illustrates the POS1 sub-routine 920 to determine if we are in a high level alarm and a ACC3 sub-routine 922 to add the equate for the previous sample to the alarm register. At block 920a, the detector 500 determines whether a HIGH BYTE is equal to zero. If the HIGH BYTE is not equal to zero, the process proceeds to a ADJ1 sub-routine 924 as further described below. If the HIGH BYTE is equal to zero, the detector 500 determines whether a LOW BYTE is equal to zero at block 920b.

If the LOW BYTE is not equal to zero, the detector 500 sets a DIRECTION flag at block 920c and the process proceeds to block 920d as further described below. If the LOW BYTE is equal to zero at block 920b, the detector 500 determines whether the LOW BYTE is greater than a SUPRL value at block 920d.

If the LOW BYTE is greater than the SUPRL value, the process proceeds to the ADJ1 sub-routine 924 as further described below. If the LOW BYTE is not greater than SUPRL at block 920d, the detector 500 assigns the difference to the current sample register at block 920e, decrements a sample register pointer and reloads the register pointer to five when the sample register pointer is equal to zero at block 920f. The detector 500 adds the five sample registers and stores the result in a SUMREG register at block 920g.

The process then proceeds to a ACCUM sub-routine as further described below.

During the ACC3 sub-routine 922, the detector 500 adds the difference to the ALARM register at block 922a, and then determines whether the ALARM register exceeds 255 at block 922b. If the ALARM register does not exceed 255, the process proceeds to a CHKRDH sub-routine as further described below. If the ALARM register exceeds 255 at block 922b, the process proceeds to the ADJ1 sub-routine 924.

During the ADJ1 sub-routine 924, the detector unit 500 determines whether the ALARM is equal to 255 and sets an ALARM flag at block 924a. The detector 500 then sets up an ALARM TOGGLE at block 924b and determines whether the QUIET flag is set at block 924c.

If the QUIET flag is set, the process proceeds to the SHOW sub-routine as further described below. If the QUIET flag is not set at block 924c, the detector 500 determines whether the TEST flag is set at block 924d.

If the TEST flag is not set, the process proceeds to the SHOW sub-routine. If the TEST flag is set at block 924d, the detector 500 turns on the red LED and turns on the beeper at block 924e. The process then proceeds to the SHOW sub-routine.

Figure 27:
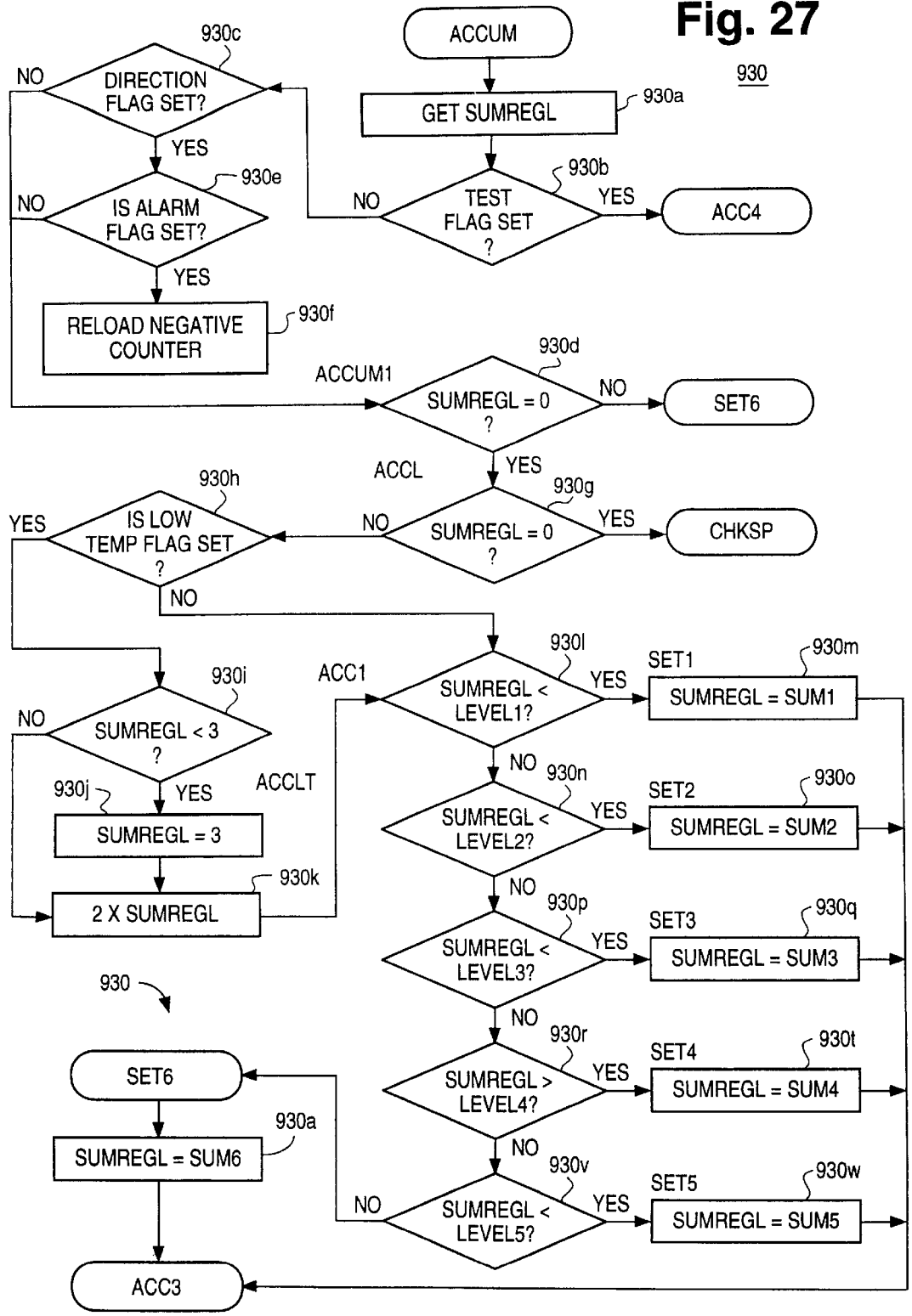
FIG. 27 is a flow diagram of an ACCUM sub-routine and a SET6 sub-routine of the main routine of FIG. 16.

FIG. 27 illustrates the ACCUM sub-routine 930 and a SET6 sub-routine. The ACCUM sub-routine 930 is utilized to determine what value to assign to the lower byte of the sum register, and the SET6 sub-routine is implemented to assign the sum 6 value to the low byte of the sum register.

At block 930a, the detector 500 obtains a SUMREGL value and then determines whether a TEST flag is set at block 930b. If the TEST flag is set, the process proceeds to a ACC4 sub-routine as further described below. If the TEST flag is not set at block 930b, the detector unit 500 determines whether a DIRECTION flag is set at block 930c.

If the DIRECTION flag is not set, the process proceeds to block 930d as further described below. If the DIRECTION flag is set at block 930c, the detector unit 500 determines if an ALARM flag is set at block 930e.

If the ALARM flag is not set, the process proceeds to block 930d. If the ALARM flag is set at block 930e, the detector 500 reloads the NEGATIVE counter at block 930f.

At block 930d, the detector 500 determines whether a SUMREGH value is equal to zero. If the SUMREGH value is not equal to zero, the process proceeds to a SET6 sub-routine 930. If the SUMREGH is equal to zero at block 930d, the detector unit 500 determines whether the SUMREGL value is equal to zero at block 930g.

If the SUMREGL value is equal to zero, the process proceeds to a CHKSP sub-routine as further described below. If the SUMREGL is not equal to zero at block 930g, the detector 500 determines whether a LOW TEMP flag is set at block 930h.

If the LOW TEMP flag is set at block 930h, the detector 500 determines whether the SUMREGL value is less than 3 at block 930i. If the SUMREGL value is less than three, the detector 500 sets the SUMREGL value equal to three at block 930j, and will times the SUMREGL by two at block 930k, and the process proceeds to block 930l. If the SUMREGL is not less than 3 at block 930i, the detector unit 500 times the SUMREGL by two at block 930k, and the process proceeds to block 930l.

Now, the detector unit 500 compares the SUMREGL to LEVEL1 through LEVEL5 values. If the SUMREGL is less than the LEVEL1 value, the detector unit 500 sets the SUMREGL value equal to a SUM1 value at block 930*m*. If the SUMREGL value is less than the LEVEL2 value at block 930*n*, the detector 500 sets the SUMREGL value equal to a SUM2 value at block 930*o*. If the SUMREGL value is less than the LEVEL3 value at block 930*p*, the detector 500 sets SUMREGL value equal to a SUM3 value at block 930*q*. If the SUMREGL value is less than the LEVEL4 value at block 930*r*, the detector 500 sets the SUMREGL value equal to a SUM4 value at block 930*t*. If the SUMREGL value is less than a LEVEL5 value at block 930*v*, the detector 500 sets the SUMREGL value equal to a SUM5 value at block 930*w*.

If the detector 500 has set the SUMREGL value equal to the SUM1 value, SUM2 value, the SUM3 value, the SUM4 value, or the SUM5, value the process proceeds to the ACC3 sub-routine as further described below. If the SUMREGL is not set to one of these values, the process proceeds to the SET6 sub-routine 930. Subsequently, the detector 500 sets the SUMREGL equal to SUM6 at block 930*a*. The process then proceeds to the ACC3 sub-routine as further described below.

Figure 28:
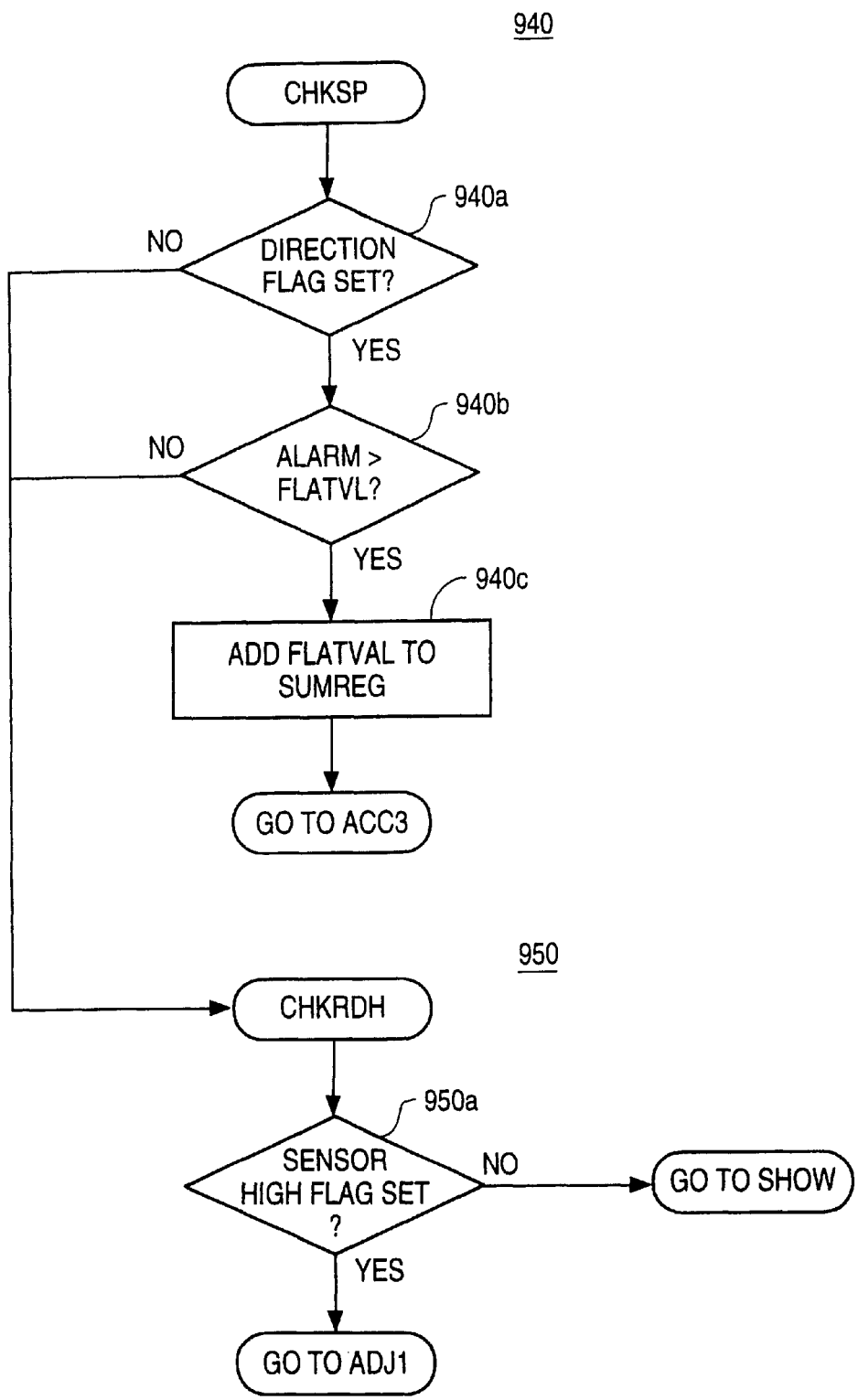
FIG. 28 is a flow diagram of a CHKSP sub-routine of the main routine of FIG. 16.

FIG. 28 illustrates the CHKSP sub-routine 940 and CHKRDH sub-routine 950. The CHKSP sub-routine 940 is utilized to check if the present sample is at a flat level or if it has changed direction from the previous sample.

At block 940*a*, the detector unit 500 determines whether a DIRECTION flag is set. If the DIRECTION flag is not set, the process proceeds to the CHKRDH sub-routine 950. If the DIRECTION flag is set at block 940*a*, the detector 500 determines whether a ALARM counter is greater than a FLATLVL value at block 940*b*.

If the ALARM counter is not greater than the FLATLVL counter, the process proceeds to the CHKRDH sub-routine 950. If the ALARM counter is greater than the FLATLVL value at block 940*b*, the detector 500 adds the FLATLVL value to a SUMREG register at block 940*g*, and the process proceeds to an ACC3 sub-routine as further described below.

The CHKRDH sub-routine 950 is utilized to determine the status of the sensor high flag. At block 950*a*, the detector determines whether a SENSOR HIGH flag is set at block 950*a*. If the SENSOR HIGH flag is not set, the process proceeds to the SHOW sub-routine as further described below. If the SENSOR HIGH flag is set at block 950*a*, the process proceeds to a ADJ1 sub-routine as further described below.

Figure 29:
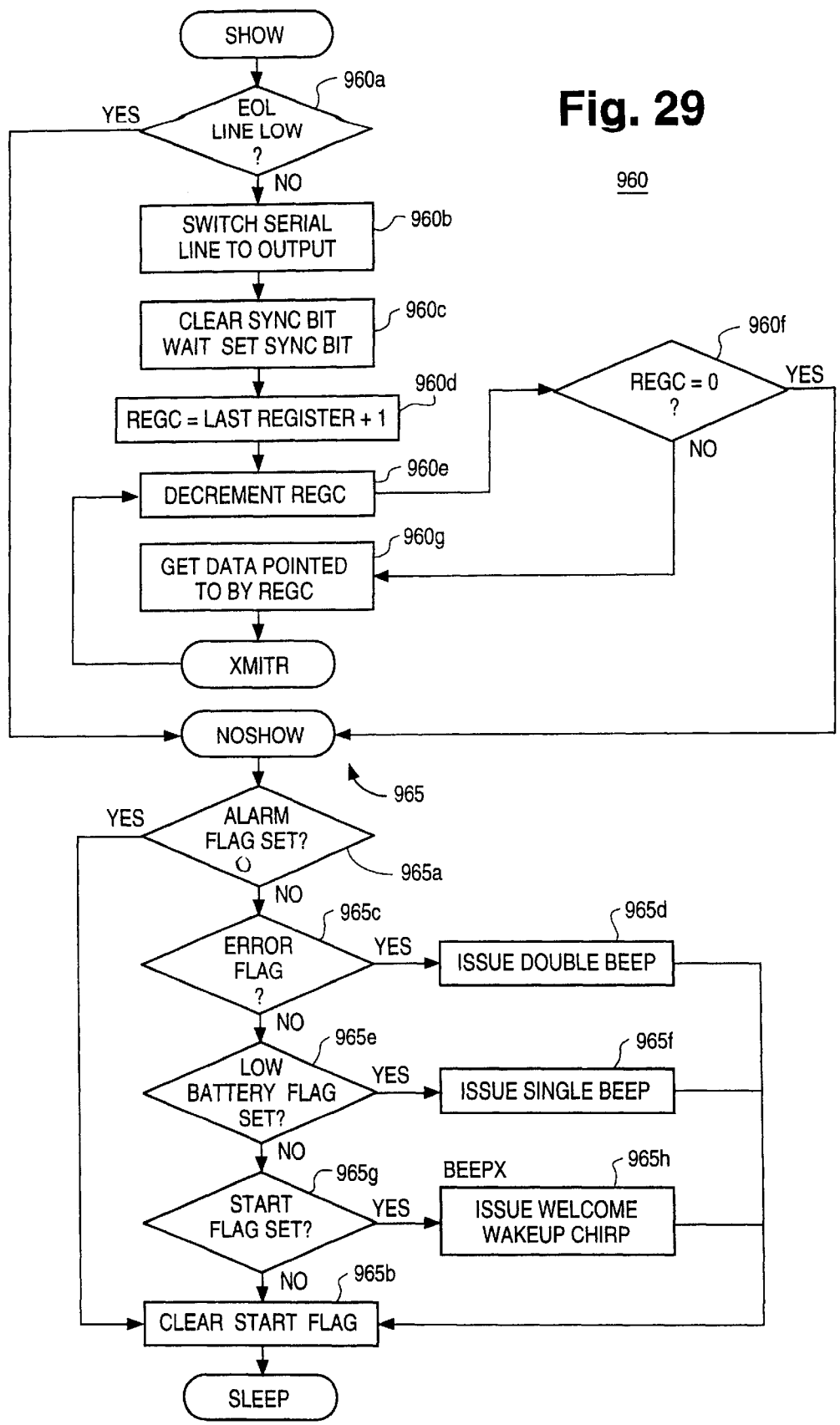
FIG. 29 is a flow diagram of a SHOW sub-routine and a NOSHOW sub-routine of the main routine of FIG. 16.

FIG. 29 illustrates a flow diagram of the SHOW sub-routine 960 and a NOSHOW sub-routine 965. The SHOW sub-routine 960 is utilized to present the data stream through RS-237 communication to peripherals and the power LED.

At block 960*a*, the detector 500 determines whether an EOL line is at a low level. If the EOL line is at a low level, the process proceeds to a NOSHOW sub-routine 965 as described below. If the EOL line is not at a low level at block 960*a*, the detector 500 switches a SERIAL line to an output at block 960*b*.

At block 960*c*, the detector 500 clears a SYNC bit, waits for a predetermined amount of time, and sets the SYNC bit. The detector 500 then sets an REGC register equal to the last register plus 1 at block 960*d*, decrements the REGC register at block 960*e*, and then determines whether the REGC register is equal to zero at block 960*f*.

If the REGC register is not equal to zero, the detector obtains the data pointed to by the REGC register and then the process proceeds to an XMITR sub-routine as further described below. If the REGC is equal to zero at block 960*f*, the process proceeds to the NOSHOW sub-routine 965.

The NOSHOW sub-routine 965 is utilized to determine if there is a low battery, error or power up flag set and sound the correct horn pattern. At block 965*a*, the detector 500 determines whether an ALARM flag is set. If the ALARM flag is set, the process proceeds to block 965*b* as further described below. If the ALARM flag is not set at block 965*a*, the detector 500 determines whether an ERROR flag is set at block 965*c*.

If the ERROR flag is set, the detector 500 issues a double beep at block 965*d*, and the process proceeds to block 965*b* as further described below. If the ERROR flag is not set at block 965*c*, the detector unit determines whether a LOW BATTERY flag is set at block 965*e*.

If the LOW BATTERY flag is set, the detector 500 issues a single beep at block 965*f*. If the LOW BATTERY flag is not set at block 965*e*, the detector determines whether a START flag is set at block 965*g*.

If the START flag is set, the detector 500 issues a welcome wake-up chirp at block 965*h*. If the START flag is not set at block 965*g*, the detector 500 clears the START flag at block 965*b* and the detector 500 is put into the sleep mode.

Figure 30:
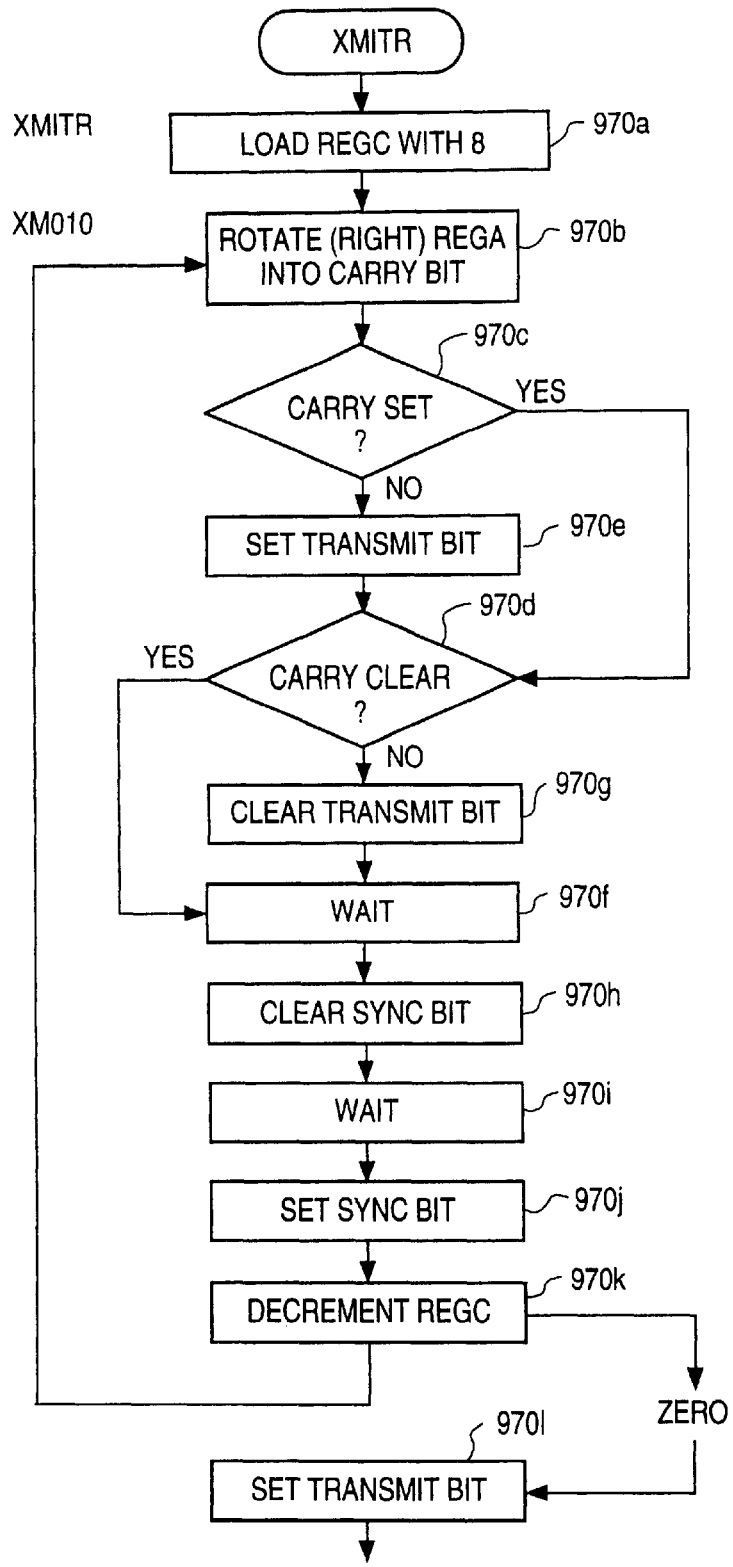
FIG. 30 is a flow diagram of a XMITR sub-routine of the main routine of FIG. 16.

FIG. 30 illustrates the XMITR sub-routine 970 to synchronize the data stream. At block 970*a*, a REGC register is loaded with 8. The detector 500 then rotates the value of a REGA register into a CARRY bit at block 970*b* and then determines whether the CARRY bit is set a block 970*c*.

If the CARRY bit is set, the process proceeds to block 970*d* as further described below. If the CARRY bit is not set at block 970*c*, the detector 500 sets a TRANSMIT bit a block 970*e* and then determines whether the CARRY bit is cleared at block 970*d*.

If the CARRY bit is cleared, the process proceeds to block 970*f* as further described below. If the CARRY bit is not cleared at block 970*d*, the detector 500 clears the TRANSMIT bit a block 970*g*, waits a predetermined amount of time at block 970*f*, clears a SYNC bit at block 970*h*, waits another predetermined amount of time at block 970*i*, sets the SYNC bit at block 970*j*, and decrements a REGC register at block 970*k*.

The process then proceeds to block 970*b* unless the REGC register is equal to zero. If the REGC register is equal to zero at block 970*k*, the detector 500 sets the TRANSMIT bit at block 970*l*, and byte has been sent, continue.

Figure 31:
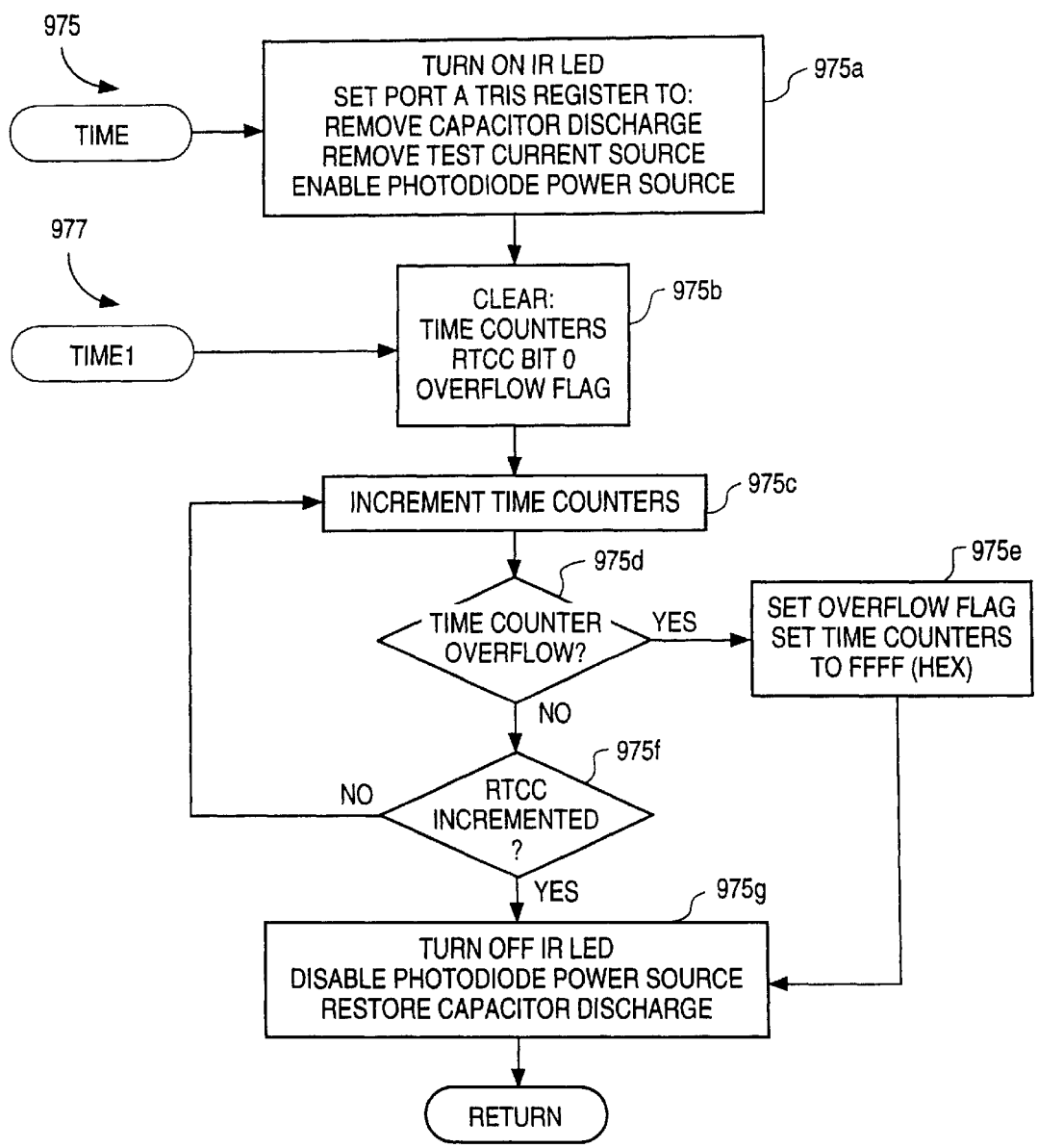
FIG. 31 is a flow diagram of a TIME sub-routine and TIME 1 sub-routine of the main routine of FIG. 16.

FIG. 31 illustrates the TIME sub-routine 975 and the TIME1 sub-routine 977. The TIME and TIME1 sub-routines are utilized to take a carbon monoxide sample.

At block 975*a*, the detector unit 500 turns on the IR LED, sets a TRIS register to remove capacitor discharge, removes test current source, and enables the photo diode power source. At block 975*b*, the detector 500 clears the time counters, a RTCC bit, and an OVERFLOW flag. The detector 500 then increments the time counters at block 975*c*, and then determines whether the time counter equals an overflow value at block 975*d*.

If the time counter is equal to the overflow value, the detector 500 sets an overflow flag and sets counters to FFFF at block 975*e*. The process then proceeds to block 975*g* as further described below. If the time counter is not equal to the overflow value at block 975*d*, the detector 500 determines whether the RTCC should be incremented at block 975*f*.

If the RTCC should not be incremented, the process proceeds to block 975*c*. If the RTCC is to be incremented at block 975*f*, the detector 500 will turn off the IR LED, disable the photo diode power source, and restore the capacitor discharge at block 975g. The process then will proceed to the beginning of the TIME sub-routine 975 or TIME1 sub-routine 977.

Figure 32:
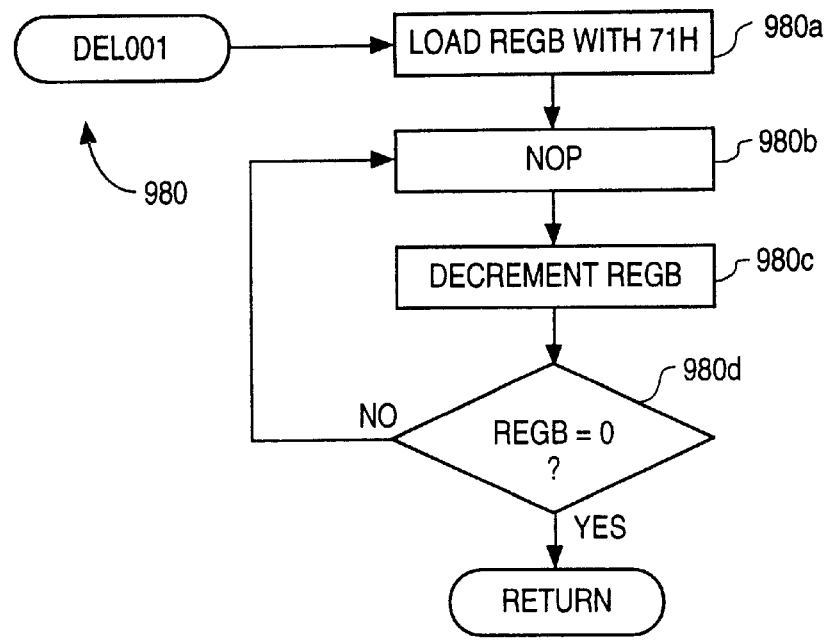
FIG. 32 is a flow diagram of a DEL001 sub-routine, of the main routine of FIG. 16.

FIG. 32 illustrates a DEL001 sub-routine 980. The DEL001 sub-routine 980 is utilized as a fixed time delay for the microcontroller timing. At block 980a, the detector 500 loads a REGB register with 71H, NOP at block 980b, decrements the REGB register at block 980c, and then determines whether the REGB register is equal to zero at block 980d.

The process will proceed to block 980b unless the REGB register is equal to zero. When the REGB register 13 is equal to zero, the process will return to the beginning of the DEL001 sub-routine 980.

Figure 33:
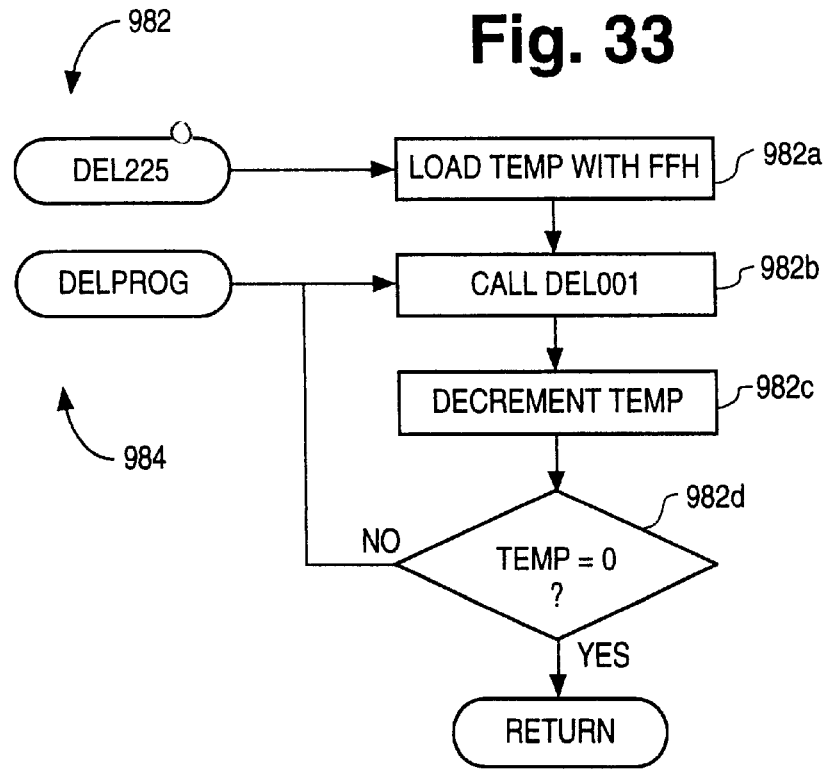
FIG. 33 is a flow diagram of a DEL225 sub-routine, and a DELPROG sub-routine of the main routine of FIG. 16.

FIG. 33 illustrates a DEL255 sub-routine 982 and a DELPROG sub-routine 984 for a fixed timing delay on the microcontroller. At block 982a, the detector 500 loads a TEMP register with FFh. The detector 500 then calls DEL001 at block 982b, decrements the TEMP register at block 982c, and then determines whether the TEMP register is equal to zero at block 982d.

The process proceeds to block 982b unless the TEMP register is equal to zero. When the TEMP register is equal to zero, the process returns to the beginning of the DEL255 sub-routine 982 or the DELPROG sub-routine 984.

FIG. 34 illustrates a CLRREG sub-routine 986. The CLRREG sub-routine 986 is utilized to reset the microcontroller at power-up, and ensure LED's and horn are off.

As shown in FIG. 34, the detector 500 clears one or more SAMPLE registers at block 986a, clears one or more flags at block 986b, sets a START flag at block 986c, and clears Port B at block 986d. The detector 500 then turns off the red LED2 and yellow LED1 at block 986e. The process then returns to the beginning of the CLRREG sub-routine 986.

FIG. 35 shows a M16 sub-routine 988 to add the determined weight to the low byte of the sum register. At block 988a, the detector 500 adds W to the SUMREGL register. The detector 500 then determines whether a CARRIER register is set at block 988b.

If the CARRIER register is not set, the process returns to the beginning of the M16 sub-routine 988. If the CARRIER register is set at block 988b, the detector 500 increments the SUMREG register at block 988c and then the process returns to the beginning of the M16 sub-routine 988.

Although the present invention has been described in detail by way of illustration and example, it should be understood that a wide range of changes and modifications can be made to the preferred embodiments described above without departing in any way from the scope and spirit of the invention. Thus, the described embodiments are to be considered in all respects only as illustrative and not restrictive, and the scope of the invention is, therefore, indicated by the appended claims rather than the foregoing description. All changes that come within the meaning and range of equivalency of the claims are to be embraced within their scope.

What is claimed:

1. An apparatus to detect a condition in the environment comprising:
   a sensing device having a light emitting source to direct light at a sensor and a light receiving device to detect the light passing through the sensor, the sensor changing color upon exposure to carbon monoxide;
   a smoke detector having a first electrode disposed between second and third electrodes;
   a comparator having a first terminal, a second terminal, and an output terminal, the first terminal electrically coupled to the first electrode and the second terminal being maintained at a reference voltage, the comparator producing a detection signal upon the voltage at the first terminal exceeding the reference voltage applied at the second terminal;
   control circuitry selectively activating the light emitting source to cause the voltage of the light receiving device to increase, the control circuitry determining the amount of time for the voltage of the light receiving device to reach a predetermined voltage level, the control circuitry computing a rate of change between a plurality of times for the light receiving device to reach the predetermined voltage level, the control circuitry also being responsive to the detection signal from the comparator wherein the control circuitry includes executable instructions to automatically and periodically test the operation of the sensing device and the smoke detector;
   an alarm energizable to reproduce a first prestored audible horn output pattern when the rate of change between the plurality of times reaches a predetermined value;
   to reproduce a second prestored audible horn output pattern when the first electrode reaches a preset voltage level; and
   an elongated multi-function, test initiating member movable from a first to a second position wherein in response to the member being moved to the second position, the control circuitry enters a test mode and generates audible and visible indicia thereof.

2. The apparatus of claim 1 further comprising a capacitor electrically coupled to the light receiving device to cause the voltage of the light receiving device to increase linearly.

3. An apparatus to detect a condition in the environment comprising:
   a sensing device having a light emitting source to direct light at a sensor and a light receiving device to detect the light passing through the sensor, the sensor changing color upon exposure to carbon monoxide:
   a smoke detector having a first electrode disposed between second and third electrodes;
   a comparator having a first terminal, a second terminal and an output terminal, the first terminal electrically coupled to the first electrode and the second terminal being maintained at a reference voltage the comparator producing a detection signal upon the voltage at the first terminal exceeding the reference voltage applied at the second terminal;
   control circuitry selectively activating the light emitting source to cause the voltage of the light receiving device to increase, the control circuitry determining the amount of time for the voltage of the light receiving device to reach a predetermined voltage level, the control circuitry computing a rate of change between a plurality of times for the light receiving device to reach the predetermined voltage level, the control circuitry also being responsive to the detection signal from the comparator; and
   an alarm energizable to produce a first pattern when the rate of change between the plurality of times reaches a predetermined value;
   to produce a second pattern when the first electrode reaches a preset voltage level; and
   further comprising driving circuitry to supply a substantially constant current level to the light emitting source to maintain the output of the light emitting source at a substantially constant level.

4. The apparatus of claim 3 wherein the driving circuitry includes a first resistor in series with a second resistor, and a thermistor in parallel with the second resistor.

5. The apparatus of claim 1 further including a battery to provide power to the control circuitry.

6. The apparatus of claim 5 further comprising reverse bias protection circuitry coupled to the battery.

7. The apparatus of claim 1 wherein the sensor device comprises a biomimetic element.

8. The apparatus of claim 1 wherein the smoke detector includes an ionization chamber.

9. The apparatus of claim 1 wherein the light emitting source comprises a light emitting diode.

10. An apparatus as in claim 1 wherein the control circuitry includes a programmed processor and a stored plurality of audible output patterns.

11. A detector comprising:
   a multi-sided housing which defines an internal region wherein at least some of the sides are planar;
   a gas sensor, carried in the region;
   a smoke sensor, carried in the region;
   at least three different, prestored, alarm indicating horn patterns wherein two of the patterns indicate the same type of alarm condition wherein the two patterns are associated with the smoke sensor and the third is associated with the gas sensor; and
   an elongated test initiating element carried on a surface of the housing bounded by the sides.

12. A detector as in claim 11 which includes a self-contained replaceable power supply.

13. A detector as in claim 11 wherein the housing is symmetrical about a first center-line.

14. A detector as in claim 11 wherein the housing has a periphery having at least six planar sides.

15. A detector as in claim 14 which includes a removable, protective, planar element which removably covers a portion of the gas sensor to prevent deterioration thereof prior to use.

16. A detector as in claim 11 wherein the surface of the housing is perforated by a flame shaped opening wherein the opening, when illuminated, is indicative of a detected fire condition.

17. A detector as in claim 11 wherein the surface of the housing is perforated by a non-circular opening wherein the opening, when illuminated, is indicative of a detected gas condition.

18. A detector as in claim 11 which includes at least a programmed control element carried by the housing and pre-stored instructions, executed by the processor for selecting one of the two smoke indicating alarm patterns.

19. A combined gas and smoke detector comprising:
   a gas sensor;
   a smoke sensor; and
   control circuits, coupled to the sensors, including a programmed processor having stored therein at least a gas related audible, horn output pattern and two different smoke related audible, intermittent horn output patterns wherein only a selected one of the two smoke patterns can be output in response to detection of smoke.

20. A detector as in claim 19 which includes a common audible output device coupled to the circuits, wherein in response to the processor outputting a pattern, the output device converts the pattern to a respective audible alarm output.

21. A detector as in claim 20 which includes a housing perforated by a gas indicating output symbol and a smoke indicating output symbol and first and second illuminable elements carried in the housing adjacent respective of the perforations wherein the elements are coupled to the processor and wherein a respective one of the elements is illuminated by the processor in response to detection of selected gas or smoke.

22. A detector as in claim 19 which includes battery monitoring circuitry coupled to the processor whereby the processor carries out a battery monitoring function.

23. A detector as in claim 21 wherein the housing is bounded by a plurality of planar side surfaces.

24. A detector as in claim 14 wherein, the housing is substantially symmetrical about a single centerline.

25. A detector as in claim 19 which includes a movable rectangular test initiating element.

26. A detector as in claim 19 which includes a planar cover member removably attached to the gas sensor and removable when the detector is placed into service to expose the sensor to ambient airborne gas.

27. An apparatus comprising:
   a gas sensor;
   a smoke sensor;
   control circuitry including a programmed processor coupled to the sensors, the control circuitry determining if a predetermined gas condition has been sensed, the control circuitry also determining if a predetermined smoke condition has been sensed wherein the processor stores at least first and second non-verbal alarm specifying horn patterns; and
   an alarm energizable to produce the first pattern when the gas condition is present, and to produce the second pattern in the presence of the predetermined smoke condition;
   wherein the processor stores at least one additional smoke alarm specifying horn pattern, and wherein the second pattern and the one additional pattern are different and only a selected one of the two is produced in response to a smoke condition.

28. The apparatus of claim 27 wherein the gas sensor includes a biomimetic material that responds to the presence of carbon monoxide.

29. A self-contained, combined, gas and smoke detector comprising:
   a gas sensor;
   a smoke sensor;
   a programmed control element coupled to both of the sensors;
   a housing which defines an internal region for receiving the sensors and the control element wherein the housing is perforated with a first opening shaped as a fire; and
   a removable protective planar element, covering at least a part of the gas sensor within the housing wherein the element is applied during manufacture and is removed once the detector has been placed into service; and
   wherein the gas sensor includes a light emitting source and wherein the control element comprises circuitry for supplying a substantially constant current level to the source to maintain the output of the light emitting source at a substantially constant level.

30. An apparatus to detect a condition in the environment comprising:
   a sensing device having a light emitting source to direct light at a sensor and a light receiving device to detect the light passing through the sensor, the sensor changing color upon exposure to carbon monoxide;

a smoke sensor;

control circuitry, coupled to the sensing device and the smoke sensor, wherein the circuitry selectively activates the light emitting source to cause the voltage of the light receiving device to increase, the control circuitry further comprising driving circuitry to supply a substantially constant current level to the light emitting source to maintain the output of the light emitting source at a substantially constant level even in the presence of a decrease in applied voltage.

31. A detector comprising:

a housing which defines an internal region;

a user non-replacable biomemetic-type gas sensor carried in the region wherein during manufacture, the gas sensor is sealed with a user removable planar sealing tape which is located at least in part in the internal region;

a fire sensor carried in the region;

a programmed processor carried in the region, coupled to the sensors, including at least two pre-stored, different fire specifying tonal alarm patterns and executable instructions for selecting and outputting one of the two patterns in response to sensed fire; and instructions executable by the processor for automatically and periodically testing the sensors.

32. A detector comprising:

a housing which defines an internal region;

a user non-replacable biomemetic-type gas sensor carried in the region wherein during manufacture, the gas sensor is sealed with a user removable planar sealing tape which is located at least in part in the internal region;

a fire sensor carried in the region;

a programmed processor carried in the region, coupled to the sensors;

instructions executable by the processor for automatically and periodically testing the sensors; and circuitry for coupling a constant current to the gas sensor.

33. A detector comprising:

a housing which defines an internal region;

a user non-replacable biomemetic-type gas sensor carried in the region wherein during manufacture, the gas sensor is sealed with a user removable planar sealing tape;

a fire sensor carried in the region;

a programmed processor carried in the region, coupled to the sensors; and at least two pre-stored, different fire specifying tonal alarm patterns and executable instructions for selecting and outputting one of the two patterns in response to sensed fire.

34. A detector as in claim 33 which includes circuitry for coupling a constant current to the gas sensor.

35. A detector as in claim 33 which includes instructions executable by the processor for automatically and periodically testing the sensors.

36. A detector as in claim 34 which includes instructions executable by the processor for automatically and periodically testing the sensors.

* * * * *